US011174273B2

(12) United States Patent
Wallace et al.

(10) Patent No.: US 11,174,273 B2
(45) Date of Patent: *Nov. 16, 2021

(54) QUINAZOLINE ANALOGS AS RECEPTOR TYROSINE KINASE INHIBITORS

(71) Applicant: Array BioPharma Inc., Boulder, CO (US)

(72) Inventors: Eli Wallace, Richardson, TX (US); George Topalov, Pittsburgh, PA (US); Joseph Lyssikatos, Piedmont, CA (US); Alexandre Buckmelter, Westford, MA (US); Qian Zhao, El Cerrito, CA (US)

(73) Assignee: Array Biopharma Inc., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/264,194

(22) Filed: Jan. 31, 2019

(65) Prior Publication Data

US 2019/0161500 A1    May 30, 2019

Related U.S. Application Data

(60) Continuation of application No. 15/606,928, filed on May 26, 2017, now Pat. No. 10,221,194, which is a continuation of application No. 13/607,016, filed on Sep. 7, 2012, now Pat. No. 9,676,791, which is a continuation of application No. 12/249,421, filed on Oct. 10, 2008, now Pat. No. 8,278,314, which is a division of application No. 10/914,974, filed on Aug. 10, 2004, now Pat. No. 7,452,895, which is a continuation-in-part of application No. 10/642,440, filed on Aug. 14, 2003, now Pat. No. 7,501,427.

(60) Provisional application No. 60/551,718, filed on Mar. 10, 2004.

(51) Int. Cl.
A61K 31/517     (2006.01)
C07D 498/10    (2006.01)
C07D 239/94    (2006.01)
C07D 401/12    (2006.01)
C07D 413/12    (2006.01)
C07D 413/14    (2006.01)
C07D 417/14    (2006.01)
C07D 498/04    (2006.01)
A61P 35/00       (2006.01)
A61P 29/00       (2006.01)

(52) U.S. Cl.
CPC ............ C07D 498/10 (2013.01); A61P 29/00 (2018.01); A61P 35/00 (2018.01); C07D 239/94 (2013.01); C07D 401/12 (2013.01); C07D 413/12 (2013.01); C07D 413/14 (2013.01); C07D 417/14 (2013.01); C07D 498/04 (2013.01)

(58) Field of Classification Search
CPC ............... C07D 239/94; A61K 31/517

USPC .......... 544/284; 514/266.2, 266.21
See application file for complete search history.

(56) References Cited

U.S. PATENT DOCUMENTS

| 2,583,774 | A | 1/1952 | Hoffman |
|---|---|---|---|
| 3,890,319 | A | 6/1975 | Danielewicz et al. |
| 5,112,817 | A | 5/1992 | Fukazawa et al. |
| 5,204,348 | A | 4/1993 | Fukazawa et al. |
| 5,405,843 | A | 4/1995 | Fukazawa et al. |
| 5,502,187 | A | 3/1996 | Ayer et al. |
| 5,821,246 | A | 10/1998 | Brown et al. |
| 5,955,464 | A | 9/1999 | Barker |
| 6,017,922 | A | 1/2000 | Stogniew et al. |
| 6,127,374 | A | 10/2000 | Bridges |
| 6,169,091 | B1 | 1/2001 | Cockerill et al. |
| 6,184,225 | B1 | 2/2001 | Thomas et al. |
| 6,225,318 | B1 | 5/2001 | Sobolov-Jaynes et al. |
| 6,344,459 | B1 | 2/2002 | Bridges et al. |
| 6,391,874 | B1 | 5/2002 | Cockerill et al. |
| 6,399,602 | B1 | 6/2002 | Barker et al. |
| 6,465,472 | B1 | 10/2002 | Upasani et al. |
| 6,602,863 | B1 | 8/2003 | Bridges et al. |
| 6,800,605 | B1 | 10/2004 | Friends et al. |
| 6,828,320 | B2 | 12/2004 | Cockerill et al. |
| 6,897,214 | B2 | 5/2005 | Barker et al. |
| 7,081,461 | B1 | 7/2006 | Mortlock et al. |
| 7,109,164 | B2 | 9/2006 | Friends et al. |
| 7,452,895 | B2 | 11/2008 | Wallace |
| 7,501,427 | B2 | 3/2009 | Wallace |
| 7,585,975 | B2 | 9/2009 | Wallace |
| 7,777,032 | B2 | 8/2010 | Wallace et al. |
| 8,278,314 | B2 | 10/2012 | Wallace et al. |
| 8,648,087 | B2 | 2/2014 | Lyssikatos et al. |
| 9,676,791 | B2 | 6/2017 | Wallace et al. |
| 9,693,989 | B2 | 7/2017 | Lyssikatos et al. |
| 10,221,194 | B2 | 3/2019 | Wallace et al. |
| 2002/0042409 | A1 | 4/2002 | Luzzio et al. |
| 2002/0169165 | A1 | 11/2002 | Kath et al. |

(Continued)

FOREIGN PATENT DOCUMENTS

EP          1066039 A1    1/2001
KR     19990082583 A    11/1999

(Continued)

OTHER PUBLICATIONS

U.S. Appl. No. 10/914,974, U.S. Pat. No. 7,452,895.
U.S. Appl. No. 10/642,440, U.S. Pat. No. 7,501,427.
U.S. Appl. No. 12/081,725, U.S. Pat. No. 7,585,975.
U.S. Appl. No. 12/496,973, U.S. Pat. No. 7,777,032.
U.S. Appl. No. 12/249,421, U.S. Pat. No. 8,278,314.
U.S. Appl. No. 13/607,016, U.S. Pat. No. 9,676,791.
U.S. Appl. No. 15/606,928, U.S. Pat. No. 10,221,194.
U.S. Appl. No. 12/085,048, U.S. Pat. No. 8,648,087.
U.S. Appl. No. 14/034,361, U.S. Pat. No. 9,693,989.

(Continued)

Primary Examiner — Susanna Moore
(74) Attorney, Agent, or Firm — Viksnins Harris Padys Malen LLP

(57) ABSTRACT

The invention includes methods of using compounds of Formula I as type I receptor tyrosine kinase inhibitors and for the treatment of hyperproliferative diseases such as cancer.

2 Claims, 6 Drawing Sheets

(56) References Cited

U.S. PATENT DOCUMENTS

| | | |
|---|---|---|
| 2004/0158065 A1 | 8/2004 | Barth et al. |
| 2004/0242604 A1 | 12/2004 | Bhattacharya et al. |
| 2005/0043334 A1 | 2/2005 | Wallace et al. |
| 2005/0043336 A1 | 2/2005 | Hennequin et al. |
| 2005/0101616 A1 | 5/2005 | Wallace et al. |
| 2005/0101617 A1 | 5/2005 | Wallace et al. |
| 2005/0101618 A1 | 5/2005 | Connell et al. |
| 2005/0119288 A1 | 6/2005 | Bhattacharya et al. |
| 2006/0025430 A1 | 2/2006 | Mishani et al. |
| 2014/0023643 A1 | 1/2014 | Lyssikatos et al. |
| 2017/0252317 A1 | 9/2017 | Lyssikatos et al. |

FOREIGN PATENT DOCUMENTS

| | | |
|---|---|---|
| WO | 1996009294 A1 | 3/1996 |
| WO | 1996015118 A1 | 5/1996 |
| WO | 1996016960 A1 | 6/1996 |
| WO | 1997013771 A1 | 4/1997 |
| WO | 1997030034 A1 | 8/1997 |
| WO | 1998002434 A1 | 8/1997 |
| WO | 1999009016 A1 | 2/1999 |
| WO | 1999024440 A1 | 5/1999 |
| WO | 1999044612 A1 | 9/1999 |
| WO | 2000031048 A1 | 6/2000 |
| WO | 2000042022 A1 | 7/2000 |
| WO | 2001094353 A1 | 12/2001 |
| WO | 2001098277 A2 | 12/2001 |
| WO | 2002002552 A1 | 1/2002 |
| WO | 2003015778 A1 | 2/2003 |
| WO | 20030037252 A2 | 5/2003 |
| WO | 2006071017 A1 | 7/2006 |
| WO | 2007059257 A2 | 5/2007 |

OTHER PUBLICATIONS

U.S. Appl. No. 15/599,867, 2017-0252317.
KR 1999-0082583, WO 1997/030034.
EP 1066039, WO 1999/044612.
Chinese, Patent Application No. 200480026458.9, dated Jul. 12, 2010.
Chinese Decision of Rejection, with English translation, issued in Chinese Patent Application No. 200480026458.9, dated Jul. 12, 2010.
Chinese State, Intellectual Property Office (SIPO) First Office Action, Chinese Application No. CN 200480026458.9 dated Mar. 14, 2008.
Colombian Office Action, with English translation, issued in Colombian Patent Application No. 06.025.746 dated Aug. 24, 2009.
European Search Report, issued in European Patent Application No. EP 04 78 0990, dated Oct. 31, 2008.
European Search Report, issued in European Patent Application No. EP 04 78 0990, dated Sep. 3, 2007.
Filipino Office Action, issued in Philippines Patent Application No. 1-2006-500337, dated Aug. 12, 2009.
Indian Office Action, with English translation, issued in Indian Patent Application No. 688/DELNP/2006, dated May 22, 2009.
Korean Notice, of Preliminary Rejection, with English translation, issued in Korean Patent Application No. KR 10-2006-7003060 dated Jun. 17, 2009.
Korean Office Action, with English translation, issued in Korean Patent Application No. KR 10-2010-7000942 dated Jun. 28, 2010.
Rusnak, et al., "The Characterization of Novel, Dual ErbB-2/EGFR, Tyrosine Kinase Inhibitors: Potential Therapy for Cancer", Cancer Research, vol. 61, 7196-7203 (2001).
Rusnak, et al., "The Effects of the Novel, Reversible Epidermal Growth Factor Receptor/ErbB-2 Tyrosine Kinase Inhibitor, GW2016, on the Growth of Human Normal and Tumor-derived Cell Line in Vitro and in Vivo", Molecular Cancer Therapeutics, vol. 1, 85-94 (2001).
Shi, et al., "QSAR analysis of tyrosine kinase inhibitor using modified ant colony optimization and multiple linear regression", European Journal of Medicinal Chemistry vol. 42, 81-86, Elsevier Masson (2007).
Taiwanese Office Action, with English translation, issued in Taiwanese Patent Application No. 93124336, response due Apr. 8, 2010.
U.S. Notice, of Allowance issued in U.S. Appl. No. 12/496,973 dated Mar. 23, 2010.
Vippagunta, et al., "Crystalline Solids", Advanced Drug Delivery Reviews 48, 3-26 (2001).

QUINAZOLINE ANALOGS AS RECEPTOR TYROSINE KINASE INHIBITORS

CROSS-REFERENCE TO RELATED APPLICATIONS

This application is a Continuation of U.S. patent application Ser. No. 15/606,928, filed May 26, 2017, now U.S. Pat. No. 10,221,194, which is a Continuation of U.S. patent application Ser. No. 13/607,016, filed Sep. 7, 2012, now U.S. Pat. No. 9,676,791, which is a Continuation of U.S. patent application Ser. No. 12/249,421, filed Oct. 10, 2008, now U.S. Pat. No. 8,278,314, which is a Divisional of U.S. patent application Ser. No. 10/914,974, filed Aug. 10, 2004, now U.S. Pat. No. 7,452,895 which is a Continuation-in-Part application of U.S. patent application Ser. No. 10/642,440, filed on Aug. 14, 2003, now U.S. Pat. No. 7,501,427 and claims the benefit of priority from U.S. Provisional Application No. 60/551,718, filed on Mar. 10, 2004, each of which is incorporated herein by reference in its entirety.

BACKGROUND OF THE INVENTION

1. Field of the Invention

This invention relates to novel inhibitors of type I receptor tyrosine kinases and related kinases, pharmaceutical compositions containing the inhibitors, and methods for preparing these inhibitors. The inhibitors are useful for the treatment of hyperproliferative diseases, such as cancer and inflammation, in mammals and especially in humans.

2. Description of the State of the Art

The type I receptor tyrosine kinase family consists of four closely related receptors: EGFR (ErbB1 or HER1), ErbB2 (HER2), ErbB3 (HER), and ErbB4 (HER4) (Reviewed in Riese and Stern, *Bioessays* (1998) 20:41-48, Olayioye et al., *EMBO Journal* (2000) 19:3159-3167 and Schlessinger, *Cell* (2002) 110:669-672). These are single pass transmembrane glycoprotein receptors containing an extracellular ligand binding region and an intracellular signaling domain. In addition, all receptors contain an intracellular active tyrosine kinase domain with the exception of ErbB3 whose kinase domain does not exhibit enzymatic activity. These receptors transmit extracellular signals through the cytosol to the nucleus upon activation. The activation process is initiated by ligand binding to the extracellular domain of the receptor by one of a number of different hormones. Upon ligand binding, homo- or heterodimerization is induced which results in the activation of the tyrosine kinase domains and phosphorylation of tyrosines on the intracellular signaling domains. Since no known ligand for ErbB2 has been described and ErbB3 lacks an active kinase domain, these receptors must heterodimerize to elicit a response. The phosphotyrosines then recruit the necessary cofactors to initiate several different signaling cascades including the ras/raf/MEK/MAPK and PI3K/AKT pathways. The precise signal elicited will depend on what ligands are present since the intracellular signaling domains differ as to what pathways are activated. These signaling pathways lead to both cell proliferation and cell survival through inhibition of apoptosis.

Several investigators have demonstrated the role of EGFR and ErbB2 in development and cancer (Reviewed in Salomon, et al., *Crit. Rev. Oncol. Hematol.* (1995) 19:183-232, Klapper, et al., *Adv. Cancer Res.* (2000) 77, 25-79 and Hynes and Stern, *Biochim. Biophys. Acta* (1994) 1198:165-184). Squamous carcinomas of the head and neck, and lung express high levels of EGFR. Also, constitutively active EGFR has been found in gliomas, breast cancer and lung cancer. ErbB2 overexpression occurs in approximately 30% of all breast cancer. It has also been implicated in other human cancers including colon, ovary, bladder, stomach, esophagus, lung, uterus and prostate. ErbB2 overexpression has also been correlated with poor prognosis in human cancer, including metastasis, and early relapse.

The type I tyrosine kinase receptor family have been an active area of anti-cancer research (Reviewed in Mendelsohn and Baselga, *Oncogene* (2000) 19:6550-6565 and Normanno et al., *Endocrine-Related Cancer* (2003) 10:1-21). Several inhibitors of the EGFR and the ErbB2 signaling pathway have demonstrated clinical efficacy in cancer treatment. Herceptin, a humanized version of anti-ErbB2 monoclonal antibody, was approved for use in breast cancer in the United States in 1998. Iressa and Tarceva are small molecule inhibitors of EGFR that are expected to be commercially available. In addition, several other antibodies and small molecules that target the interruption of the type I tyrosine kinase receptor signaling pathways are in clinical and pre-clinical development. For example, IMC-225, which is a humanized antibody against the extracellular domain of EGFR demonstrated efficacy and will likely be approved.

SUMMARY OF THE INVENTION

This invention provides compounds, methods to produce these compounds, and pharmaceutical compositions containing the compounds that inhibit type I receptor tyrosine kinases. Such compounds, generally referred to as quinazoline analogs, have utility as therapeutic agents for diseases that can be treated by the inhibition of type I receptor tyrosine kinases. They may also act as inhibitors of serine, threonine, and dual specificity kinases inhibitors. In general, the invention relates to quinazoline derivatives of general Formula I:

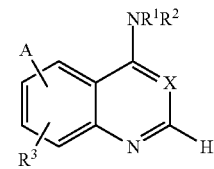

wherein A is bonded to at least one of the carbons at positions 5, 6, 7 or 8 of the bicyclic ring and wherein the bicyclic ring is substituted by zero, one or two independent $R^3$ groups;

X is N, CH, CF or C—CN;

A is Q or Z;

Q is

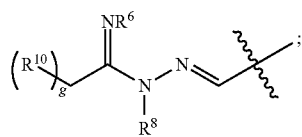

$R^1$ is a substituted or unsubstituted, monocyclic or bicyclic, aryl or heteroaryl moiety;

$R^2$ is H or a substituted or unsubstituted $C_{1-8}$ alkyl, allyl, substituted benzyl;

$R^3$ is hydrogen, halogen, cyano, nitro, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl, partially unsaturated heterocylyl, heterocyclyl alkyl, —$NR^4SO_2R^5$—$SO_2NR^6R^4$, —$C(O)R^6$, —$C(O)OR^6$, —$OC(O)R^6$, —$NR^4C(O)OR^5$, —$NR^4C(O)R^6$, —$C(O)NR^4R^6$, —$NR^4R^6$, —$NR^4C(O)NR^4R^6$, —$OR^6$, —$S(O)R^5$, —$SO_2R^5$, or $SR^6$, wherein said alkyl, alkenyl, alkynyl, cycloalkyl, cycloalkylalkyl, aryl, arylalkyl, heteroaryl, heteroarylalkyl, heterocyclyl, partially unsaturated heterocylyl, and heterocyclylalkyl is optionally substituted with one to five groups independently selected from the group consisting of oxo, halogen, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, cyano, nitro, trifluoromethyl, difluoromethoxy, trifluoromethoxy, azido, —$NR^4SO_2R^5$, —$SO_2NR^6R^4$, —$C(O)R^6$, —$C(O)OR^6$, —$OC(O)R^6$, —$NR^4C(O)OR^5$, —$NR^4C(O)CR^6$, —$C(O)NR^4R^6$, —$NR^4R^6$, —$NR^4C(O)NR^4R^6$, —$NR^4C(NCN)NR^4R^6$, —$OR^6$, —$S(O)R^5$, —$SO_2R^5$, aryl, arylalkyl, heteroaryl, heteroarylalkyl, heterocyclyl, and heterocyclylalkyl;

$R^{10}$ is hydrogen, halogen, cyano, nitro, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl, heterocyclylalkyl, partially unsaturated heterocyclyl —$NR^4SO_2R^5$—$SO_2NR^6R^4$, —$C(O)R^6$, —$C(O)OR^6$, —$OC(O)R^6$, —$NR^4C(O)OR^5$, —$NR^4C(O)R^6$, —$C(O)NR^4R^6$, —$NR^4R^6$, —$NR^4C(O)NR^4R^6$, —$OR^6$, —$S(O)R^5$, —$SO_2R^5$, or $SR^6$, wherein said alkyl, alkenyl, alkynyl, cycloalkyl, aryl, heteroaryl, heterocyclyl, or partially unsaturated heterocyclyl is optionally substituted with one to five groups independently selected from the group consisting of oxo, halogen, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, cyano, nitro, trifluoromethyl, difluoromethoxy, trifluoromethoxy, azido, —$NR^4SO_2R^5$, —$SO_2NR^6R^4$, —$C(O)R^6$, —$C(O)OR^6$, —$OC(O)R^6$, —$NR^4C(O)OR^5$, $NR^4C(O)CR^6$, —$C(O)NR^4R^6$, —$NR^4R^6$, —$NR^4C(O)NR^4R^6$, —$NR^4C(NCN)NR^4R^6$, —$OR^6$, —$S(O)R^5$, —$SO_2R^5$, aryl, arylalkyl, heteroaryl, heteroarylalkyl, heterocyclyl, and heterocyclylalkyl, wherein g is 1 to 3 and each $R^{10}$ can be the same or different;

or one or more of said $R^{10}$ groups may be independently joined together with the atoms to which they are attached to complete a 3 to 10 membered cycloalkyl ring or heterocloalkyl ring optionally containing one or more additional heteroatoms selected from the group consisting of O, S, SO, $SO_2$ and $NR^6$, where each ring carbon is optionally substituted with one to three groups independently selected from the group consisting of halogen, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, cyano, nitro, trifluoromethyl, difluoromethoxy, trifluoromethoxy, azido, aryl, $OR^8$, $NR^6R^8$, $SR^6$, heteroaryl, arylalkyl, heteroarylalkyl, heterocyclyl, and heterocyclylalkyl, provided said ring does not contain two adjacent O or two adjacent S atoms;

Z is

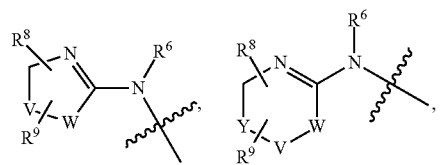

wherein when $R^6$=H then Z further includes

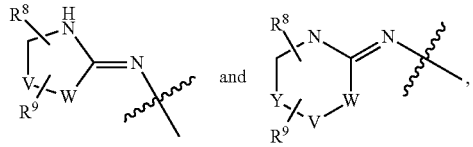

and wherein Z includes one or more $R^8$ or $R^9$ groups, wherein said $R^8$ and $R^9$ groups may be bonded to the same or different atoms;

W and V are independently selected from the group consisting of $CR^7R^8$, $CR^8R^9$, O, $NR^6$, S, SO, and $SO_2$;

Y is selected from the group consisting of S, SO, $SO_2$, $CR^7CR^8$, and $CR^8R^9$, provided that when W is O, $NR^6$, S, SO, or $SO_2$, then V is $CR^8R^9$, and
when V is O, $NR^6$, S, SO, or $SO_2$, then W and Y are each $CR^8R^9$;

$R^4$ is H or $C_{1-6}$ alkyl;

$R^5$ is trifluoromethyl, $C_1$-$C_{10}$ alkyl, $C_3$-$C_{10}$ cycloalkyl, aryl, arylalkyl, heteroaryl, heteroarylalkyl, heterocyclyl, heterocyclylalkyl, or partially unsaturated heterocycle, wherein said alkyl, cycloalkyl, aryl, arylalkyl, heteroaryl, heteroarylalkyl, heterocyclyl, partially unsaturated heterocyclyl, and heterocyclylalkyl is optionally substituted with one to five groups independently selected from the group consisting of oxo, halogen, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, cyano, nitro, $OR^6$, $NR^4R^6$, $SR^6$, trifluoromethyl, difluoromethoxy, trifluoromethoxy, azido, aryl, heteroaryl, arylalkyl, heteroarylalkyl, heterocyclyl, and heterocyclylalkyl;

$R^6$, $R^8$ and $R^9$ are independently selected from the group consisting of hydrogen, trifluoromethyl, $C_1$-$C_{10}$ alkyl, $(CH_2)_{0-4}C_3$-$C_{10}$ cycloalkyl, aryl, arylalkyl, heteroaryl, heteroarylalkyl, heterocyclyl, partially unsaturated heterocyclyl and heterocyclylalkyl, wherein said alkyl, cycloalkyl, aryl, arylalkyl, heteroaryl, heterocyclyl, partially unsaturated heterocyclyl, and heterocyclylalkyl is optionally substituted with one to five groups independently selected from the group consisting of oxo, halogen, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, cyano, nitro, $OR^6$, $NR^6R^8$, $SR^6$, trifluoromethyl, difluoromethoxy, trifluoromethoxy, azido, aryl, heteroaryl, arylalkyl, heteroarylalkyl, heterocyclyl, partially unsaturated heterocyclyl and heterocyclylalkyl;

$R^7$ is hydrogen, halogen, cyano, nitro, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl, heterocyclylalkyl, partially unsaturated heterocycle, —$NR^4SO_2R^5$—$SO_2NR^6R^4$, —$C(O)R^6$, —$C(O)OR^6$, —$OC(O)R^6$, —$NR^4C(O)OR^5$, —$NR^4C(O)R^6$, —$C(O)NR^4R^6$, —$NR^4R^6$, —$NR^4C(O)NR^4R^6$, —$OR^6$, —$S(O)R^5$, or $SR^6$, wherein said alkyl, alkenyl, alkynyl, cycloalkyl, aryl, heteroaryl heterocyclyl, and partially unsaturated heterocyclyl is optionally substituted with one to five groups independently selected from the group consisting of oxo, halogen, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, cyano, nitro, trifluoromethyl, difluoromethoxy, trifluoromethoxy, azido, —$NR^4$ $SO_2R^5$, —$SO_2NR^6R^4$, —$C(O)R^6$, —$C(O)OR^6$, —$OC(O)R^6$, —$NR^4C(O)OR^5$, —$NR^4C(O)CR^6$, —$C(O)NR^4R^6$, —$NR^4R^6$, —$NR^4C(O)NR^4R^6$, —$NR^4C(NCN)NR^4R^6$, —$OR^6$, —$S(O)R^5$, —$SO_2R^5$, aryl, arylalkyl, heteroaryl, heteroarylalkyl, heterocyclyl, partially unsaturated heterocyclyl and heterocyclylalkyl;

or $R^4$ and $R^6$ together with the atoms to which they are attached may be independently joined to complete a 3 to 10 membered cycloalkyl ring or heterocycloalkyl ring optionally containing one or more additional heteroatoms selected from the group consisting of O, S, SO, $SO_2$ and $NR^6$, wherein each ring carbon is optionally substituted with one to three groups independently selected from the group consisting of halogen, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, cyano, nitro, trifluoromethyl, difluoromethoxy, trifluoromethoxy, azido, aryl, $OR^8$, $NR^6R^8$, $SR^6$, heteroaryl, arylalkyl, heteroarylalkyl, heterocyclyl, partially unsaturated heterocyclyl and heterocyclylalkyl, provided said ring does not contain two adjacent O or two adjacent S atoms;

or $R^6$ and $R^8$ together with the atoms to which they are attached may be independently joined to complete a 3 to 10 membered cycloalkyl ring or heterocycloalkyl ring optionally containing one or more additional heteroatoms selected from the group consisting of O, S, SO, $SO_2$ and $NR^6$, wherein each ring carbon is optionally substituted with one to three groups independently selected from the group consisting of halogen, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, cyano, nitro, trifluoromethyl, difluoromethoxy, trifluoromethoxy, azido, aryl, $OR^8$, $NR^6R^8$, $SR^6$, heteroaryl, arylalkyl, heteroarylalkyl, heterocyclyl, partially unsaturated heterocyclyl and heterocyclylalkyl, provided said ring does not contain two adjacent O or two adjacent S atoms;

or $R^7$ and $R^8$ together with the atoms to which they are attached may be independently joined to complete a 3 to 10 membered cycloalkyl ring or heterocycloalkyl ring optionally containing one or more additional heteroatoms selected from the group consisting of O, S, SO, $SO_2$ and $NR^6$, wherein each ring carbon is optionally substituted with one to three groups independently selected from the group consisting of halogen, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, cyano, nitro, trifluoromethyl, difluoromethoxy, trifluoromethoxy, azido, aryl, $OR^8$, $NR^6R^8$, $SR^6$, heteroaryl, arylalkyl, heteroarylalkyl, heterocyclyl, partially unsaturated heterocyclyl and heterocyclylalkyl; provided said ring does not contain two adjacent O or two adjacent S atoms;

or $R^8$ and $R^9$ together with the atoms to which they are attached may be independently joined to complete a 3 to 10 membered cycloalkyl ring or heterocycloalkyl ring optionally containing one or more additional heteroatoms selected from the group consisting of O, S, SO, $SO_2$ and $NR^6$, wherein each ring carbon may be optionally substituted with one to three groups independently selected from the group consisting of halogen, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, cyano, nitro, trifluoromethyl, difluoromethoxy, trifluoromethoxy, azido, aryl, $OR^8$, $NR^6R^8$, $SR^6$, heteroaryl, arylalkyl, heteroarylalkyl, heterocyclyl, partially unsaturated heterocyclyl and heterocyclylalkyl, provided said ring does not contain two adjacent 0 or two adjacent S atoms;

or $R^6$ and $R^{10}$ together with the atoms to which they are attached may be independently joined to complete a 3 to 10 membered cycloalkyl ring or heterocycloalkyl ring optionally containing one or more additional heteroatoms selected from the group consisting of O, S, SO, $SO_2$ and $NR^6$, wherein each ring carbon may be optionally substituted with one to three groups independently selected from the group consisting of halogen, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, cyano, nitro, trifluoromethyl, difluoromethoxy, trifluoromethoxy, azido, aryl, $OR^8$, $NR^6R^8$, $SR^6$, heteroaryl, arylalkyl, heteroarylalkyl, heterocyclyl, partially unsaturated heterocyclyl and heterocyclylalkyl, provided said ring does not contain two adjacent O or two adjacent S atoms;

or $R^8$ and $R^{10}$ together with the atoms to which they are attached may be independently joined to complete a 3 to 10 membered cycloalkyl ring or heterocycloalkyl ring optionally containing one or more additional heteroatoms selected from the group consisting of O, S, SO, $SO_2$ and $NR^6$, wherein each ring carbon may be optionally substituted with one to three groups independently selected from halogen, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, cyano, nitro, trifluoromethyl, difluoromethoxy, trifluoromethoxy, azido, aryl, $OR^8$, $NR^6R^8$, $SR^6$, heteroaryl, arylalkyl, heteroarylalkyl, heterocyclyl, partially unsaturated heterocyclyl and heterocyclylalkyl, provided said ring does not contain two adjacent O or two adjacent S atoms.

The invention may also be directed to pharmaceutically acceptable prodrugs, pharmaceutically active metabolites, and pharmaceutically acceptable salts of the compound of general Formula I. Methods of making the compounds of Formula I are also described.

In a further aspect, the present invention provides compounds that inhibit the activity of type I receptor tyrosine kinases such as EGFR, ErbB2, ErbB3, ErbB4, VEGFR2, Flt3 and FGFR, comprising compounds of Formula I.

In a further aspect, the present invention provides a method of treating diseases or medical conditions mediated by type I receptor tyrosine kinases which comprises administering to a warm-blooded animal an effective amount of a compound of Formula I, or a pharmaceutically acceptable salt or in vivo cleavable prodrug thereof.

In a further aspect, the present invention provides a method of inhibiting the production of type I receptor kinases which comprises administering to a warm-blooded animal an effective amount of a compound of Formula I, or a pharmaceutically acceptable salt or in vivo cleavable prodrug thereof.

In a further aspect, the present invention provides a method of providing type I receptor kinase inhibitory effect comprising administering to a warm-blooded animal an effective amount of a compound of Formula I, or a pharmaceutically acceptable salt or in vivo cleavable prodrug thereof.

In a further aspect, the present invention provides treating or preventing a type I receptor kinase mediated condition, comprising administering an amount of a compound effective to treat or prevent said type I receptor kinase-mediated condition or a pharmaceutical composition comprising said compound, to a human or animal in need thereof, wherein said compound is a compound of Formula I, or a pharmaceutically-acceptable salt or in vivo cleavable prodrug thereof. The type I receptor kinase mediated condition that can be treated according to the methods of this invention includes hyperproliferative disorders, such as cancer of the head and neck, lung, breast, colon, ovary, bladder, stomach, kidney, skin, pancreas, leukemias, lymphomas, esophagus, uterus or prostate, among other kinds of hyperproliferative disorders.

The compounds of Formula I may be used advantageously in combination with other known therapeutic agents.

The invention also relates to pharmaceutical compositions comprising an effective amount of an agent selected from compounds of Formula I or a pharmaceutically acceptable prodrug, pharmaceutically active metabolite, or pharmaceutically acceptable salt thereof.

Additional advantages and novel features of this invention shall be set forth in part in the description that follows, and in part will become apparent to those skilled in the art upon examination of the following specification or may be learned by the practice of the invention. The advantages of the invention may be realized and attained by means of the instrumentalities, combinations, compositions, and methods particularly pointed out in the appended claims.

BRIEF DESCRIPTION OF THE FIGURES

The accompanying drawings, which are incorporated herein and form a part of the specification, illustrate non-limiting embodiments of the present invention, and together with the description, serve to explain the principles of the invention.

DESCRIPTION OF THE DRAWINGS

Figure 1:
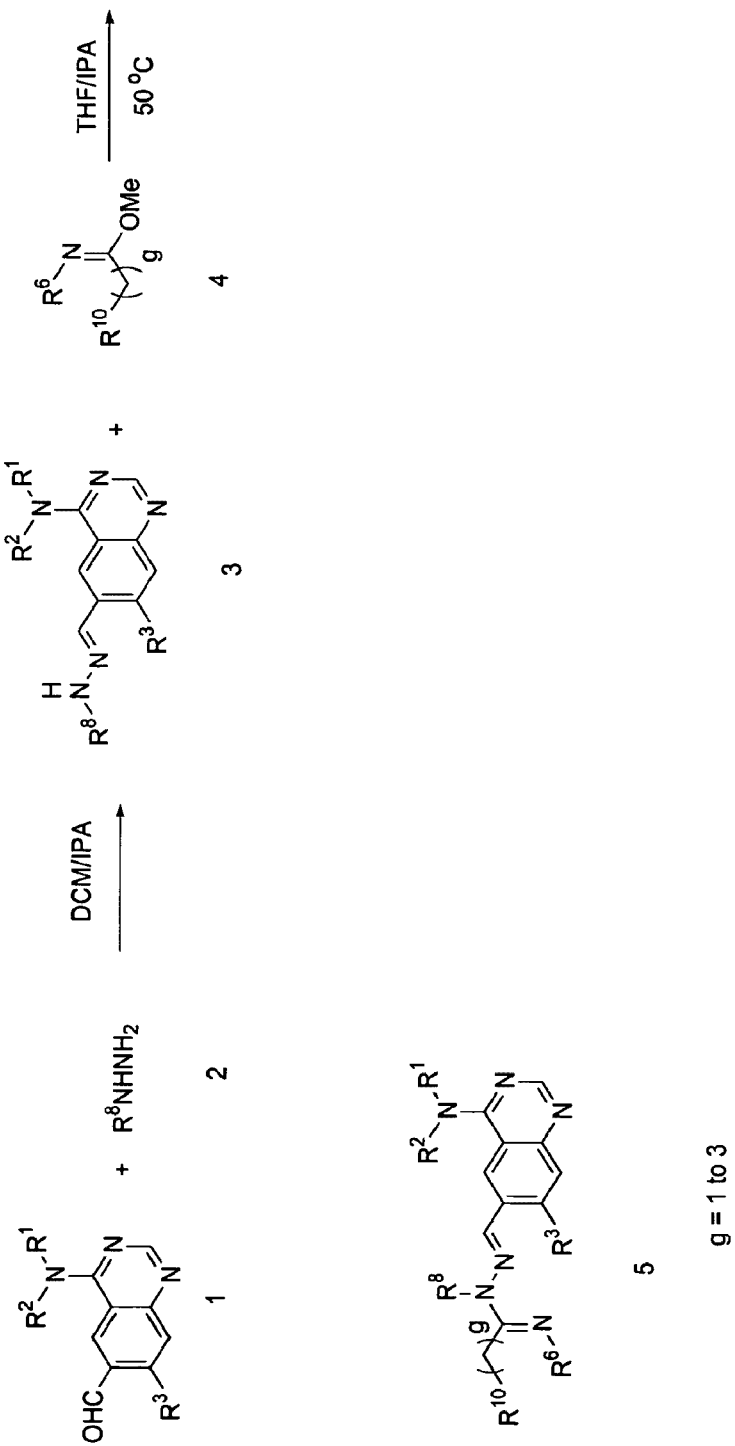

FIG. 1 shows a reaction scheme for the preparation of imino amidines.

Figure 2:
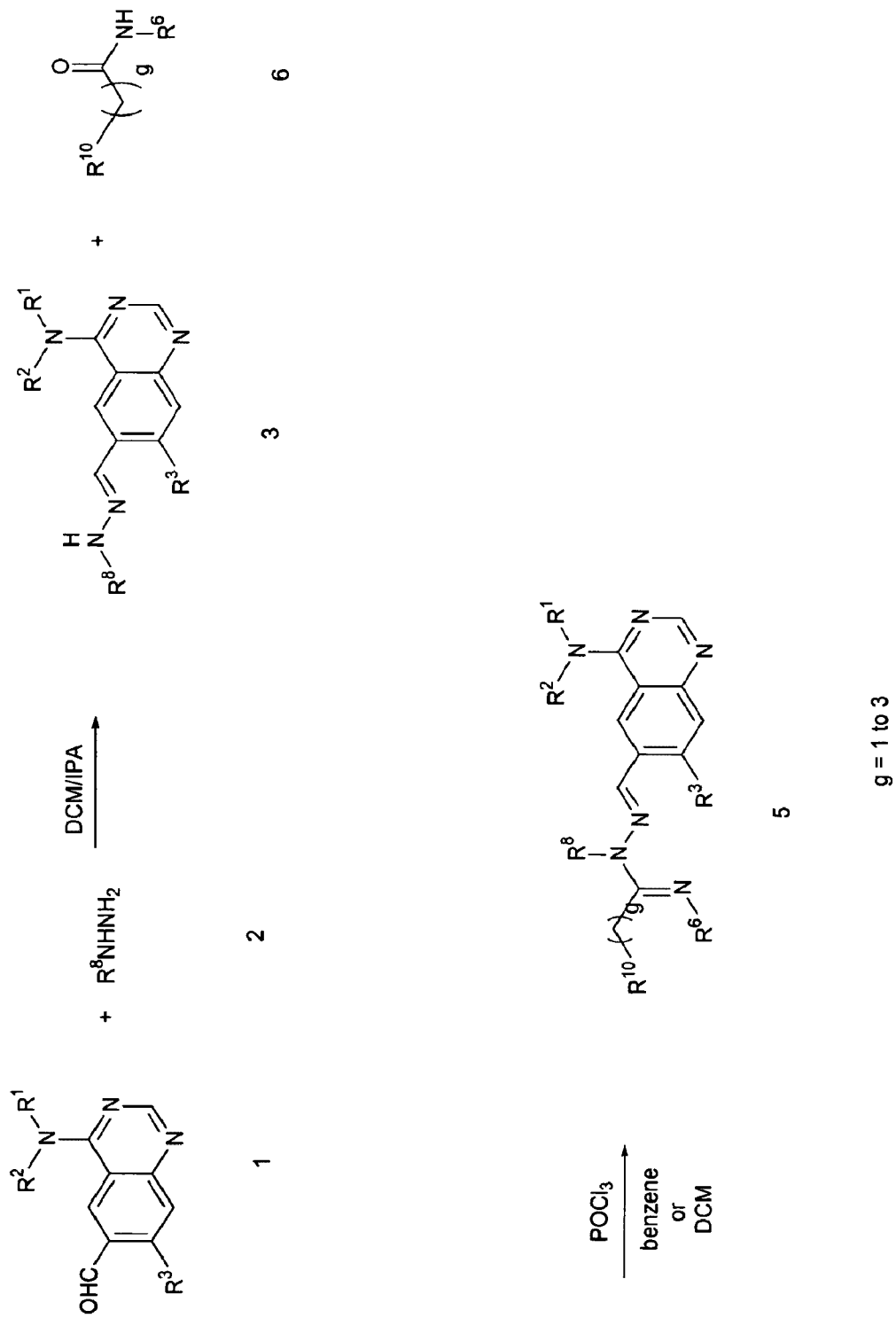

FIG. 2 shows another reaction scheme for the preparation of imino amidines.

Figure 3:
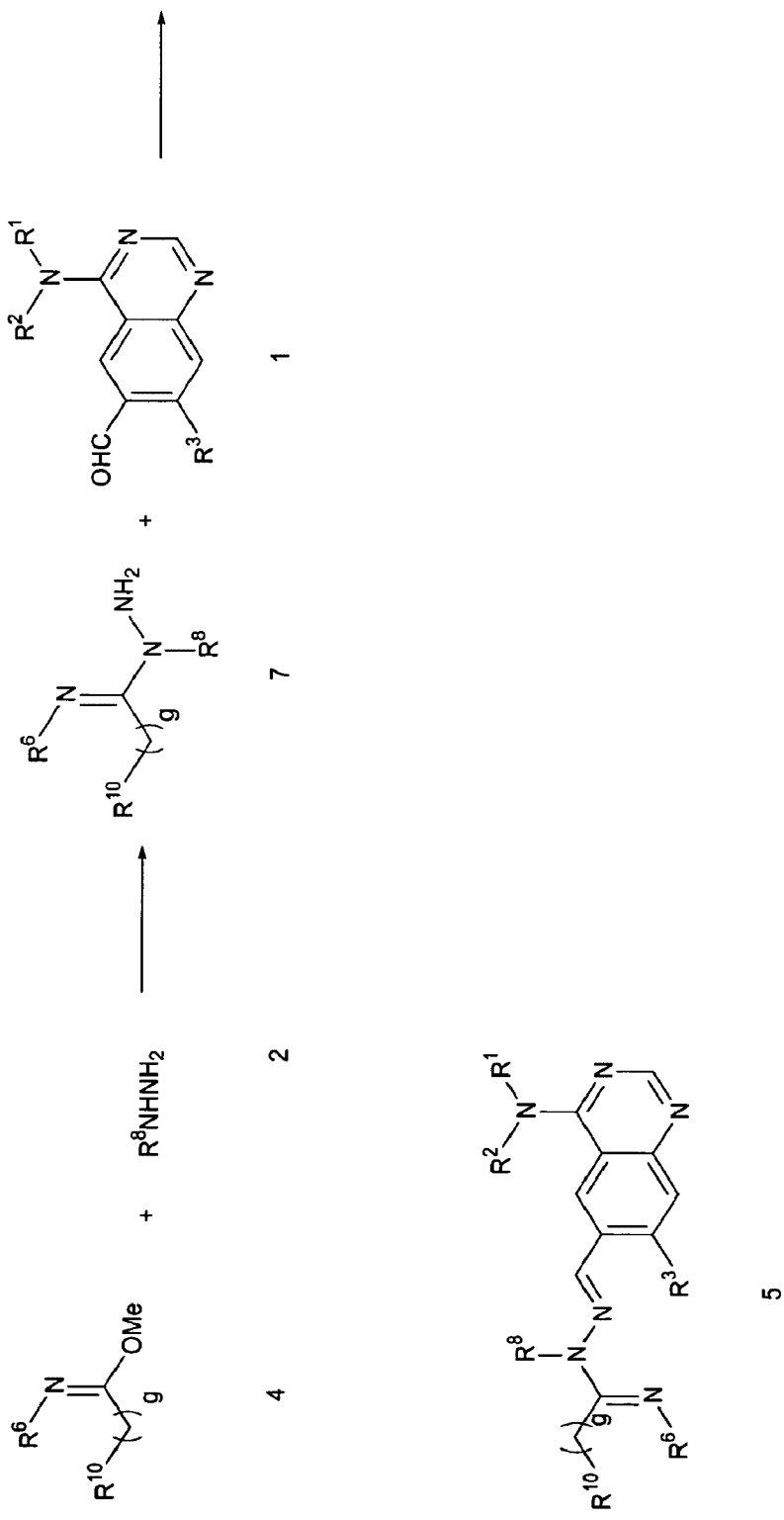

FIG. 3 shows another reaction scheme for the preparation of imino amidines.

Figure 4:
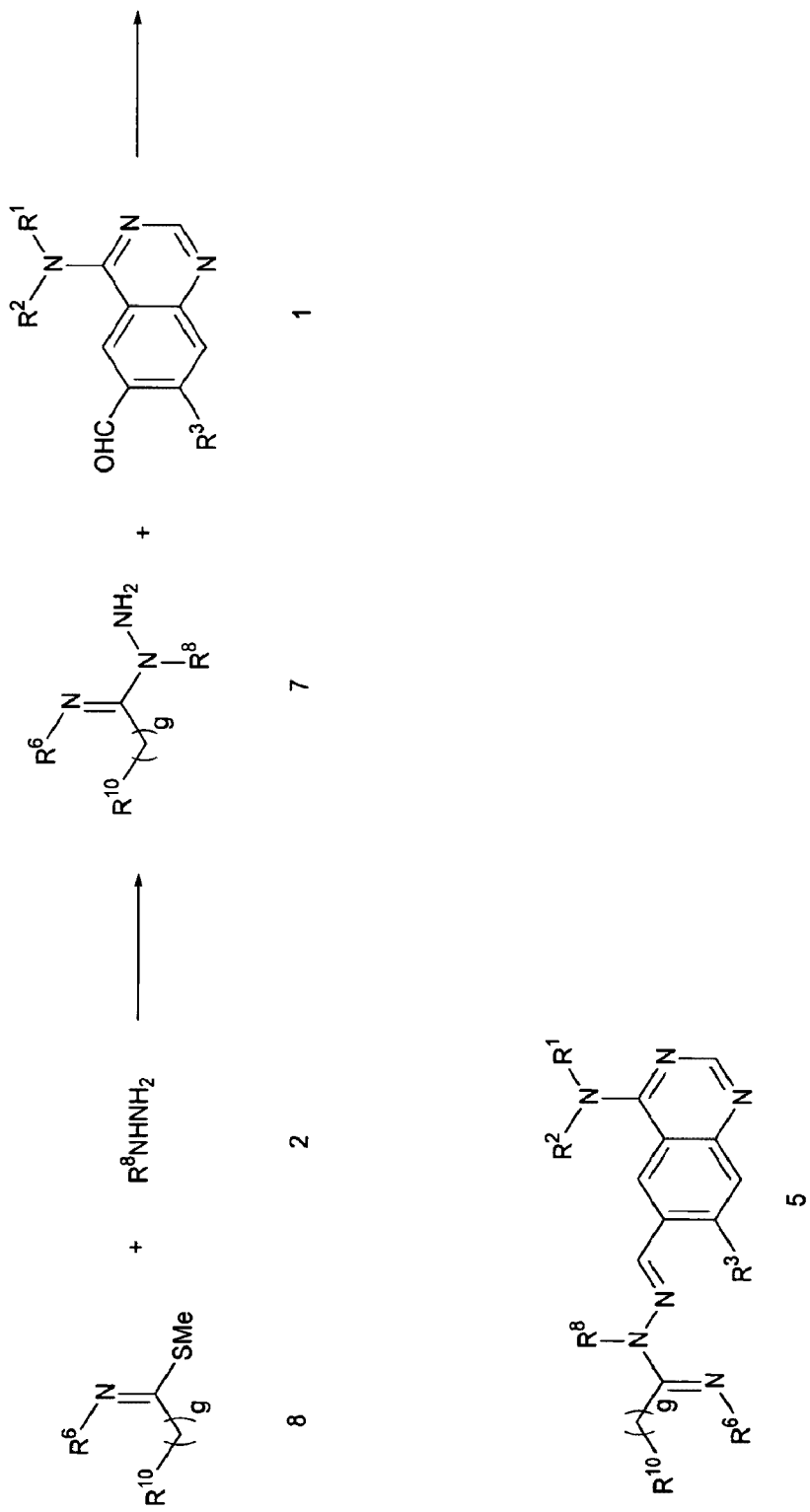

FIG. 4 shows another reaction scheme for the preparation of imino amidines.

Figure 5:
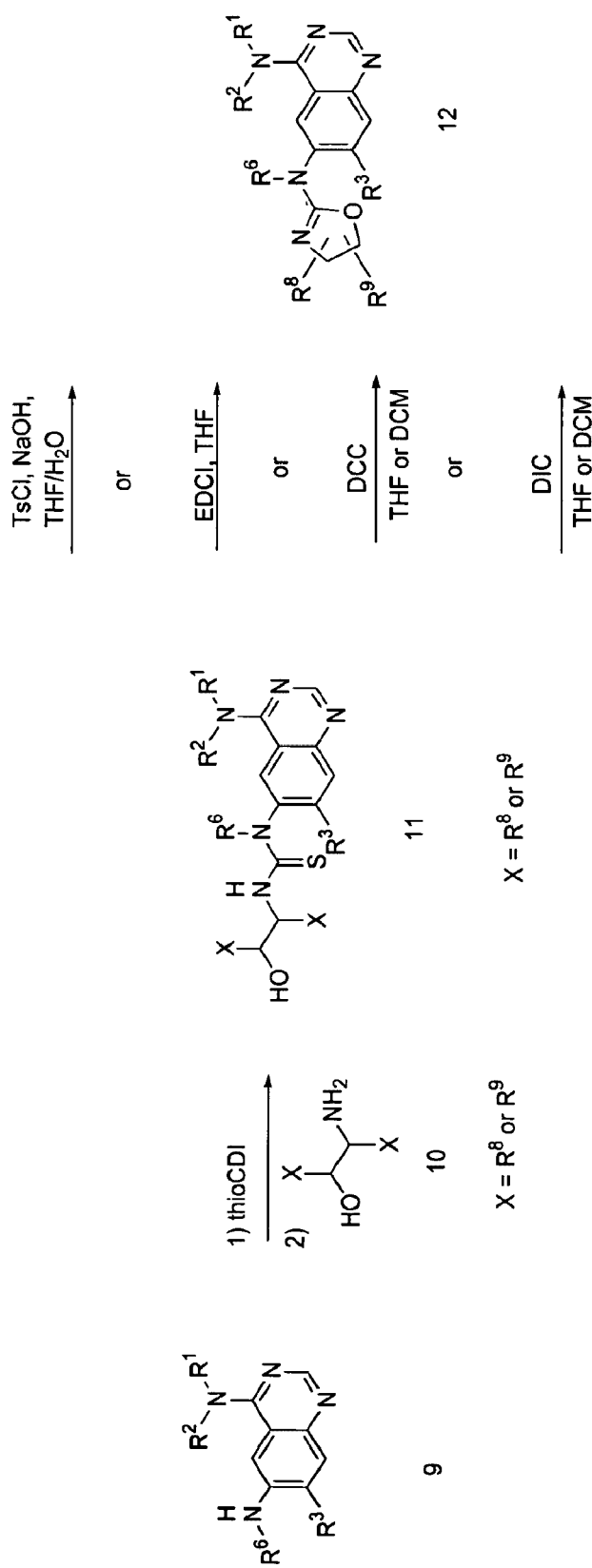

FIG. 5 shows a reaction scheme for the preparation of oxazolines.

Figure 6:
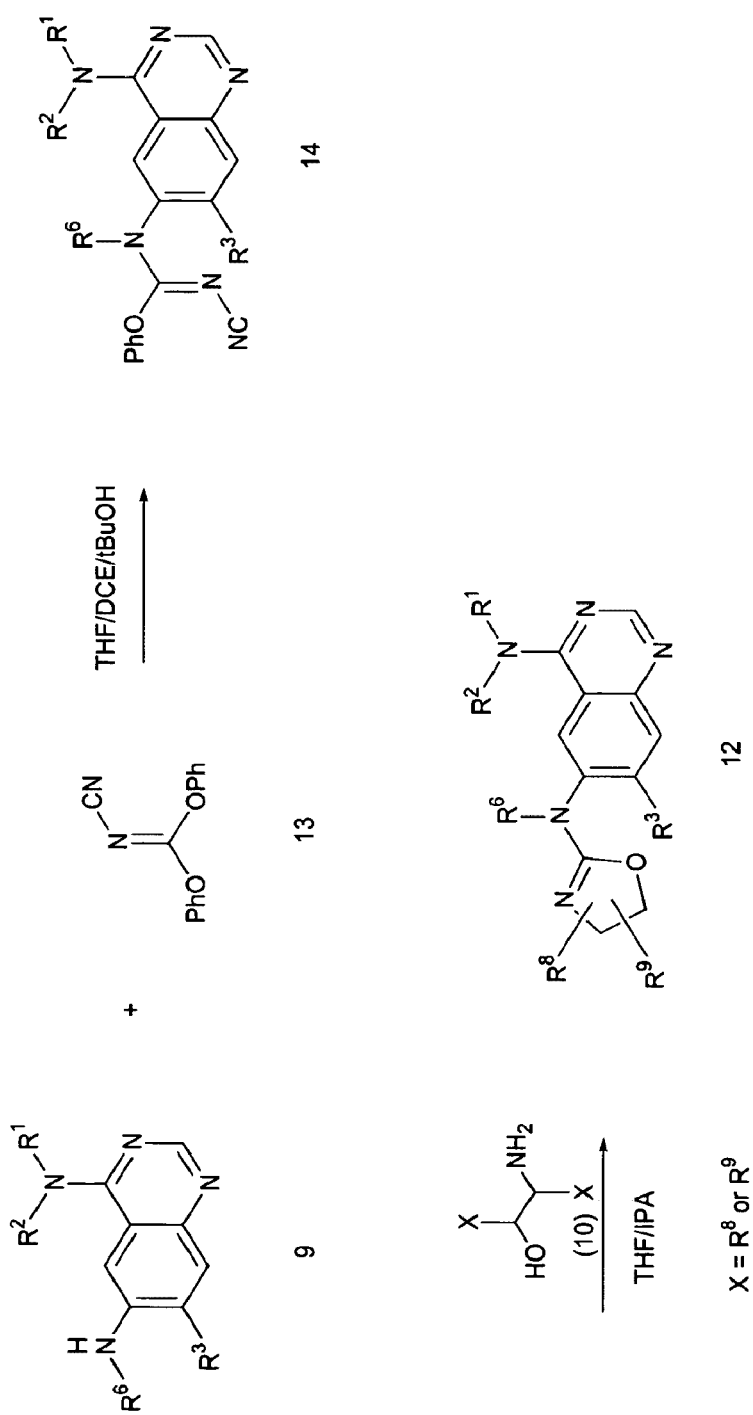

FIG. 6 shows another reaction scheme for the preparation of oxazolines.

DETAILED DESCRIPTION OF THE INVENTION

The inventive compounds of Formula I are useful for inhibiting type I receptor tyrosine kinases, such as EGFR (HER1), ErbB2 (HER2), ErbB3 (HER3), ErbB4 (HER4), VEGFR2, Flt3 and FGFR. The compounds of Formula I may also be useful as inhibitors of serine, threonine, and dual specificity kinases such as Raf, MEK, and p38. Such compounds have utility as therapeutic agents for diseases that can be treated by the inhibition of the type I receptor tyrosine kinases signaling pathway and serine, threonine, and dual specificity kinase pathways. In general, the invention relates to compounds of the general Formula I:

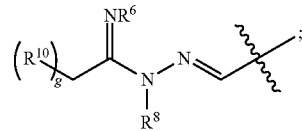

wherein A is bonded to at least one of the carbons at positions 5, 6, 7 or 8 of the bicyclic ring and wherein the bicyclic ring is substituted by zero, one or two independent $R^3$ groups;

X is N, CH, CF or C—CN;
A is Q or Z;
Q is

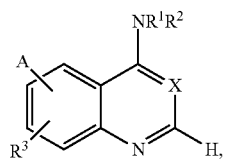

$R^1$ is a substituted or unsubstituted, monocyclic or bicyclic, aryl or heteroaryl moiety;

$R^2$ is H or a substituted or unsubstituted $C_{1-8}$ alkyl;

$R^3$ is hydrogen, halogen, cyano, nitro, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl, partially unsaturated heterocylyl, heterocyclyl alkyl, —NR$^4$SO$_2$R$^5$—SO$_2$NR$^6$R$^4$, —C(O)R$^6$, —C(O)OR$^6$, —OC(O)R$^6$, —NR$^4$C(O)OR$^5$, —NR$^4$C(O)R$^6$, —C(O)NR$^4$R$^6$, —NR$^4$R$^6$, —NR$^4$C(O)NR$^4$R$^6$, —OR$^6$, —S(O)R$^5$, —SO$_2$R$^5$, or SR$^6$, wherein said alkyl, alkenyl, alkynyl, cycloalkyl, cycloalkylalkyl, aryl, arylalkyl, heteroaryl, heteroarylalkyl, heterocyclyl, partially unsaturated heterocylyl, and heterocyclylalkyl is optionally substituted with one to five groups independently selected from the group consisting of oxo, halogen, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, cyano, nitro, trifluoromethyl, difluoromethoxy, trifluoromethoxy, azido, —NR$^4$SO$_2$R$^5$, —SO$_2$NR$^6$R$^4$, —C(O)R$^6$, —C(O)OR$^6$, —OC(O)R$^6$, —NR$^4$C(O)OR$^5$, —NR$^4$C(O)CR$^6$, —C(O)NR$^4$R$^6$, —NR$^4$R$^6$, —NR$^4$C(O)NR$^4$R$^6$, —NR$^4$C(NCN)NR$^4$R$^6$, —OR$^6$, —S(O)R$^5$, —SO$_2$R$^5$, aryl, arylalkyl, heteroaryl, heteroarylalkyl, heterocyclyl, and heterocyclylalkyl;

$R^{10}$ is hydrogen, halogen, cyano, nitro, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl, heterocyclylalkyl, partially unsaturated heterocyclyl —NR$^4$SO$_2$R$^5$—SO$_2$NR$^6$R$^4$, —C(O)R$^6$, —C(O)OR$^6$, —OC(O)R$^6$, —NR$^4$C(O)OR$^5$, —NR$^4$C(O)R$^6$, —C(O)NR$^4$R$^6$, —NR$^4$R$^6$, —NR$^4$C(O)NR$^4$R$^6$, —OR$^6$, —S(O)R$^5$, —SO$_2$R$^5$, or SR$^6$, wherein said alkyl, alkenyl, alkynyl, cycloalkyl, aryl, heteroaryl, heterocyclyl, or partially unsaturated heterocyclyl is optionally substituted with one to five groups independently selected from the group consisting of oxo, halogen, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, cyano, nitro, trifluoromethyl, difluoromethoxy, trifluoromethoxy, azido, —NR$^4$SO$_2$R$^5$, —SO$_2$NR$^6$R$^4$, —C(O)R$^6$, —C(O)OR$^6$, —OC(O)R$^6$, —NR$^4$C(O)OR$^5$, —NR$^4$C(O)CR$^6$, —C(O)NR$^4$R$^6$, —NR$^4$R$^6$, —NR$^4$C(O)NR$^4$R$^6$, —NR$^4$C(NCN)NR$^4$R$^6$, —OR$^6$, —S(O)R$^5$, —SO$_2$R$^5$, aryl, arylalkyl, heteroaryl, heteroarylalkyl, heterocyclyl, and heterocyclylalkyl, wherein g is 1 to 3 and each $R^{10}$ can be the same or different;

or one or more of said $R^{10}$ groups may be independently joined together with the atoms to which they are attached to complete a 3 to 10 membered cycloalkyl ring or heterocycloalkyl ring optionally containing one or more additional heteroatoms selected from the group consisting of O, S, SO, SO$_2$ and NR$^6$, where each ring carbon is optionally substituted with one to three groups independently selected from the group consisting of halogen, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, cyano, nitro, trifluoromethyl, difluoromethoxy, trifluoromethoxy, azido, aryl, $OR^8$, $NR^6R^8$, $SR^6$, heteroaryl, arylalkyl, heteroarylalkyl, heterocyclyl, and heterocyclylalkyl, provided said ring does not contain two adjacent O or two adjacent S atoms;

Z is

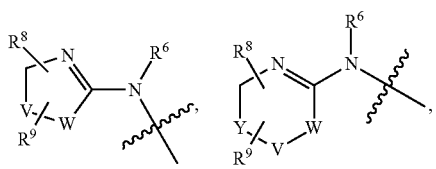

wherein when $R^6$=H then Z further includes

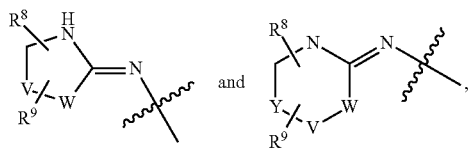

and wherein Z includes one or more $R^8$ or $R^9$ groups, wherein said $R^8$ and $R^9$ groups may be bonded to the same or different atoms;

W and V are independently selected from the group consisting of $CR^7CR^8$, $CR^8R^9$, O, $NR^6$, S, SO, and $SO_2$, and Y is selected from the group consisting of S, SO, $SO_2$, $CR^7CR^8$, and $CR^8R^9$, provided that when W is O, $NR^6$, S, SO, or $SO_2$, then V is $CR^8R^9$, and
when V is O, $NR^6$, S, SO, or $SO_2$, then W and Y are each $CR^8R^9$;

$R^4$ is H or $C_{1-6}$ alkyl;

$R^5$ is trifluoromethyl, $C_1$-$C_{10}$ alkyl, $C_3$-$C_{10}$ cycloalkyl, aryl, arylalkyl, heteroaryl, heteroarylalkyl, heterocyclyl, heterocyclylalkyl, or partially unsaturated heterocycle, wherein said alkyl, cycloalkyl, aryl, arylalkyl, heteroaryl, heteroarylalkyl, heterocyclyl, partially unsaturated heterocyclyl, and heterocyclylalkyl is optionally substituted with one to five groups independently selected from the group consisting of oxo, halogen, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, cyano, nitro, $OR^6$, $NR^4R^6$, $SR^6$, trifluoromethyl, difluoromethoxy, trifluoromethoxy, azido, aryl, heteroaryl, arylalkyl, heteroarylalkyl, heterocyclyl, and heterocyclylalkyl;

$R^6$, $R^8$ and $R^9$ are independently selected from the group consisting of hydrogen, trifluoromethyl, $C_1$-$C_{10}$ alkyl, $(CH_2)_{0-4}C_3$-$C_{10}$ cycloalkyl, aryl, arylalkyl, heteroaryl, heteroarylalkyl, heterocyclyl, partially unsaturated heterocyclyl and heterocyclylalkyl, wherein said alkyl, cycloalkyl, aryl, arylalkyl, heteroaryl, heterocyclyl, partially unsaturated heterocyclyl, and heterocyclylalkyl is optionally substituted with one to five groups independently selected from the group consisting of oxo, halogen, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, cyano, nitro, $OR^6$, $NR^6R^8$, $SR^6$, trifluoromethyl, difluoromethoxy, trifluoromethoxy, azido, aryl, heteroaryl, arylalkyl, heteroarylalkyl, heterocyclyl, partially unsaturated heterocyclyl and heterocyclylalkyl;

$R^7$ is hydrogen, halogen, cyano, nitro, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl, heterocyclylalkyl, partially unsaturated heterocycle, —$NR^4SO_2R^5$—$SO_2NR^6R^4$, —$C(O)R^6$, —$C(O)OR^6$, —$OC(O)R^6$, —$NR^4C(O)OR^5$, —$NR^4C(O)R^6$, —$C(O)NR^4R^6$, —$NR^4R^6$, —$NR^4C(O)NR^4R^6$, —$OR^6$, —$S(O)R^5$, or $SR^6$, wherein said alkyl, alkenyl, alkynyl, cycloalkyl, aryl, heteroaryl heterocyclyl, and partially unsaturated heterocyclyl is optionally substituted with one to five groups independently selected from the group consisting of oxo, halogen, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, cyano, nitro, trifluoromethyl, difluoromethoxy, trifluoromethoxy, azido, —$NR^4SO_2R^5$, —$SO_2NR^6R^4$, —$C(O)R^6$, —$C(O)OR^6$, —$OC(O)R^6$, —$NR^4C(O)OR^5$, —$NR^4C(O)CR^6$, —$C(O)NR^4R^6$, —$NR^4R^6$, —$NR^4C(O)NR^4R^6$, —$OR^6$, —$S(O)R^5$, —$SO_2R^5$, aryl, arylalkyl, heteroaryl, heteroarylalkyl, heterocyclyl, partially unsaturated heterocyclyl and heterocyclylalkyl;

or $R^4$ and $R^6$ together with the atoms to which they are attached may be independently joined to complete a 3 to 10 membered cycloalkyl ring or heterocycloalkyl ring optionally containing one or more additional heteroatoms selected from the group consisting of O, S, SO, $SO_2$ and $NR^6$, wherein each ring carbon is optionally substituted with one to three groups independently selected from the group consisting of halogen, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, cyano, nitro, trifluoromethyl, difluoromethoxy, trifluoromethoxy, azido, aryl, $OR^8$, $NR^6R^8$, $SR^6$, heteroaryl, arylalkyl, heteroarylalkyl, heterocyclyl, partially unsaturated heterocyclyl and heterocyclylalkyl, provided said ring does not contain two adjacent O or two adjacent S atoms;

or $R^6$ and $R^8$ together with the atoms to which they are attached may be independently joined to complete a 3 to 10 membered cycloalkyl ring or heterocycloalkyl ring optionally containing one or more additional heteroatoms selected from the group consisting of O, S, SO, $SO_2$ and $NR^6$, wherein each ring carbon is optionally substituted with one to three groups independently selected from the group consisting of halogen, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, cyano, nitro, trifluoromethyl, difluoromethoxy, trifluoromethoxy, azido, aryl, $OR^8$, $NR^6R^8$, $SR^6$, heteroaryl, arylalkyl, heteroarylalkyl, heterocyclyl, partially unsaturated heterocyclyl and heterocyclylalkyl, provided said ring does not contain two adjacent O or two adjacent S atoms;

$R^7$ and $R^8$ together with the atoms to which they are attached may be independently joined to complete a 3 to 10 membered cycloalkyl ring or heterocycloalkyl ring optionally containing one or more additional heteroatoms selected from the group consisting of O, S, SO, $SO_2$ and $NR^6$, wherein each ring carbon is optionally substituted with one to three groups independently selected from the group consisting of halogen, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, cyano, nitro, trifluoromethyl, difluoromethoxy, trifluoromethoxy, azido, aryl, $OR^8$, $NR^6R^8$, $SR^6$, heteroaryl, arylalkyl, heteroarylalkyl, heterocyclyl, partially unsaturated heterocyclyl and heterocyclylalkyl; provided said ring does not contain two adjacent O or two adjacent S atoms;

or $R^8$ and $R^9$ together with the atoms to which they are attached may be independently joined to complete a 3 to 10 membered cycloalkyl ring or heterocycloalkyl ring optionally containing one or more additional heteroatoms selected from the group consisting of O, S, SO, $SO_2$ and $NR^6$, wherein each ring carbon may be optionally substituted with one to three groups independently selected from the group consisting of halogen, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, cyano, nitro, trifluoromethyl, difluoromethoxy, trifluoromethoxy, azido, aryl, $OR^8$, $NR^6R^8$, $SR^6$, heteroaryl, arylalkyl, heteroarylalkyl, heterocyclyl, partially unsaturated heterocyclyl and heterocyclylalkyl, provided said ring does not contain two adjacent O or two adjacent S atoms;

or $R^6$ and $R^{10}$ together with the atoms to which they are attached may be independently joined to complete a 3 to 10 membered cycloalkyl ring or heterocycloalkyl ring optionally containing one or more additional heteroatoms selected from the group consisting of O, S, SO, $SO_2$ and $NR^6$, wherein each ring carbon may be optionally substituted with one to three groups independently selected from the group consisting of halogen, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, cyano, nitro, trifluoromethyl, difluoromethoxy, trifluoromethoxy, azido, aryl, $OR^8$, $NR^6R^8$, $SR^6$, heteroaryl, arylalkyl, heteroarylalkyl, heterocyclyl, partially unsaturated heterocyclyl and heterocyclylalkyl, provided said ring does not contain two adjacent O or two adjacent S atoms;

or $R^8$ and $R^{10}$ together with the atoms to which they are attached may be independently joined to complete a 3 to 10 membered cycloalkyl ring or heterocycloalkyl ring optionally containing one or more additional heteroatoms selected from the group consisting of O, S, SO, $SO_2$ and $NR^6$, wherein each ring carbon may be optionally substituted with one to three groups independently selected from halogen, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, cyano, nitro, trifluoromethyl, difluoromethoxy, trifluoromethoxy, azido, aryl, $OR^8$, $NR^6R^8$, $SR^6$, heteroaryl, arylalkyl, heteroarylalkyl, heterocyclyl, partially unsaturated heterocyclyl and heterocyclylalkyl, provided said ring does not contain two adjacent O or two adjacent S atoms.

The term "alkyl" as used herein refers to a saturated linear or branched-chain monovalent hydrocarbon radical of one to twelve carbon atoms, wherein the alkyl radical may be optionally substituted independently with one or more substituents described below. Examples of alkyl groups include, but are not limited to, methyl, ethyl, n-propyl, isopropyl, butyl, isobutyl, sec-butyl, tert-butyl, pentyl, isopentyl, tert-pentyl, hexyl, isohexyl, and the like.

"Alkylene" means a linear or branched saturated divalent hydrocarbon radical of one to twelve carbon atoms, e.g., methylene, ethylene, propylene, 2-methylpropylene, pentylene, and the like.

The term "alkenyl" refers to linear or branched-chain monovalent hydrocarbon radical of two to twelve carbon atoms, containing at least one double bond, e.g., ethenyl, propenyl, and the like, wherein the alkenyl radical may be optionally substituted independently with one or more substituents described herein, and includes radicals having "cis" and "trans" orientations, or alternatively, "E" and "Z" orientations.

The term "alkenylene" refers to a linear or branched divalent hydrocarbon radical of two to twelve carbons containing at least one double bond, wherein the alkenylene radical may be optionally substituted independently with one or more substituents described herein. Examples include, but are not limited to, ethenylene, propenylene, and the like.

The term "alkynyl" refers to a linear or branched monovalent hydrocarbon radical of two to twelve carbon atoms containing at least one triple bond. Examples include, but are not limited to, ethynyl, propynyl, and the like, wherein the alkynyl radical may be optionally substituted independently with one or more substituents described herein.

The term "alkynylene" to a linear or branched divalent hydrocarbon radical of two to twelve carbons containing at least one triple bond, wherein the alkynylene radical may be optionally substituted independently with one or more substituents described herein.

The term "allyl" refers to a radical having the formula RC=CHCHR, wherein R is alkyl, alkenyl, alkynyl, cycloalkyl, heterocycloalkyl, aryl, heteroaryl, or any substituent as defined herein, wherein the allyl may be optionally substituted independently with one or more substituents described herein.

The term "cycloalkyl" refers to saturated or partially unsaturated cyclic hydrocarbon radical having from three to twelve carbon atoms, wherein the cycloalkyl may be optionally substituted independently with one or more substituents described herein. The term "cycloalkyl" further includes bicyclic and tricyclic cycloalkyl structures, wherein the bicyclic and tricyclic structures may include a saturated or partially unsaturated cycloalkyl fused to a saturated or partially unsaturated cycloalkyl or heterocycloalkyl ring or an aryl or heteroaryl ring. Examples of cycloalkyl groups include, but are not limited to, cyclopropyl, cyclobutyl, cyclopentyl, cyclohexyl, cycloheptyl, adamantly, norboranes and the like.

The term "heteroalkyl" refers to saturated linear or branched-chain monovalent hydrocarbon radical of one to twelve carbon atoms, wherein at least one of the carbon atoms is replaced with a heteroatom selected from N, O, or S, and wherein the radical may be a carbon radical or heteroatom radical (i.e., the heteroatom may appear in the middle or at the end of the radical). The heteroalkyl radical may be optionally substituted independently with one or more substituents described herein. The term "heteroalkyl" encompasses alkoxy and heteroalkoxy radicals.

The term "heterocycloalkyl" refers to a saturated or partially unsaturated cyclic radical of 3 to 8 ring atoms in which at least one ring atom is a heteroatom selected from nitrogen, oxygen and sulfur, the remaining ring atoms being C where one or more ring atoms may be optionally substituted independently with one or more substituent described below. The radical may be a carbon radical or heteroatom radical. "Heterocycloalkyl" also includes radicals where heterocycle radicals are fused with aromatic or heteroaromatic rings. Examples of heterocycloalkyl rings include, but are not limited to, pyrrolidine, piperidine, piperazine, tetrahydropyranyl, morpholine, thiomorpholine, homopiperazine, phthalimide, and derivatives thereof.

The term "heteroalkenyl" refers to linear or branched-chain monovalent hydrocarbon radical of three to twelve carbon atoms, containing at least one double bond, e.g., ethenyl, propenyl, and the like, wherein at least one of the carbon atoms is replaced with a heteroatom selected from N, O, or S, and wherein the radical may be a carbon radical or heteroatom radical (i.e., the heteroatom may appear in the middle or at the end of the radical). The heteroalkenyl radical may be optionally substituted independently with one or more substituents described herein, and includes radicals having "cis" and "trans" orientations, or alternatively, "E" and "Z" orientations.

The term "heteroalkynyl" refers to a linear or branched monovalent hydrocarbon radical of three to twelve carbon atoms containing at least one triple bond. Examples include, but are not limited to, ethynyl, propynyl, and the like, wherein at least one of the carbon atoms is replaced with a heteroatom selected from N, O, or S, and wherein the radical may be a carbon radical or heteroatom radical (i.e., the heteroatom may appear in the middle or at the end of the radical). The heteroalkynyl radical may be optionally substituted independently with one or more substituents described herein.

The term "heteroallyl" refers to radicals having the formula RC=CHCHR, wherein R is alkyl, alkenyl, alkynyl, cycloalkyl, heterocycloalkyl, aryl, heteroaryl, or any substituent as defined herein, wherein at least one of the carbon atoms is replaced with a heteroatom selected from N, O, or S, and wherein the radical may be a carbon radical or heteroatom radical (i.e., the heteroatom may appear in the middle or at the end of the radical). The heteroallyl may be optionally substituted independently with one or more substituents described herein.

"Aryl" means a monovalent aromatic hydrocarbon monocyclic radical of 6 to 10 ring atoms or a polycyclic aromatic hydrocarbon, optionally substituted independently with one or more substituents described herein. More specifically the term aryl includes, but is not limited to, phenyl, 1-naphthyl, 2-naphthyl, and derivatives thereof.

"Heteroaryl" means a monovalent monocyclic aromatic radical of 5 to 10 ring atoms or a polycyclic aromatic radical, containing one or more ring heteroatoms selected from N, O, or S, the remaining ring atoms being C. The aromatic radical is optionally substituted independently with one or more substituents described herein. Examples include, but are not limited to, furyl, thienyl, pyrrolyl, pyridyl, pyrazolyl, pyrimidinyl, imidazolyl, pyrazinyl, indolyl, thiophen-2-yl, quinolyl, benzopyranyl, thiazolyl, and derivatives thereof.

The term "halo" represents fluoro, chloro, bromo or iodo. Likewise, the term "halogen" refers to a fluorine, chlorine, bromine, or iodine substituent.

In general, the various moieties or functional groups of the compounds of Formula I may be optionally substituted by one or more substituents. Examples of substituents suitable for purposes of this invention include, but are not limited to, halo, alkyl, allyl, alkenyl, alkynyl, heteroalkyl, heteroallyl, heteroalkenyl, heteroalkynyl, alkoxy, heteroalkoxy, $G_n$-cycloalkyl, $G_n$-heterocycloalkyl, $G_n$-OR, $G_n$-NO$_2$, $G_n$-CN, $G_n$-CO$_2$R, $G_n$-(C=O)R, $G_n$-O(C=O)R, $G_n$-O-alkyl, $G_n$-OAr, $G_n$-SH, $G_n$-SR, $G_n$-SOR, $G_n$-SO$_2$R, $G_n$-S—Ar, $G_n$-SOAr, $G_n$-SO$_2$Ar, aryl, heteroaryl, $G_n$-Ar, $G_n$-(C=O)NR$^2$R$^3$, $G_n$-NR$^2$R$^3$, $G_n$-NR(C=O)R, $G_n$-SO$_2$NR$^2$R$^3$, PO$_3$H$_2$, and SO$_3$H$_2$, wherein G is alkylene having from 1 to 4 carbons, or alkenylene or alkynylene each having from 2 to 4 carbons, wherein said alkylene, alkenylene, or alkynylene may be substituted or unsubstituted; n is zero or 1; R', R$^2$, and R$^3$ are independently alkyl, allyl, alkenyl, alkynyl, heteroalkyl, heteroallyl, heteroalkenyl, heteroalkynyl, alkoxy, heteroalkoxy, $G_n$-cycloalkyl, or $G_n$-heterocycloalkyl; and Ar is aryl or heteroaryl, wherein said alkyl, allyl, alkenyl, alkynyl, heteroalkyl, heteroallyl, heteroalkenyl, heteroalkynyl, alkoxy, heteroalkoxy, $G_n$-cycloalkyl, $G_n$-heterocycloalkyl, Ar, R$^1$, R$^2$, and R$^3$ may be further substituted or unsubstituted.

The compounds of this invention may possess one or more asymmetric centers, and such compounds can be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. Accordingly, this invention also includes racemates and resolved enantiomers, and diastereomers compounds of the Formula I. The methods for the determination of stereochemistry and the separation of stereoisomers are well known in the art (see discussion in Chapter 4 of "Advanced Organic Chemistry", 4th edition J. March, John Wiley and Sons, New York, 1992).

In addition to compounds of the Formula I, the invention also includes solvates, pharmaceutically acceptable prodrugs, pharmaceutically active metabolites, and pharmaceutically acceptable salts of such compounds.

The term "solvate" refers to an aggregate of a molecule with one or more solvent molecules.

A "pharmaceutically acceptable prodrug" is a compound that may be converted under physiological conditions or by solvolysis to the specified compound or to a pharmaceutically acceptable salt of such compound.

A "pharmaceutically active metabolite" is a pharmacologically active product produced through metabolism in the body of a specified compound or salt thereof. Metabolites of a compound may be identified using routine techniques known in the art and their activities determined using tests such as those described herein.

Prodrugs and active metabolites of a compound may be identified using routine techniques known in the art. Various forms of prodrugs are known in the art. For examples of such prodrug derivatives, see, for example, a) *Design of Prodrugs*, edited by H. Bundgaard, (Elsevier, 1985) and *Methods in Enzymology*, Vol. 42, p. 309-396, edited by K. Widder, et al. (Academic Press, 1985); b) *A Textbook of Drug Design and Development*, edited by Krogsgaard-Larsen and H. Bundgaard, Chapter 5 "Design and Application of Prodrugs", by H. Bundgaard p. 113-191 (1991); c) H. Bundgaard, *Advanced Drug Delivery Reviews*, 8:1-38 (1992); d) H. Bundgaard, et al., *Journal of Pharmaceutical Sciences*, 77:285 (1988); and e) N. Kakeya, et al., *Chem. Pharm. Bull.*, 32:692 (1984).

A "pharmaceutically acceptable salt" is a salt that retains the biological effectiveness of the free acids and bases of the specified compound and that is not biologically or otherwise undesirable. A compound of the invention may possess a sufficiently acidic, a sufficiently basic, or both functional groups, and accordingly react with any of a number of inorganic or organic bases, and inorganic and organic acids, to form a pharmaceutically acceptable sale. Examples of pharmaceutically acceptable salts include those salts prepared by reaction of the compounds of the present invention with a mineral or organic acid or an inorganic base, such salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyn-1,4-dioates, hexyne-1,6-dioates, benzoates, chlorobenzoates, methylbenzoates, dinitromenzoates, hydroxybenzoates, methoxybenzoates, phthalates, sulfonates, xylenesulfonates, pheylacetates, phenylpropionates, phenylbutyrates, citrates, lactates, γ-hydroxybutyrates, glycollates, tartrates, methanesulfonates, propanesulfonates, naphthalene-1-sulfonates, naphthalene-2-sulfonates, tosylates, besylates, acetate and mandelates.

If the inventive compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid such as glucuronic acid or galacturonic acid, an alphahydroxy acid such as citric acid or tartaric acid, an amino acid such as aspartic acid or glutamic acid, an aromatic acid such as benzoic acid or cinnamic acid, a sulfonic acid such as p-toluenesulfonic acid or ethanesulfonic acid, or the like.

If the inventive compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The inventive compounds may be prepared using the reaction routes and synthesis schemes as described below, employing the techniques available in the art using starting materials that are readily available.

Therapeutic Aspects of the Invention

Therapeutically effective amounts of the compounds of the invention may be used to treat diseases mediated by modulation or regulation of type I receptor tyrosine kinases and/or serine, threonine, and/or dual specificity kinases. An "effective amount" is intended to mean that amount of compound that, when administered to a mammal in need of such treatment, is sufficient to effect treatment for a disease mediated by the activity of one or more type I receptor tyrosine kinases and/or serine, threonine, and/or dual specificity kinases. Thus, for example, a therapeutically effective amount of a compound selected from Formula I or a salt, active metabolite or prodrug thereof, is a quantity sufficient to modulate, regulate, or inhibit the activity of one or more type I receptor tyrosine kinases and/or serine, threonine, and/or dual specificity kinases such that a disease condition which is mediated by that activity is reduced or alleviated.

The amount of a given agent that will correspond to such an amount will vary depending upon factors such as the particular compound, disease condition and its severity, the identity (e.g., weight) of the mammal in need of treatment, but can nevertheless be routinely determined by one skilled in the art. "Treating" is intended to mean at least the mitigation of a disease condition in a mammal, such as a human, that is affected, at least in part, by the activity of one or more type I receptor tyrosine kinases and/or serine, threonine, and/or dual specificity kinases, and includes, but is not limited to, preventing the disease condition from occurring in a mammal, particularly when the mammal is found to be predisposed to having the disease condition but has not yet been diagnosed as having it; modulating and/or inhibiting the disease condition; and/or alleviating the disease condition.

In order to use a compound of the Formula I, or a pharmaceutically acceptable salt or in vivo cleavable prodrug thereof, for the therapeutic treatment (including prophylactic treatment) of mammals including humans, it is normally formulated in accordance with standard pharmaceutical practice as a pharmaceutical composition. According to this aspect of the invention there is provided a pharmaceutical composition that comprises a compound of the Formula I, or a pharmaceutically acceptable salt or in vivo cleavable prodrug thereof, as defined hereinbefore in association with a pharmaceutically acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, or intramuscular dosing or as a suppository for rectal dosing). For example, compositions intended for oral use may contain one or more coloring, sweetening, flavoring and/or preservative agents.

Suitable pharmaceutically-acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxyethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), coloring agents, flavoring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent, and one or more preservatives. Suitable dispersing or wetting agents and suspending agents are exemplified by those already mentioned above. Additional excipients such as sweetening, flavoring and coloring agents, may also be present.

The pharmaceutical compositions of the invention may also be in the form of oil-in-water emulsions. The oily phase may be a vegetable oil, such as olive oil or arachis oil, or a mineral oil such as liquid paraffin, or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavoring and preservative agents.

Syrups and elixirs may be formulated with sweetening agents such as glycerol, propylene glycol, sorbitol, aspartame or sucrose, and may also contain a demulcent, preservative, flavoring and/or coloring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient, which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedures well known in the art.

Compositions for administration by insufflation may be in the form of a finely divided powder containing particles of average diameter of, for example, 30 µm or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurized aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulations, see Chapter 25.2 in Volume 5 of Comprehensive Medicinal Chemistry (Corwin Hansch; Chairman of Editorial Board), Pergamon Press, 1990.

The amount of a compound of this invention that is combined with one or more excipients to produce a single dosage form will necessarily vary depending upon the host treated and the particular route of administration. For example, a formulation intended for oral administration to humans may contain, for example, from 0.5 mg to 2 g of active agent compounded with an appropriate and convenient amount of excipients, which may vary from about 5 to about 98 percent by weight of the total composition. Dosage unit forms will generally contain about 1 mg to about 500 mg of an active ingredient. For further information on routes of administration and dosage regimes, see Chapter 25.3 in Volume 5 of Comprehensive Medicinal Chemistry (Corwin Hansch; Chairman of Editorial Board), Pergamon Press, 1990.

The size of the dose for therapeutic or prophylactic purposes of a compound of Formula I will naturally vary according to the nature and severity of the conditions, the age and sex of the animal or patient and the route of administration, according to well known principles of medicine.

Although the compounds of Formula I are primarily of value as therapeutic agents for use in warm-blooded animals (including man), they are also useful whenever it is required to control type I receptor tyrosine kinases and/or serine, threonine, and/or dual specificity kinases. Thus, they are useful as pharmacological standards for use in the development of new biological tests and in the search for new pharmacological agents.

The activity of the compounds of this invention may be assayed for type I receptor tyrosine kinases inhibition and/or serine, threonine, and/or dual specificity kinases in vitro, in vivo, or in a cell line. In vitro assays include assays that determine inhibition of the kinase activity. Alternate in vitro assays quantitate the ability of the inhibitor to bind to kinases and may be measured either by radiolabelling the inhibitor prior to binding, isolating the inhibitor/kinase complex and determining the amount of radiolabel bound, or by running a competition experiment where new inhibitors are incubated with known radioligands. These and other useful in vitro and cell culture assays are well known to those of skill in the art.

Although the invention has been described and illustrated with a certain degree of particularity, it is understood that the present disclosure has been made only by way of example, and that numerous changes in the combination and arrangement of parts can be resorted to by those skilled in the art without departing from the spirit and scope of the invention, as hereinafter claimed.

BIOLOGICAL EXAMPLES

EGFR/ErbB2 Enzymatic Assays

Thermo LabSystems Immulon 4HBX 96-well plates are coated by incubation overnight at room temperature with 100 µL per well of 0.25 mg/mL Poly (Glu, Tyr) 4:1 (PGT) (Sigma Chemical Co., St. Louis, Mo.) in PBS (phosphate buffered saline). Excess PGT is removed by aspiration, and the plate is washed three times with wash buffer (0.1% Tween 20 in PBS). The kinase reaction is performed in 100 µL of 50 mM HEPES (pH 7.3) containing 125 mM sodium chloride, 24 mM magnesium chloride, 0.1 mM sodium orthovanadate, 15 µM ATP (adenosine triphosphate) and 0.3 units/mL EGFR (epidermal growth factor receptor) (BIOMOL Research Laboratories, Inc., Plymouth Meeting, Pa.). The compound in DMSO (dimethylsulfoxide) is added to give a final DMSO concentration of about 1%. Phosphorylation is initiated by the addition of ATP and incubated for 30 minutes at room temperature. The kinase reaction is terminated by aspiration of the reaction mixture and subsequent washing with wash buffer (see above). Phosphorylated PGT is detected by 30 incubation with 100 µL per well HRP conjugated PY20 antiphosphotyrosine antibody (Zymed Laboratories, Inc., South San Francisco, Calif.) diluted to 0.2 µg/mL in 3% BSA and 0.05% Tween 20 in PBS. Antibody is removed by aspiration, and the plate is washed with wash buffer. The colorimetric signal is developed by the addition of 100 µL per well TMB Microwell Peroxidase Substrate (Kirkegaard and Perry, Gaithersburg, Md.), and stopped by the addition of 100 µL per well 1M phosphoric acid. Phosphotyrosine in measured by absorbance at 450 nm.

The ErbB2 kinase is as above using 250 ng/mL erbB2 intracellular domain in place of EGFR. The intracellular domain of the ErbB2 tyrosine kinase (amino acids 691-1255) is expressed as a his-tagged protein in Baculovirus and purified by nickel chelating, ion exchange and size exclusion chromatography.

Compounds of the present invention have $IC_{50}$'s from less than 1 nM to 50 mM.

PREPARATIVE EXAMPLES

An illustration of the preparation of compounds of the present invention is shown in FIGS. 1-6.

FIG. 1 illustrates the synthesis of imino amidine compounds of the present invention. Hydrazones (3) can be prepared by standard methods of condensation of the aldehyde (1) with hydrazine (2). This can be accomplished in a range of organic solvents. Preferably, the condensation is performed in a mixed solvent system of DCM and IPA. Couplings to form imino amidines (5) can be achieved by heating hydrazone (3) in a solvent mixture of THF and IPA at about 50° C. in the presence of an imidate (4).

FIG. 2 illustrates an alternative synthesis of imino amidine compounds of the present invention. In this route, an amide (6) is treated with $POCl_3$ in a suitable organic solvent like benzene or DCM to form the imidoyl chloride intermediate. Hydrazone (3) is then added to this mixture to generate the desired imino amidine (5). This coupling may require slightly elevated temperatures (45 to 90° C.).

FIGS. 3 and 4 outline syntheses of imino amidine compounds of the present invention in which a imino amidine (7) is prepared and then condensed with aldehyde (1). In FIG. 3, imino amidine (7) can be prepared by coupling of hydrazine (2) with imidate (4) in a suitable organic solvent. The resulting imino amidine (7) can then be condensed with aldehyde (1) in a suitable organic solvent such as THF and IPA or EtOH at room temperature or slightly elevated temperature (45 to 90° C.) to furnish the desired imino amidine (5). In FIG. 4, imino amidine (7) can be prepared by coupling hydrazine (2) with thioimidate (8) in a suitable organic solvent. As in FIG. 3, the resulting imino amidine (7) can then be condensed with aldehyde (1) in a suitable organic solvent such as THF and IPA or EtOH at room temperature or slightly elevated temperature (45 to 90° C.) to furnish the desired imino amidine (5).

Oxazoline compounds of formula I can be prepared as outlined in FIG. 5. Aniline (9) can be condensed with thioCDI in a suitable organic solvent such as a mixture of THF and DCE. The resulting intermediate is not isolated but rather treated in situ with amino alcohol (10). The addition reaction can be accomplished at room temperature or at slightly elevated temperatures (45 to 90° C.). Generally, the resulting thiourea (11) can be isolated and carried forward without purification. The desired oxazoline (12) can be prepared from the thiourea (11) by one of several routes outlined in FIG. 5. The thiourea (11) can be treated with tosyl chloride and NaOH in a mixture of THF and water at room temperature. Alternatively, the thiourea (11) can be treated with a variety of carbodiimidates such as in EDCI, DCC, DCI in suitable organic solvents such as THF, DMF, DCM or DCE at room temperature or slightly elevated temperatures (45 to 90° C.).

FIG. 6 illustrates an alternative approach to oxazoline compounds of the present invention. Aniline (9) can be coupled with diphenyl N-cyanocarbonimidate (13) with or without a base such as NaH or $Et_3N$ in organic solvents such as DMF, MeCN, dioxane, pyridine, IPA or DCM at room temperature or elevated temperatures (45 to 120° C.) to give cyano isourea (14). Preferably, cyano isourea (14) is formed by coupling aniline (9) and diphenyl N-cyanocarbonimidate (13) in a mixture of THF/DCE/tBuOH at 80-90° C. Oxazoline (12) can be prepared by coupling amino alcohol (10) and cyano isourea (14) in a variety of organic solvents including THF and IPA. Preferably, the coupling of (10) and (14) is accomplished in a mixture of THF and IPA at elevated temperatures (45 to 120° C.).

In order to illustrate the invention, the following examples are included. However, it is to be understood that these examples do not limit the invention and are only meant to suggest a method of practicing the invention. Persons skilled in the art will recognize that the chemical reactions described may be readily adapted to prepare a number of other quinazoline analogs of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

EXAMPLES

In the examples described below, unless otherwise indicated all temperatures are set forth in degrees Celsius. Reagents were purchased from commercial suppliers such as Aldrich Chemical Company, Lancaster, TCI or Maybridge, and were used without further purification unless otherwise indicated.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was done on a Biotage system (Manufacturer: Dyax Corporation) having a silica gel column or on a silica SepPak cartridge (Waters).

¹H-NMR spectra were recorded on a Varian instrument operating at 400 MHz. ¹H-NMR spectra were obtained as CDCl₃ solutions (reported in ppm), using chloroform as the reference standard (7.25 ppm). Other NMR solvents were used as needed. When peak multiplicities are reported, the following abbreviations are used: s (singlet), d (doublet), t (triplet), m (multiplet), br (broadened), dd (doublet of doublets), dt (doublet of triplets).

Example 1

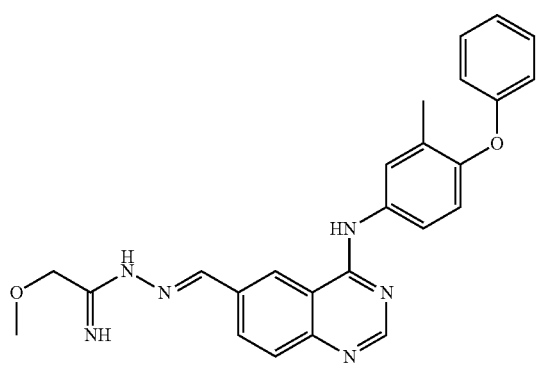 [SMILES: COCC(=N)N/N=C/c1ccc2ncnc(Nc3ccc(Oc4ccccc4)c(C)c3)c2c1]

Preparation of (E)-2-methoxy-N-((4-(3-methyl-4-phenoxyphenylamino)quinazolin-6-yl)methyleneamino)acetamidine Step A: (6-Hydrazonomethylquinazolin-4-yl)-(3-methyl-4-phenoxyphenyl)amine is prepared by adding hydrazine (50 mg, 1.00 mmol) to a solution of 4-(3-methyl-4-phenoxyphenylamino)-quinazoline-6-carbaldehyde (250 mg, 0.70 mmol) in a 1:1 mixture of DCM:IPA (6 mL). After stirring at room temperature for 4 hours, excess hydrazine and solvent are removed under reduced pressure to give the desired hydrazone as a brown solid which is carried forward without purification.

Step B: (E)-2-Methoxy-N-((4-(3-methyl-4-phenoxyphenylamino)quinazolin-6-yl)methyleneamino)acetamidine is prepared by adding (6-hydrazonomethylquinazolin-4-yl)-(3-methyl-4-phenoxyphenyl)amine (30 mg, 0.081 mmol) to a stirred mixture of Et₃N (20 mg, 0.19 mmol) and 2-methoxyacetimidic acid methyl ester (20 mg, 0.20 mmol) in a 1:1 mixture of DCM:IPA (4 mL). After stirring the reaction mixture at 50° C. for 1 hour, it is cooled to room temperature and stirred for 16 hours. Concentration and purification by column chromatography (10:8:1 EtOAc:Hexanes:MeOH) provides the desired product (16 mg, 45%). MS ESI (+) m/z 441 (M+1) detected; ¹H NMR (400 mHz, CD₃OD) δ 8.64 (s, 1H), 8.49 (s, 1H), 8.41 (m, 2H), 7.76 (d, 1H), 7.63 (d, 1H), 7.55 (dd, 1H), 7.32 (m, 2H), 7.05 (m, 1H), 6.93 (m, 3H), 4.13 (s, 2H), 3.45 (s, 3H), 3.41 (s, 1H), 2.24 (s, 3H).

The following compounds (Examples 2-5) are prepared as described in Example 1 using the appropriate quinazoline-6-aldehyde, hydrazine and imidate.

Example 2

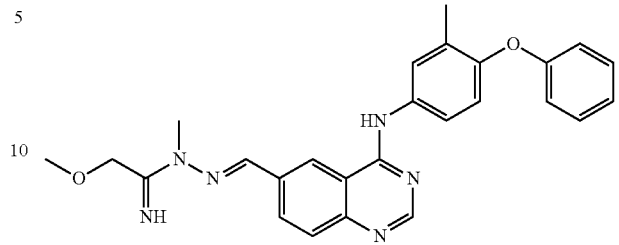

(E)-2-Methoxy-N-methyl-N-((4-(3-methyl-4-phenoxyphenylamino)quinazolin-6-yl)methyleneamino)acetamidine MS APCI (+) m/z 455 (M+1) detected; ¹H NMR (400 mHz, CD₃OD) δ 8.48 (s, 1H), 8.23 (s, 1H), 8.26 (d, 1H), 7.91 (s, 1H), 7.77 (d, 1H), 7.64 (d, 1H), 7.54 (dd, 1H), 7.32 (m, 2H), 7.05 (m, 1H), 6.94 (m, 3H), 4.55 (s, 2H), 3.72 (m, 1H), 3.54 (s, 3H), 2.25 (s, 3H), 2.15 (s, 3H).

Example 3

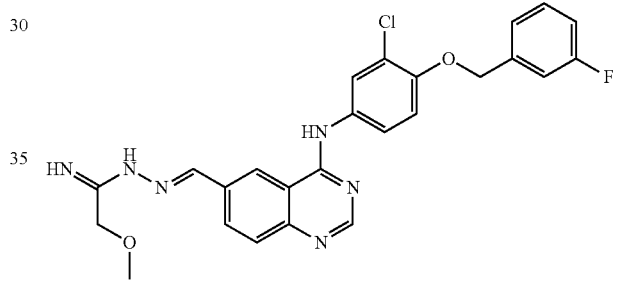

(E)-N-((4-(4-(3-Fluorobenzyloxy)-3-chlorophenylamino)quinazolin-6-yl)methyleneamino)-2-methoxyacetamidine MS APCI (+) m/z 493, 495 (M+1, Cl pattern) detected; ¹H NMR (400 mHz, DMSO-D₆) δ 8.75 (s, 1H), 8.59 (s, 1H), 8.46 (d, 1H), 8.40 (s, 1H), 8.03 (d, 1H), 7.76 (m, 2H), 7.47 (m, 1H), 7.31 (m, 3H), 7.19 (m, 1H), 5.27 (s, 2H), 4.02 (s, 2H), 3.34 (m, 4H).

Example 4

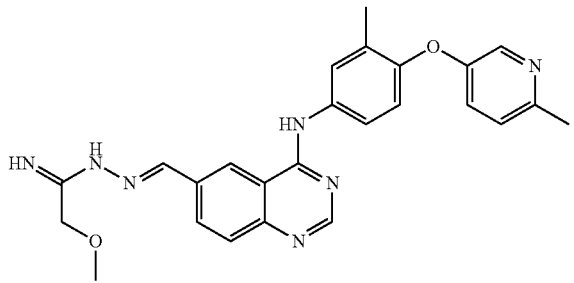 [SMILES: COCC(=N)N/N=C/c1ccc2ncnc(Nc3ccc(Oc4ccc(C)nc4)c(C)c3)c2c1]

(E)-N-(4-(3-Methyl-4-(6-methylpyridin-3-yloxy) phenylamino)quinazolin-6-yl)methyleneamino-2-methoxyacetamidine MS ESI (+) m/z 456 (M+1) detected; $^1$H NMR (400 MHz, CD$_3$OD) δ 8.63 (s, 1H), 8.5 (s, 1H), 8.41 (m, 2H), 8.12 (s, 1H), 7.79 (d, 1H), 7.7 (s, 1H), 7.61 (d, 1H), 7.26 (m, 2H), 7.01 (d, 1H), 4.12 (s, 2H), 3.43 (s, 3H), 2.52 (s, 3H), 2.12 (s, 3H).

Example 5

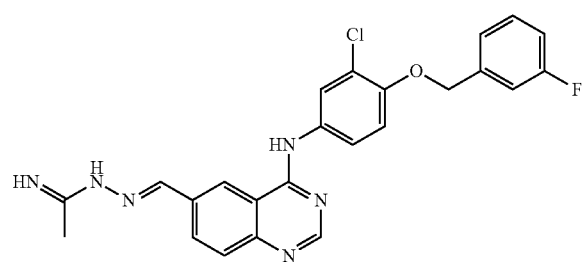 [SMILES: CC(=N)N/N=C/c1ccc2ncnc(Nc3ccc(OCc4cccc(F)c4)c(Cl)c3)c2c1]

(E)-N-((4-(4-(3-Fluorobenzyloxy)-3-chlorophenylamino)-quinazolin-6-yl)-methyleneamino)-acetamidine MS ESI (+) m/z 463, 465 (M+1, Cl pattern) detected; $^1$H NMR (400 MHz, CD$_3$OD) δ 8.64 (s, 1H), 8.52 (s, 1H), 8.42 (m, 2H), 7.92 (s, 1H), 7.78 (d, 1H), 7.6 (d, 1H), 7.4 (m, 1H), 7.31 (d, 1H), 7.25 (d, 1H), 7.19 (d, 1H), 7.06 (t, 1H), 5.21 (s, 2H), 2.06 (s, 3H).

Example 6

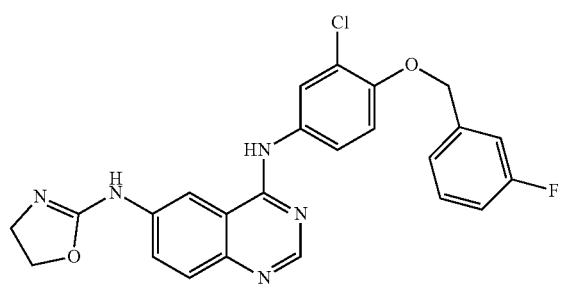 [SMILES: Fc1cccc(COc2ccc(Nc3ncnc4ccc(NC5=NCCO5)cc34)cc2Cl)c1]

Preparation of N4-[3-chloro-4-(3-fluorobenzyloxy)-phenyl]-N6-(4,5-dihydrooxazol-2-yl)-quinazoline-4,6-diamine Step A: N-4-[3-Chloro-4-(3-fluorobenzyloxy)-phenyl]-N6-(2-phenyl-N-cyanoisourea)-quinazoline-4,6-diamine is prepared by stirring N-4-[3-chloro-4-(3-fluoro-benzyloxy)-phenyl]-quinazoline-4,6-diamine (0.63 g, 1.60 mmol) and diphenyl N-cyanocarbonimidate (1.0 g, 4.20 mmol), in THF (20 mL), DCE (10 mL) and t-BuOH (10 mL) at room temperature for 2 hours, then at 80-90° C. for 3 hours. An additional 0.40 g of diphenyl N-cyanocabonimidate is added. After stirring at 80-90° C. for 3 hours, the reaction mixture is cooled to room temperature and concentrated. DCM (100 mL) is added, and the solid is isolated by filtration through a sintered glass funnel and dried, yielding 0.67 g (77.6%) of tan-yellow material.

Step B: N4-[3-Chloro-4-(3-fluorobenzyloxy)-phenyl]-N6-(4,5-dihydrooxazol-2-yl)-quinazoline-4,6-diamine is prepared by adding 2-aminoethanol (10 mg, 0.164 mmol) to a mixture of N-4-[3-chloro-4-(3-fluorobenzyloxy)-phenyl]-N6-(2-phenyl-N-cyanoisourea)-quinazoline-4,6-diamine (30 mg, 0.056 mmol) in 1:1 THF:isopropyl alcohol (2 mL) and heating to 100° C. for 20 hours. The reaction mixture is concentrated under reduced pressure and purified by column chromatography (5% MeOH in ethyl acetate) to provide the desired product as a white solid (19 mg, 74%). MS ESI (+) m/z 464, 466 (M+1, Cl pattern) detected; $^1$H NMR (400 mHz, acetone-d$_6$) δ 8.52 (s, 1H), 8.43 (bs, 1H), 8.17 (d, 1H), 7.85 (dd, 1H), 7.74 (d, 1H), 7.70 (d, 1H), 7.48 (m, 1H), 7.38 (d, 1H), 7.35 (d, 1h), 7.21 (d, 1H), 7.12 (m, 1H), 5.29 (s, 2H), 4.42 (t, 2H), 3.93 (t, 2H).

Example 7

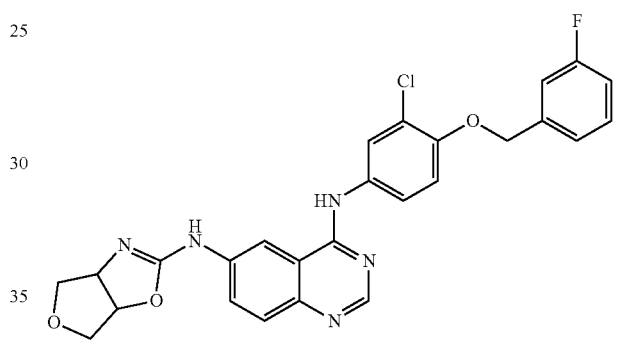

Preparation of N4-[3-chloro-4-(3-fluorobenzyloxy)-phenyl]-N6-(3a,4,6,6a-tetrahydrofuro[3,4-d]oxazol-2-yl)-quinazoline-4,6-diamine N4-[3-Chloro-4-(3-fluorobenzyloxy)-phenyl]-N6-(3a,4,6,6a-tetrahydrofuro[3,4-d]oxazol-2-yl)-quinazoline-4,6-diamine is prepared by adding thioCDI (27 mg, 0.152 mmol) to a stirred solution of N-4-[3-chloro-4-(3-fluoro-benzyloxy)-phenyl]-quinazoline-4,6-diamine (60 mg, 0.152 mmol) in 1:1 THF:DCM (8 mL). After 3 hours, 2-aminocyclopentanol (30 mg, 0.30 mmol) is added and the reaction mixture stirred for 4 hours. Solvent is removed under reduced pressure and the resulting thiourea is triturated with diethyl ether. The crude thiourea is suspended in THF (10 mL) and 1 M NaOH in water (0.38 mL) is added followed by addition of a 1 M TsCl solution in THF (0.17 mL). After 1 hour, the reaction mixture is diluted with EtOAc and water, and the phases separated. The aqueous phase is extracted with EtOAc and the combined organic extracts are dried (Na$_2$SO$_4$) and concentrated. Purification by column chromatography (10:5:1 EtOAc:Hexanes:MeOH) provides the desired product (50 mg, 65%). MS APCI (+) m/z 506, 508 (M+1, Cl pattern) detected; $^1$H NMR (400 mHz, CD$_3$CN) δ 8.49 (s, 1H), 8.23 (bs, 1H), 7.94 (s, 1H), 7.73 (m, 2H), 7.59 (m, 2H), 7.45 (m, 1H), 7.35 (d, 1H), 7.29 (d, 1H), 7.19-7.10 (m, 3H), 5.23 (s, 2H), 5.18 (m, 1H), 4.66 (m, 1H), 4.11 (d, 1H), 3.96 (d, 1H), 3.56 (dd, 2H).

The following compounds (Examples 8-56) are prepared as described in Example 7 using the appropriate quinazoline-6-aniline, and amino alcohol.

Example 8

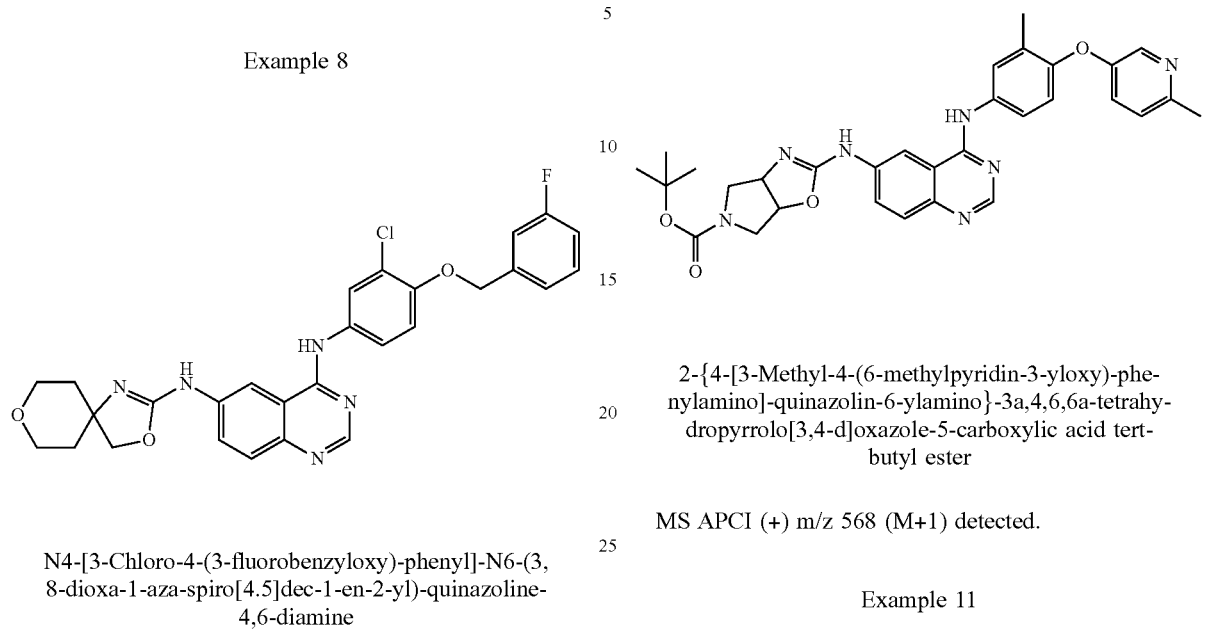

N4-[3-Chloro-4-(3-fluorobenzyloxy)-phenyl]-N6-(3,8-dioxa-1-aza-spiro[4.5]dec-1-en-2-yl)-quinazoline-4,6-diamine MS APCI (+) m/z 534, 536 (M+1, Cl pattern) detected; $^1$H NMR (400 mHz, CD$_3$CN) δ 8.50 (s, 1H), 8.12 (s, 1H), 7.99 (s, 1H), 7.73 (d, 1H), 7.60 (d, 1H), 7.47 (m, 1H), 7.34 (d, 1H), 7.29 (d, 1H), 7.15 (d, 1H), 7.11 (d, 1H), 5.23 (s, 2H), 4.19 (m, 2H), 3.88 (m, 2H), 3.59 (m, 2H), 3.30 (m, 2H), 1.78 (m, 5H).

Example 9

N6-(3,8-Dioxa-1-aza-spiro[4.5]dec-1-en-2-yl)-N4-[3-methyl-4-(6-methylpyridin-3-yloxy)-phenyl]-quinazoline-4,6-diamine MS APCI (+) m/z 497 (M+1) detected; $^1$H NMR (400 mHz, CD$_3$OD) δ 8.44 (s, 1H), 8.19 (bs, 1H), 8.13 (d, 1H), 7.71 (m, 3H), 7.63 (dd, 1H), 7.29 (m, 2H), 7.00 (d, 1H), 4.30 (s, 2H), 3.97 (m, 2H), 3.55 (m, 2H), 2.50 (s, 3H), 2.27 (s, 3H), 1.96 (m, 2H), 1.77 (m, 2H).

Example 10

2-{4-[3-Methyl-4-(6-methylpyridin-3-yloxy)-phenylamino]-quinazolin-6-ylamino}-3a,4,6,6a-tetrahydropyrrolo[3,4-d]oxazole-5-carboxylic acid tert-butyl ester MS APCI (+) m/z 568 (M+1) detected.

Example 11

N4-[3-Methyl-4-(6-methylpyridin-3-yloxy)-phenyl]-N6-(4,5,6,6a-tetrahydro-3aH-pyrrolo[3,4-d]oxazol-2-yl)-quinazoline-4,6-diamine N4-[3-Methyl-4-(6-methyl pyridin-3-yloxy)-phenyl]-N6-(4,5,6,6a-tetrahydro-3aH-pyrrolo[3,4-d]oxazol-2-yl)-quinazoline-4,6-diamine is prepared from 2-{4-[3-methyl-4-(6-methylpyridin-3-yloxy)-phenyl amino]-quinazolin-6-ylamino}-3a,4,6,6a-tetrahydropyrrolo[3,4-d]oxazole-5-carboxylic acid tert-butyl ester by standard BOC deprotection methods using TFA in methylene chloride. MS APCI (+) m/z 468 (M+1) detected; $^1$H NMR (400 mHz, CD$_3$OD) δ 8.42 (s, 1H), 8.21 (bs, 1H), 8.13 (d, 1H), 7.68 (m, 2H), 7.60 (m, 2H), 7.28 (m, 2H), 6.98 (d, 1H), 5.18 (m, 1H), 4.74 (m, 1H), 3.34 (d, 1H), 3.16 (d, 1H), 2.86 (m, 2H), 2.50 (s, 3H), 2.26 (s, 3H).

Example 12

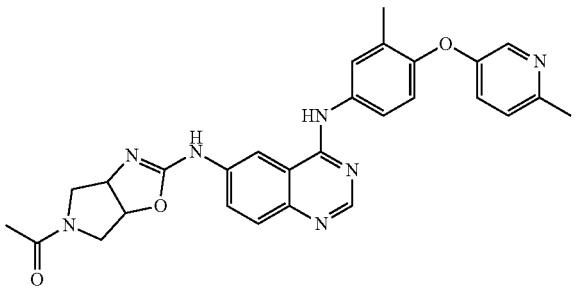 [SMILES: CC(=O)N1CC2N=C(Nc3ccc4ncnc(Nc5ccc(Oc6ccc(C)nc6)c(C)c5)c4c3)OC2C1]

1-(2-{4-[3-Methyl-4-(6-methylpyridin-3-yloxy)-phenylamino]-quinazolin-6-ylamino}-3a,4,6,6a-tetrahydropyrrolo[3,4-d]oxazol-5-yl)-ethanone 1-(2-{4-[3-Methyl-4-(6-methylpyridin-3-yloxy)-phenylamino]-quinazolin-6-ylamino}-3a,4,6,6a-tetrahydropyrrolo[3,4-d]oxazol-5-yl)-ethanone is prepared from N4-[3-methyl-4-(6-methylpyridin-3-yloxy)-phenyl]-N6-(4,5,6,6a-tetrahydro-3aH-pyrrolo[3,4-d]oxazol-2-yl)-quinazoline-4,6-diamine by standard acetylation methods using acetic anhydride in a mixture of pyridine and methylene chloride. MS APCI (+) m/z 510 (M+1) detected; $^1$H NMR (400 mHz, CD$_3$OD) δ 8.44 (s, 1H), 8.26 (d, 1H), 8.13 (d, 1H), 7.71 (m, 2H), 7.63 (m, 2H), 7.28 (m, 2H), 7.00 (d, 1H), 5.28 (m, 1H), 4.89 (m, 1H), 4.15 (d, 0.5H), 4.03 (m, 1H), 3.84 (d, 0.5H), 3.75 (m, 1H), 3.47 (m, 1H), 2.50 (s, 3H), 2.27 (s, 3H), 2.09 (d, 3H).

Example 13

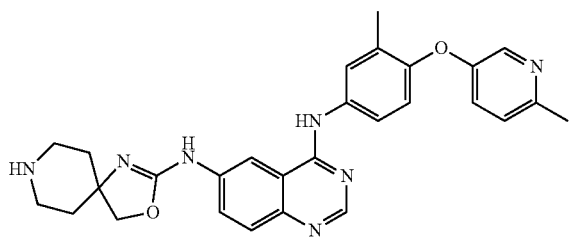 [SMILES: Cc1ccc(Oc2ccc(Nc3ncnc4ccc(NC5=NC6(CCNCC6)CO5)cc34)cc2C)cn1]

N4-[3-Methyl-4-(6-methylpyridin-3-yloxy)-phenyl]-N6-(3-oxa-1,8-diaza-spiro[4.5]dec-1-en-2-yl)-quinazoline-4,6-diamine N4-[3-Methyl-4-(6-methyl pyridin-3-yloxy)-phenyl]-N6-(3-oxa-1,8-diazaspiro[4.5]dec-1-en-2-yl)-quinazoline-4,6-diamine is prepared from 2-{4-[3-methyl-4-(6-methylpyridin-3-yloxy)-phenylamino]-quinazolin-6-ylamino}-3-oxa-1,8-diaza-spiro[4.5]dec-1-ene-8-carboxylic acid tert-butyl ester by standard BOC deprotection methods using TFA in methylene chloride. MS ESI (+) m/z 496 (M+1) detected; $^1$H NMR (400 mHz, CD$_3$OD) δ 8.43 (s, 1H), 8.39 (s, 1H), 8.12 (d, 1H), 7.70 (m, 3H), 7.61 (dd, 1H), 7.28 (m, 2H), 6.98 (d, 1H), 3.45 (m, 2H), 3.32 (m, 2H), 3.25 (m, 2H) 2.50 (s, 3H), 2.32 (m, 2H), 2.25 (s, 3H), 2.01 (m, 2H).

Example 14

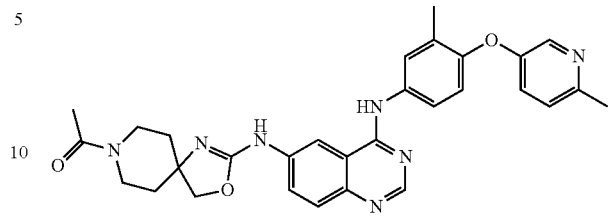

1-(2-{4-[3-Methyl-4-(6-methylpyridin-3-yloxy)-phenylamino]-quinazolin-6-ylamino}-3-oxa-1,8-diazaspiro[4.5]dec-1-en-8-yl)-ethanone 1-(2-{4-[3-Methyl-4-(6-methylpyridin-3-yloxy)-phenylamino]-quinazolin-6-ylamino}-3-oxa-1,8-diaza-spiro[4.5]dec-1-en-8-yl)-ethanone is prepared from N4-[3-methyl-4-(6-methylpyridin-3-yloxy)-phenyl]-N6-(3-oxa-1,8-diaza-spiro[4.5]dec-1-en-2-yl)-quinazoline-4,6-diamine by standard acetylation methods using acetic anhydride in a mixture of pyridine and methylene chloride.

Example 15

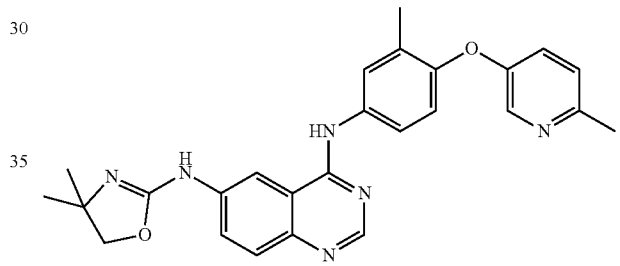

N6-(4,4-Dimethyl-4,5-dihydro-oxazol-2-yl)-N4-[3-methyl-4-(6-methylpyridin-3-yloxy)-phenyl]-quinazoline-4,6-diamine MS APCI (+) m/z 455 (M+1) detected; $^1$H NMR (400 mHz, CD$_3$OD) δ 8.42 (s, 1H), 8.12 (d, 1H), 7.70 (m, 4H), 7.60 (m, 3H), 7.28 (m, 2H), 6.99 (d, 1H), 4.13 (s, 2H), 2.50 (s, 3H), 2.26 (s, 3H), 1.40 (s, 6H).

Example 16

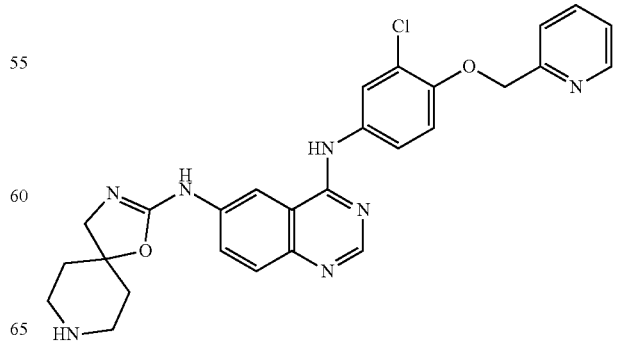

N4-[3-Chloro-4-(pyridin-2-ylmethoxy)-phenyl]-N6-(1-oxa-3,8-diazaspiro[4.5]dec-2-en-2-yl)-quinazoline-4,6-diamine N4-[3-Chloro-4-(pyridin-2-ylmethoxy)-phenyl]-N6-(1-oxa-3,8-diazaspiro[4.5]dec-2-en-2-yl)-quinazoline-4,6-diamine is prepared from 2-{4-[3-chloro-4-(pyridin-2-ylmethoxy)-phenylamino]-quinazolin-6-ylamino}-1-oxa-3,8-diaza-spiro[4.5]dec-2-ene-8-carboxylic acid tert-butyl ester by standard BOC deprotection methods using TFA in methylene chloride. MS ESI (+) m/z 516, 518 (M+1, Cl pattern) detected; $^1$H NMR (400 mHz, CDCl$_3$) δ 8.61 (s, 1H), 8.58 (d, 1H), 8.22 (bs, 1H), 7.97 (d, 1H), 7.70 (m, 2H), 7.67 (d, 1H), 7.64 (dd, 1H), 7.35 (d, 1H), 7.26 (m, 1H), 7.02 (d, 1H), 5.31 (s, 2H), 3.73 (s, 2H), 3.05 (m, 2H), 2.96 (m, 2H), 1.97 (m, 2H), 1.80 (m, 2H).

Example 17

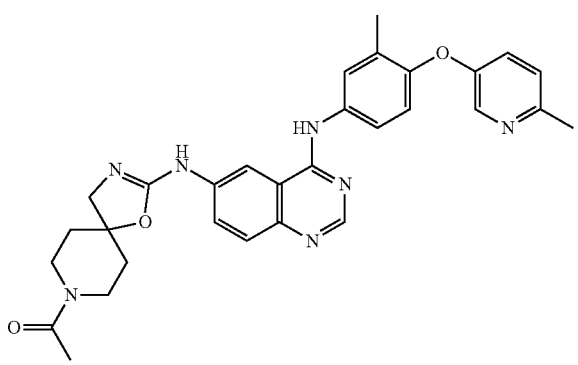 [SMILES: CC(=O)N1CCC2(CC1)CN=C(Nc1ccc3ncnc(Nc4ccc(Oc5ccc(C)nc5)c(C)c4)c3c1)O2]

1-(2-{4-[3-Methyl-4-(6-methylpyridin-3-yloxy)-phenyl amino]-quinazolin-6-ylamino}-1-oxa-3,8-diazaspiro[4.5]dec-2-en-8-yl)-ethanone 1-(2-{4-[3-Methyl-4-(6-methylpyridin-3-yloxy)-phenyl amino]-quinazolin-6-ylamino}-1-oxa-3,8-diaza-spiro[4.5]dec-2-en-8-yl)-ethanone is prepared from 2-{4-[3-methyl-4-(6-methylpyridin-3-yloxy)-phenylamino]-quinazolin-6-ylamino}-1-oxa-3,8-diazaspiro[4.5]dec-2-ene-8-carboxylic acid tert-butyl ester by standard BOC deprotection methods using TFA in methylene chloride followed by standard acetylation methods using acetic anhydride in a mixture of pyridine and methylene chloride. MS ESI (+) m/z 538 (M+1) detected; $^1$H NMR (400 mHz, CDCl$_3$) δ 8.68 (s, 1H), 8.28 (d, 1H), 7.83 (d, 1H), 7.64 (s, 1H), 7.52 (d, 2H), 7.48 (d, 2H), 7.12 (m, 3H), 6.93 (d, 1H), 3.69 (m, 2H), 2.53 (s, 3H), 2.29 (s, 3H), 2.14 (s, 3H), 2.02 (m, 2H), 1.78 (m, 2H), 1.30 (m, 2H), 0.87 (m, 2H).

Example 18

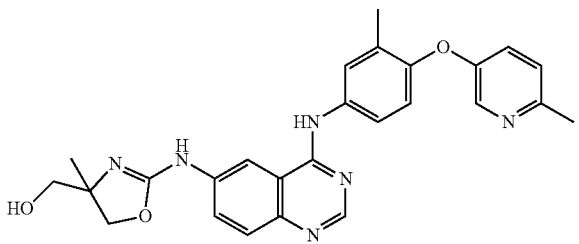 [SMILES: Cc1ccc(Oc2ccc(Nc3ncnc4ccc(NC5=NC(C)(CO)CO5)cc34)cc2C)cn1]

(4-Methyl-2-{4-[3-methyl-4-(6-methylpyridin-3-yloxy)-phenylamino]-quinazolin-6-ylamino}-4,5-dihydrooxazol-4-yl)-methanol MS ESI (+) m/z 471 (M+1) detected; 1H NMR (400 mHz, CDCl$_3$) δ 8.54 (s, 1H), 8.19 (d, 1H), 8.16 (bs, 1H), 7.72 (m, 2H), 7.58 (dd, 1H), 7.48 (dd, 1H), 7.19 (dd, 1H), 7.13 (d, 1H), 6.95 (d, 1H), 4.39 (d, 1H), 4.01 (d, 1H), 3.42 (s, 2H), 2.52 (s, 3H), 2.29 (s, 3H), 1.39 (s, 3H).

Example 19

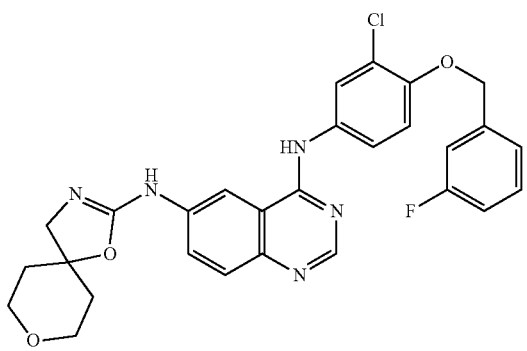 [SMILES: Fc1cccc(COc2ccc(Nc3ncnc4ccc(NC5=NCC6(CCOCC6)O5)cc34)cc2Cl)c1]

N4-[3-Chloro-4-(3-fluorobenzyloxy)-phenyl]-N6-(1,8-dioxa-3-aza-spiro[4.5]dec-2-en-2-yl)-quinazoline-4,6-diamine MS ESI (+) m/z 534 (M+1) detected; $^1$H NMR (400 mHz, CDCl$_3$) δ 8.64 (s, 1H), 8.25 (bs, 1H), 7.78 (m, 2H), 7.60 (bs, 1H), 7.49 (d, 1H), 7.44 (d, 1H), 7.35 (m, 2H), 7.23 (m, 2H), 7.02 (m, 1H), 6.94 (d, 1H), 5.15 (s, 2H), 3.81 (m, 4H), 3.69 (m, 2H), 1.94 (m, 2H), 1.87 (m, 2H).

Example 20

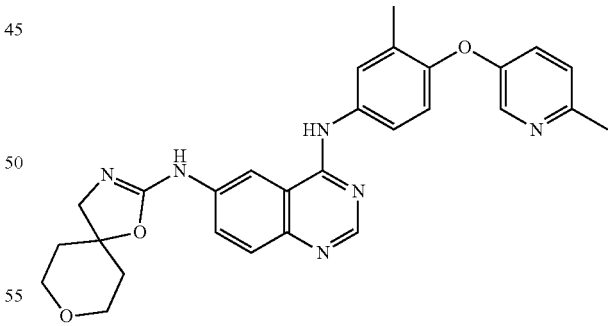

N6-(1,8-Dioxa-3-azaspiro[4.5]dec-2-en-2-yl)-N4-[3-methyl-4-(6-methylpyridin-3-yloxy)-phenyl]-quinazoline-4,6-diamine MS ESI (+) m/z 497 (M+1) detected; $^1$H NMR (400 mHz, CDCl$_3$) δ 8.67 (s, 1H), 8.27 (d, 1H), 7.82 (d, 1H), 7.69 (s, 1H), 7.63 (s, 1H), 7.50 (m, 2H), 7.12 (m, 4H), 6.92 (d, 1H), 3.82 (m, 4H), 3.67 (m, 2H), 2.53 (s, 3H), 2.29 (s, 3H), 1.95 (m, 2H), 1.88 (m, 2H).

Example 21

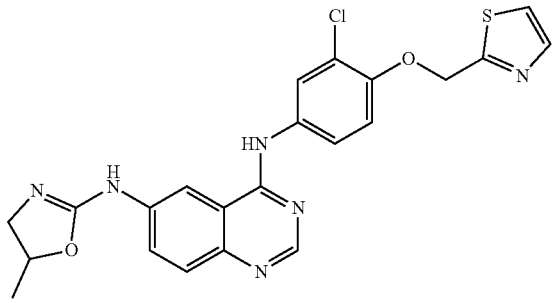 [SMILES: CC1CN=C(Nc2ccc3ncnc(Nc4ccc(OCc5nccs5)c(Cl)c4)c3c2)O1]

N4-[3-Chloro-4-(thiazol-2-ylmethoxy)-phenyl]-N6-(5-methyl-4,5-dihydrooxazol-2-yl)-quinazoline-4,6-diamine MS ESI (+) m/z 467,469 (M+1, Cl pattern) detected; $^1$H NMR (400 mHz, DMSO-D$_6$) δ 9.60 (s, 1H), 8.52 (s, 1H), 8.20 (bs, 1H), 8.13 (s, 1H), 7.93 (d, 1H), 7.87 (d, 1H), 7.82 (d, 1H), 7.71 (d, 2H), 7.38 (d, 1H), 5.60 (s, 2H), 4.82 (m, 1H), 3.80 (m, 1H), 3.26 (m, 1H), 2.56 (s, 3H).

Example 22

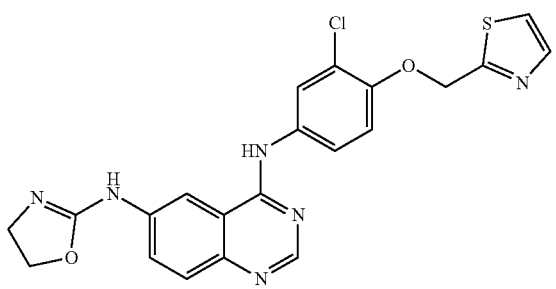 [SMILES: Clc1cc(Nc2ncnc3ccc(NC4=NCCO4)cc23)ccc1OCc1nccs1]

N4-[3-Chloro-4-(thiazol-2-ylmethoxy)-phenyl]-N6-(4,5-dihydro-oxazol-2-yl)-quinazoline-4,6-diamine MS ESI (+) m/z 453, 455 (M+1, Cl pattern) detected; $^1$H NMR (400 mHz, DMSO-D$_6$) δ 9.54 (s, 1H), 8.47 (s, 1H), 8.07 (bs, 1H), 7.86 (d, 1H), 7.80 (d, 1H), 7.76 (d, 1H), 7.66 (m, 2H), 7.32 (d, 1H), 5.55 (s, 2H), 4.38 (m, 2H), 3.62 (m, 1H), 3.18 (m, 1H).

Example 23

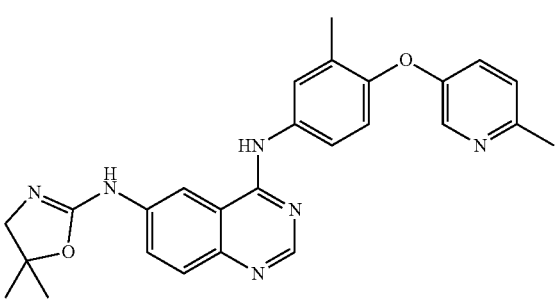 [SMILES: Cc1ccc(Oc2ccc(Nc3ncnc4ccc(NC5=NCC(C)(C)O5)cc34)cc2C)cn1]

N6-(5,5-Dimethyl-4,5-dihydrooxazol-2-yl)-N4-[3-methyl-4-(6-methylpyridin-3-yloxy)-phenyl]-quinazoline-4,6-diamine MS APCI (+) m/z 455 (M+1) detected; $^1$H NMR (400 mHz, CD$_3$OD) δ 8.42 (s, 1H), 8.17 (bs, 1H), 8.12 (d, 1H), 7.70 (d, 1H), 7.69 (s, 1H), 7.61 (dd, 1H), 7.57 (dd, 1H), 7.28 (m, 2H), 6.98 (d, 1H), 3.64 (s, 2H), 2.50 (s, 3H), 2.26 (s, 3H), 1.51 (s, 6H).

Example 24

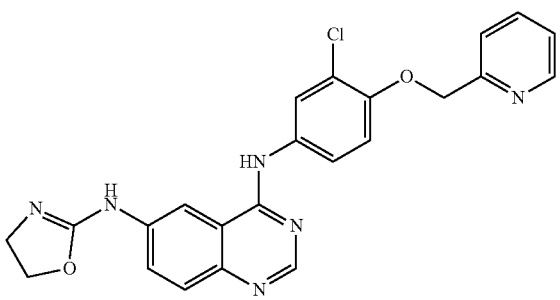 [SMILES: Clc1cc(Nc2ncnc3ccc(NC4=NCCO4)cc23)ccc1OCc1ccccn1]

N4-[3-Chloro-4-(pyridin-2-ylmethoxy)-phenyl]-N6-(4,5-dihydrooxazol-2-yl)-quinazoline-4,6-diamine MS ESI (+) m/z 447, 449 (M+1, Cl pattern) detected; $^1$H NMR (400 mHz, DMSO-D$_6$) δ 9.53 (bs, 1H), 8.59 (d, 1H), 8.45 (s, 1H), 8.05 (bs, 1H), 7.89 (m, 2H), 7.74 (d, 1H), 7.65 (d, 1H), 7.58 (d, 1H), 7.38 (dd, 1H), 7.25 (d, 1H), 5.29 (s, 2H), 4.38 (m, 2H), 3.62 (m, 2H).

Example 25

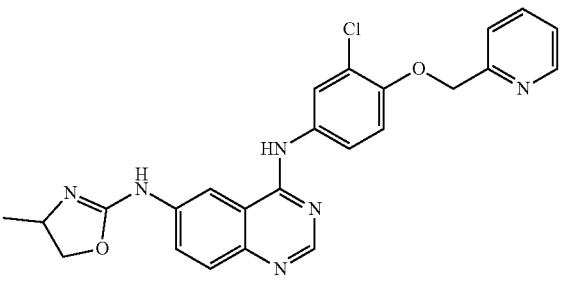 [SMILES: CC1COC(Nc2ccc3ncnc(Nc4ccc(OCc5ccccn5)c(Cl)c4)c3c2)=N1]

N4-[3-Chloro-4-(pyridin-2-ylmethoxy)-phenyl]-N6-(4-methyl-4,5-dihydrooxazol-2-yl)-quinazoline-4,6-diamine MS ESI (+) m/z 461, 463 (M+1, Cl pattern) detected; $^1$H NMR (400 mHz, DMSO-D$_6$) δ 9.51 (bs, 1H), 8.58 (d, 1H), 8.44 (s, 1H), 8.04 (bs, 1H), 7.86 (m, 1H), 7.72 (d, 1H), 7.58 (m, 3H), 7.34 (m, 1H), 7.22 (d, 1H), 5.27 (s, 2H), 4.74 (m, 1H), 3.72 (m, 1H), 3.15 (m, 1H), 1.32 (s, 3H).

Example 26

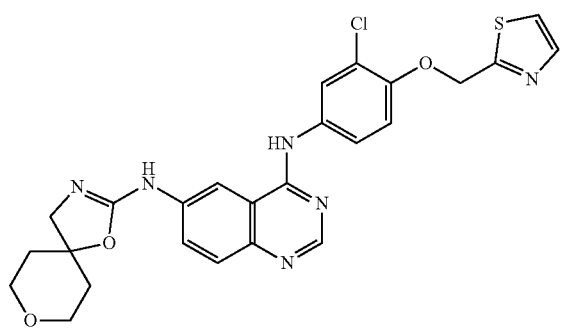 [SMILES: Clc1cc(Nc2ncnc3ccc(NC4=NCC5(CCOCC5)O4)cc23)ccc1OCc1nccs1]

N4-[3-Chloro-4-(thiazol-2-ylmethoxy)-phenyl]-N6-(1,8-dioxa-3-aza-spiro[4.5]dec-2-en-2-yl)-quinazoline-4,6-diamine MS ESI (+) m/z 523, 525 (M+1, Cl pattern) detected; $^1$H NMR (400 mHz, CDCl$_3$) δ 8.64 (s, 1H), 7.78 (m, 2H), 7.60 (bs, 1H), 7.50 (d, 1H), 7.43 (d, 1H), 7.35 (m, 1H), 7.23 (m, 2H), 7.02 (m, 1H), 6.95 (d, 1H), 5.15 (s, 2H), 3.81 (m, 4H), 3.69 (m, 2H), 1.94 (m, 2H), 1.87 (m, 2H).

Example 27

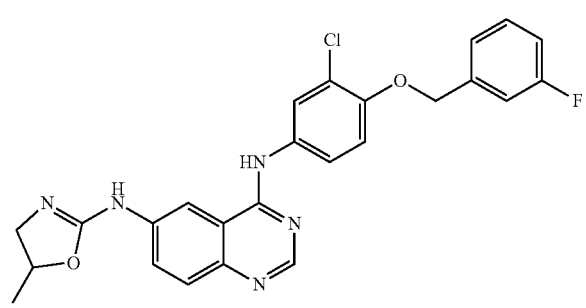 [SMILES: CC1CN=C(Nc2ccc3ncnc(Nc4ccc(OCc5cccc(F)c5)c(Cl)c4)c3c2)O1]

N4-[3-Chloro-4-(3-fluorobenzyloxy)-phenyl]-N6-(5-methyl-4,5-dihydrooxazol-2-yl)-quinazoline-4,6-diamine $^1$H NMR (400 mHz, CD$_3$OD) δ 8.50 (s, 1H), 8.12 (bs, 1H), 8.02 (d, 1H), 7.97 (d, 1H), 7.60 (dd, 1H), 7.44 (m, 2H), 7.34 (d, 1H), 7.29 (d, 1H), 7.14 (d, 1H), 7.10 (d, 1H), 5.22 (s, 2H), 4.79 (m, 1H), 3.87 (m, 1H), 3.36 (m, 1H), 1.40 (d, 3H).

Example 28

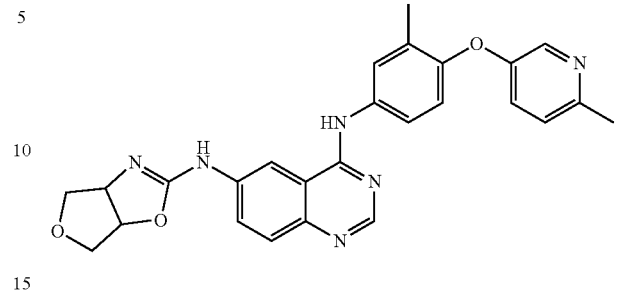

N4-[3-Methyl-4-(6-methyl pyridin-3-yloxy)-phenyl]-N6-(3a,4,6,6a-tetrahydrofuro[3,4-d]oxazol-2-yl)-quinazoline-4,6-diamine MS APCI (+) m/z 469 (M+1) detected; $^1$H NMR (400 mHz, CD$_3$OD) δ 8.43 (s, 1H), 8.26 (bs, 1H), 8.13 (d, 1H), 7.70 (m, 3H), 7.62 (m, 2H), 7.29 (m, 2H), 7.08 (s, 1H), 7.00 (d, 1H), 5.25 (m, 1H), 4.82 (m, 1H), 4.17 (d, 1H), 4.02 (d, 1H), 3.64 (m, 2H), 2.50 (s, 3H), 2.27 (s, 3H).

Example 29

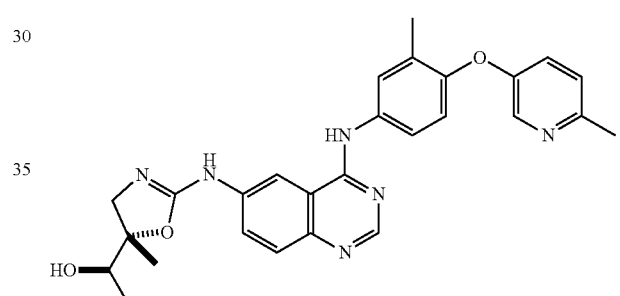

(1RS, 5SR)-1-(5-methyl-2-(4-(3-methyl-4-(6-methylpyridin-3-yloxy)phenylamino)quinazolin-6-ylamino)-4,5-dihydrooxazol-5-yl)ethanol MS ESI (+) m/z 485 (M+1) detected; $^1$H NMR (400 mHz, CDCl$_3$) δ 8.58 (s, 1H), 8.22 (d, 1H), 8.17 (bs, 1H), 7.74 (d, 1H), 7.71 (d, 1H), 7.60 (dd, 1H), 7.36 (d, 1H), 7.16 (dd, 1H), 7.10 (d, 1H), 6.94 (d, 1H), 4.02 (d, 1H), 3.92 (m, 1H), 3.55 (d, 1H), 2.52 (s, 3H), 2.28 (s, 3H), 1.45 (s, 3H), 1.22 (m, 4H).

Example 30

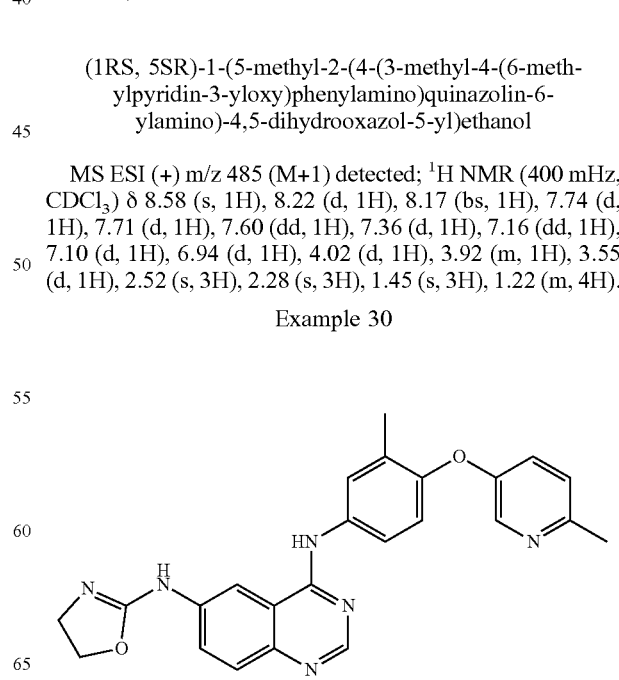

N6-(4,5-Dihydrooxazol-2-yl)-N4-[3-methyl-4-(6-methylpyridin-3-yloxy)-phenyl]-quinazoline-4,6-diamine MS ESI (+) m/z 427 (M+1) detected; $^1$H NMR (400 mHz, DMSO-D$_6$) δ 9.53 (s, 1H), 8.45 (s, 1H), 8.18 (d, 1H), 7.80 (s, 1H), 7.72 (d, 1H), 7.65 (d, 1H), 7.21 (m, 3H), 6.96 (d, 1H), 4.38 (m, 2H), 3.64 (m, 2H), 2.51 (s, 3H), 2.20 (s, 3H).

Example 31

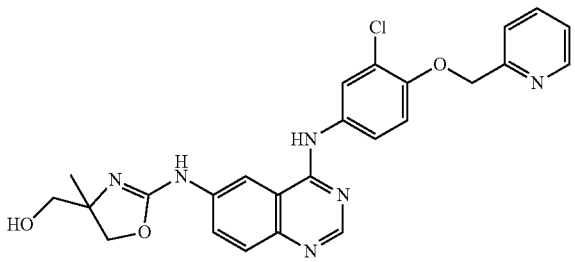 [SMILES: CC1(CO)COC(Nc2ccc3ncnc(Nc4ccc(OCc5ccccn5)c(Cl)c4)c3c2)=N1]

(2-{4-[3-Chloro-4-(pyridin-2-ylmethoxy)-phenylamino]-quinazolin-6-ylamino}-4-methyl-4,5-dihydro-oxazol-4-yl)-methanol MS ESI (+) m/z 491, 493 (M+1, Cl pattern) detected; $^1$H NMR (400 mHz, CDCl$_3$) δ 8.57 (s, 1H), 8.56 (s, 1H), 8.13 (bs, 1H), 7.97 (d, 1H), 7.81 (m, 1H), 7.73 (m, 2H), 7.61 (dd, 1H), 7.44 (dd, 1H), 7.29 (m, 1H), 7.04 (d, 1H), 5.30 (s, 2H), 3.64 (d, 1H), 3.52 (d, 1H), 3.43 (s, 2H), 1.26 (s, 3H).

Example 32

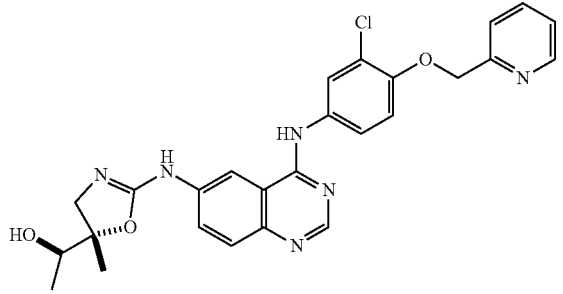 [SMILES: C[C@@H](O)[C@]1(C)CN=C(Nc2ccc3ncnc(Nc4ccc(OCc5ccccn5)c(Cl)c4)c3c2)O1]

(1RS, 5SR)-1-(2-(4-(3-chloro-4-(pyridin-2-yl-methoxy)phenylamino)quinazolin-6-ylamino)-5-methyl-4,5-dihydrooxazol-5-yl)ethanol MS ESI (+) m/z 505, 507 (M+1, Cl pattern) detected; $^1$H NMR (400 mHz, CDCl$_3$) δ 8.60 (s, 1H), 8.58 (s, 1H), 8.12 (bs, 1H), 7.95 (d, 1H), 7.77 (m, 1H), 7.72 (d, 1H), 7.69 (d, 1H), 7.63 (dd, 1H), 7.25 (m, 2H), 7.02 (d, 1H), 5.30 (s, 2H), 4.07 (d, 1H), 3.98 (q, 1H), 3.56 (d, 1H), 1.45 (s, 3H), 1.22 (d, 3H).

Example 33

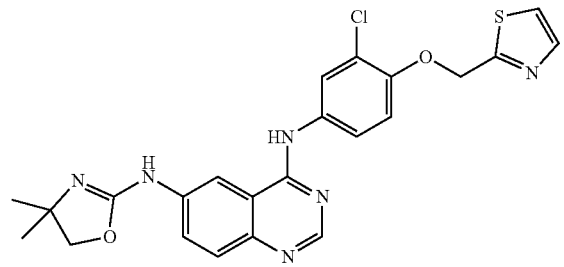 [SMILES: CC1(C)COC(Nc2ccc3ncnc(Nc4ccc(OCc5nccs5)c(Cl)c4)c3c2)=N1]

N4-[3-Chloro-4-(thiazol-2-ylmethoxy)-phenyl]-N6-(4,4-dimethyl-4,5-dihydrooxazol-2-yl)-quinazoline-4,6-diamine MS APCI (+) m/z 481, 483 (M+1, Cl pattern) detected; $^1$H NMR (400 mHz, DMSO-D$_6$) δ 9.52 (s, 1H), 8.47 (s, 1H), 8.09 (s, 1H), 7.96 (bs, 1H), 7.86 (d, 1H), 7.81 (d, 1H), 7.78 (d, 1H), 7.65 (d, 1H), 7.32 (d, 1H), 5.55 (s, 2H), 3.17 (d, 2H), 1.28 (s, 6H).

Example 34

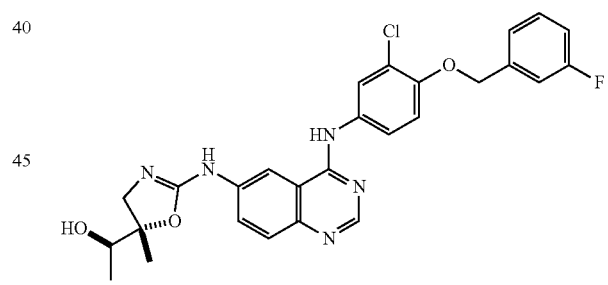

(1-RS, 5SR)-1-(2-(4-(4-(3-fluorobenzyloxy)-3-chlorophenyl amino)quinazolin-6-ylamino)-5-methyl-4,5-dihydrooxazol-5-yl)ethanol MS ESI (+) m/z 522, 524 (M+1, Cl pattern) detected; $^1$H NMR (400 mHz, CDCl$_3$) δ 8.57 (s, 1H), 8.10 (bs, 1H), 7.91 (d, 1H), 7.70 (d, 1H), 7.65 (dd, 1H), 7.36 (m, 1H), 7.30 (m, 1H), 7.24 (m, 2H), 7.00 (m, 1H), 6.98 (d, 1H), 5.16 (s, 2H), 4.05 (d, 1H), 3.95 (q, 1H), 3.55 (d, 1H), 1.45 (s, 3H), 1.21 (d, 3H).

Example 35

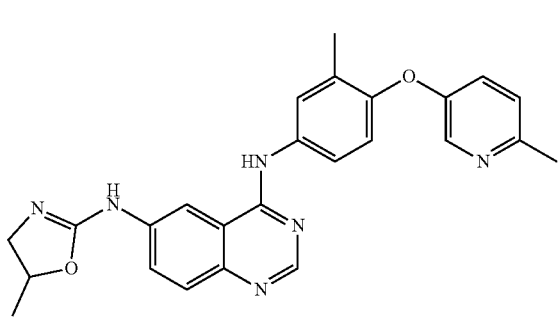 [SMILES: Cc1ccc(Oc2ccc(Nc3ncnc4ccc(NC5=NCC(C)O5)cc34)cc2C)cn1]

N6-(5-Methyl-4,5-dihydrooxazol-2-yl)-N4-[3-methyl-4-(6-methylpyridin-3-yloxy)-phenyl]-quinazoline-4,6-diamine MS APCI (+) m/z 441 (M+1) detected; $^1$H NMR (400 mHz, DMSO-D$_6$) δ 9.51 (s, 1H), 8.45 (s, 1H), 8.18 (d, 1H), 7.80 (s, 1H), 7.69 (m, 3H), 7.23 (m, 2H), 6.96 (d, 1H), 4.77 (m, 1H), 4.13 (m, 1H), 6.73 (m, 1H), 2.44 (s, 3H), 2.20 (s, 3H), 1.36 (d, 3H).

Example 36

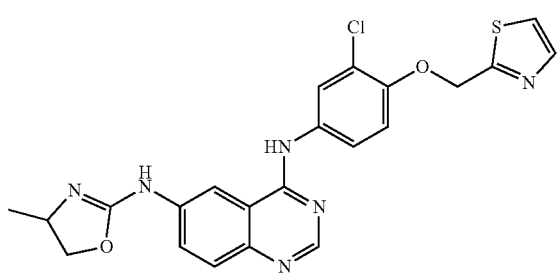 [SMILES: CC1COC(Nc2ccc3ncnc(Nc4ccc(OCc5nccs5)c(Cl)c4)c3c2)=N1]

N4-[3-Chloro-4-(thiazol-2-ylmethoxy)-phenyl]-N6-(4-methyl-4,5-dihydrooxazol-2-yl)-quinazoline-4,6-diamine MS APCI (+) m/z 467, 469 (M+1, Cl pattern) detected; $^1$H NMR (400 mHz, DMSO-D$_6$) δ 9.53 (s, 1H), 8.47 (s, 1H), 8.09 (s, 1H), 7.86 (d, 1H), 7.81 (d, 1H), 7.77 (d, 1H), 7.69 (m, 3H), 7.32 (d, 1H), 7.02 (s, 1H), 5.54 (s, 2H), 4.47 (m, 1H), 3.99 (m, 1H), 3.90 (m, 1H), 1.18 (d, 3H).

Example 37

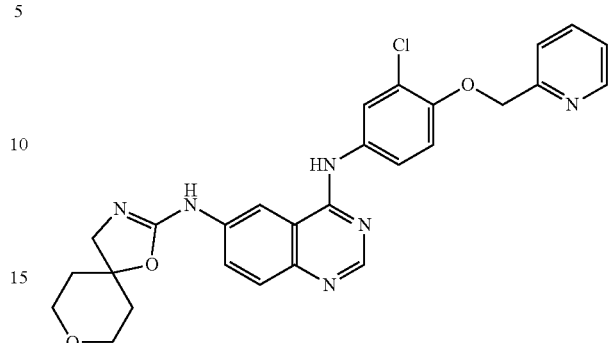

N4-[3-Chloro-4-(pyridin-2-ylmethoxy)-phenyl]-N6-(1,8-dioxa-3-aza-spiro[4.5]dec-2-en-2-yl)-quinazoline-4,6-diamine MS APCI (+) m/z 517, 519 (M+1, Cl pattern) detected; $^1$H NMR (400 mHz, CDCl$_3$) δ 8.66 (s, 1H), 8.60 (d, 1H), 7.87 (s, 1H), 7.81 (d, 1H), 7.76 (m, 1H), 7.66 (d, 1H), 7.51 (m, 2H), 7.44 (d, 1H), 7.25 (m, 1H), 7.01 (d, 1H), 5.30 (s, 2H), 3.82 (m, 4H), 3.75 (m, 1H), 3.69 (m, 1H), 1.95 (m, 2H), 1.87 (m, 2H).

Example 38

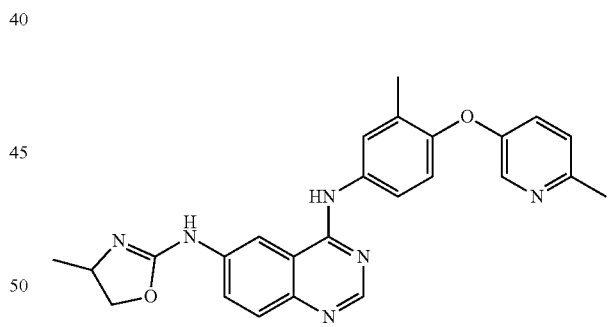

N6-(4-Methyl-4,5-dihydrooxazol-2-yl)-N4-[3-methyl-4-(6-methylpyridin-3-yloxy)-phenyl]-quinazoline-4,6-diamine MS APCI (+) m/z 441 (M+1) detected; $^1$H NMR (400 mHz, DMSO-D$_6$) δ 9.51 (s, 1H), 8.44 (s, 1H), 8.15 (d, 1H), 8.05 (bs, 1H), 7.79 (s, 1H), 7.71 (d, 1H), 7.62 (m, 2H), 7.20 (m, 2H), 6.99 (s, 1H), 6.93 (d, 1H), 4.45 (m, 1H), 4.02 (m, 1H), 3.87 (m, 1H), 2.41 (s, 3H), 2.18 (s, 3H), 1.17 (d, 3H).

Example 39

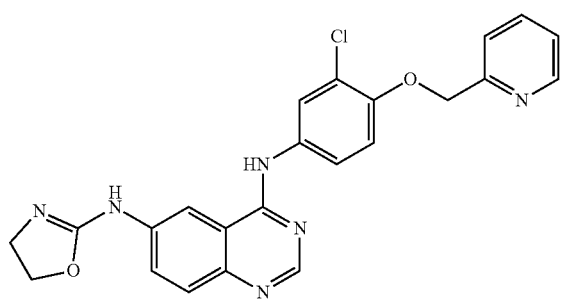 [SMILES: Clc1cc(Nc2ncnc3ccc(NC4=NCCO4)cc23)ccc1OCc1ccccn1]

N4-[3-Chloro-4-(pyridin-2-ylmethoxy)-phenyl]-N6-(4,5-dihydrooxazol-2-yl)-quinazoline-4,6-diamine MS ESI (+) m/z 447, 449 (M+1, Cl pattern) detected; $^1$H NMR (400 mHz, DMSO-D$_6$) δ 9.53 (bs, 1H), 8.59 (d, 1H), 8.45 (s, 1H), 8.05 (bs, 1H), 7.89 (m, 2H), 7.74 (d, 1H), 7.65 (d, 1H), 7.58 (d, 1H), 7.38 (dd, 1H), 7.25 (d, 1H), 5.29 (s, 2H), 4.38 (m, 2H), 3.62 (m, 2H).

Example 40

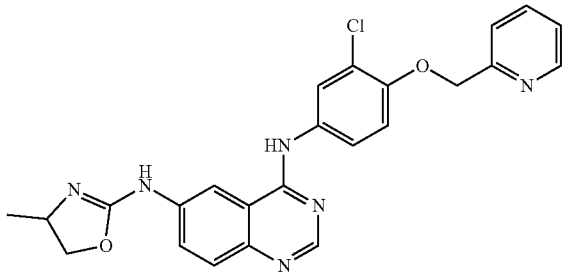 [SMILES: CC1COC(Nc2ccc3ncnc(Nc4ccc(OCc5ccccn5)c(Cl)c4)c3c2)=N1]

N4-[3-Chloro-4-(pyridin-2-ylmethoxy)-phenyl]-N6-(4-methyl-4,5-dihydrooxazol-2-yl)-quinazoline-4,6-diamine MS ESI (+) m/z 461, 463 (M+1, Cl pattern) detected; $^1$H NMR (400 mHz, DMSO-D$_6$) δ 9.51 (bs, 1H), 8.58 (d, 1H), 8.44 (s, 1H), 8.04 (bs, 1H), 7.86 (m, 1H), 7.72 (d, 1H), 7.58 (m, 3H), 7.34 (m, 1H), 7.22 (d, 1H), 5.27 (s, 2H), 4.74 (m, 1H), 3.72 (m, 1H), 3.15 (m, 1H), 1.32 (s, 3H).

Example 41

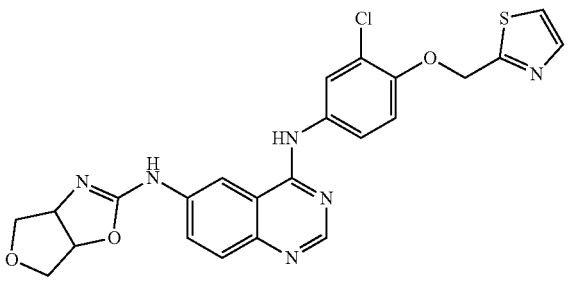 [SMILES: Clc1cc(Nc2ncnc3ccc(NC4=NC5COCC5O4)cc23)ccc1OCc1nccs1]

N4-[3-Chloro-4-(thiazol-2-ylmethoxy)-phenyl]-N6-(3a,4,6,6a-tetrahydrofuro[3,4-d]oxazol-2-yl)-quinazoline-4,6-diamine MS APCI (+) m/z 495, 497 (M+1, Cl pattern) detected; $^1$H NMR (400 mHz, CD$_3$OD) δ 8.47 (s, 1H), 8.23 (br. s, 1H), 7.95 (d, 1H), 7.83 (d, 1H), 7.71 (d, 1H), 7.66 (dd, 1H), 7.63 (d, 1H), 7.59 (dd, 1H), 7.21 (d, 1H), 5.50 (s, 2H), 4.19 (d, 1H), 4.05 (d, 1H), 3.65 (m, 2H), 3.19 (m, 2H).

Example 42

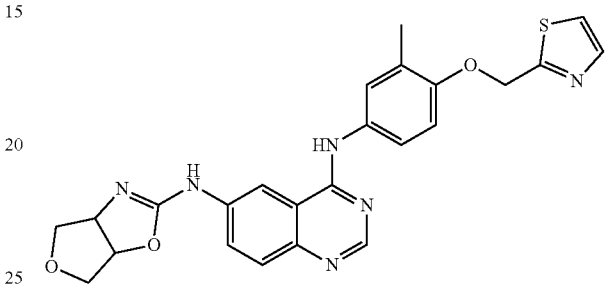

N4-[3-Methyl-4-(thiazol-2-ylmethoxy)-phenyl]-N6-(3a,4,6,6a-tetrahydrofuro[3,4-d]oxazol-2-yl)-quinazoline-4,6-diamine MS ESI (+) m/z 475 (M+1) detected; $^1$H NMR (400 mHz, CD$_3$OD) δ 8.37 (s, 1H), 8.25 (br s, 1H), 7.83 (d, 1H), 7.69 (d, 1H), 7.65 (d, 1H), 7.59 (m, 1H), 7.52 (m, 2H), 7.07 (d, 1H), 5.46 (s, 2H), 4.17 (d, 1H), 4.02 (d, 1H), 3.64 (m, 2H), 2.34 (m, 5H).

Example 43

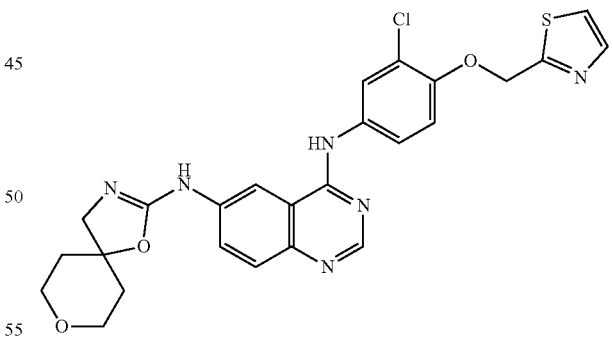

N4-[3-Chloro-4-(thiazol-2-ylmethoxy)-phenyl]-N6-(1,8-dioxa-3-aza-spiro[4.5]dec-2-en-2-yl)-quinazoline-4,6-diamine MS ESI (+) m/z 523, 525 (M+1, Cl pattern) detected; $^1$H NMR (400 mHz, CDCl$_3$) δ 8.64 (s, 1H), 7.78 (m, 2H), 7.60 (bs, 1H), 7.50 (d, 1H), 7.43 (d, 1H), 7.35 (m, 1H), 7.23 (m, 2H), 7.02 (m, 1H), 6.95 (d, 1H), 5.15 (s, 2H), 3.81 (m, 4H), 3.69 (m, 2H), 1.94 (m, 2H), 1.87 (m, 2H).

Example 44

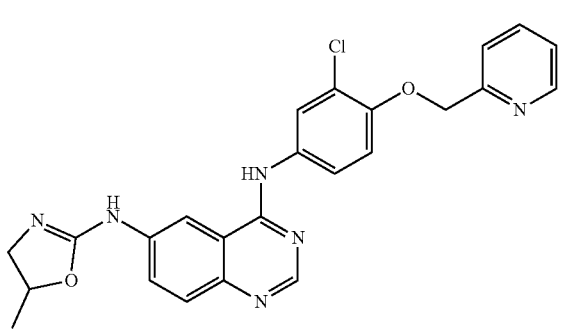 [SMILES: CC1CN=C(Nc2ccc3ncnc(Nc4ccc(OCc5ccccn5)c(Cl)c4)c3c2)O1]

N4-[3-Chloro-4-(pyridin-2-ylmethoxy)-phenyl]-N6-(5-methyl-4,5-dihydrooxazol-2-yl)-quinazoline-4,6-diamine MS ESI (+) m/z 461, 463 (M+1, Cl pattern) detected; $^1$H NMR (400 mHz, DMSO-D$_6$) δ 9.51 (s, 1H), 8.58 (s, 1H), 8.44 (s, 1H), 8.04 (m, 2H), 7.86 (m, 1H), 7.63 (m, 4H), 7.34 (m, 1H), 7.22 (d, 1H), 5.27 (s, 2H), 4.74 (m, 1H), 3.72 (m, 1H), 3.15 (m, 1H), 1.34 (d, 3H).

Example 45

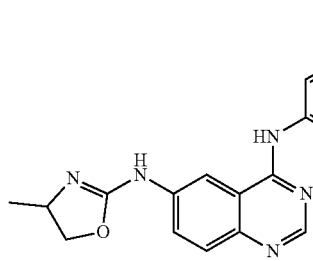

N4-[3-Chloro-4-(3-fluorobenzyloxy)-phenyl]-N6-(4-methyl-4,5-dihydrooxazol-2-yl)-quinazoline-4,6-diamine MS ESI (+) m/z 478 (M+1) detected; 41 NMR (400 mHz, DMSO-D$_6$) δ 9.51 (s, 1H), 8.46 (s, 1H), 8.06 (m, 2H), 7.76 (d, 1H), 7.64 (d, 1H), 7.47 (m, 2H), 7.32 (m, 2H), 7.24 (d, 1H), 7.18 (m, 1H), 5.25 (s, 2H), 4.47 (m, 1H), 3.95 (m, 1H), 3.17 (m, 1H), 1.19 (d, 3H).

Example 46

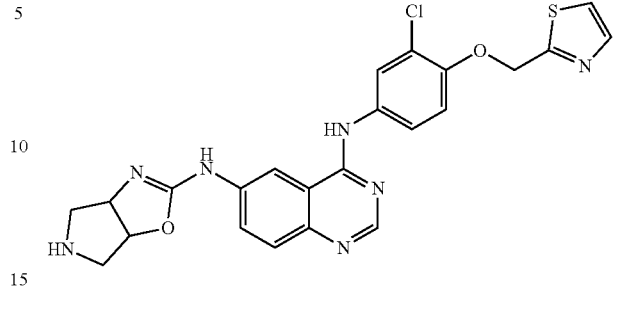

N4-[3-Chloro-4-(thiazol-2-ylmethoxy)-phenyl]-N6-(4,5,6,6a-tetrahydro-3aH-pyrrolo[3,4-d]oxazol-2-yl)-quinazoline-4,6-diamine N4-[3-Chloro-4-(thiazol-2-ylmethoxy)-phenyl]-N6-(4,5,6,6a-tetrahydro-3aH-pyrrolo[3,4-d]oxazol-2-yl)-quinazoline-4,6-diamine is prepared from 2-{4-[3-chloro-4-(thiazol-2-ylmethoxy)-phenylamino]-quinazolin-6-ylamino}-3a,4,6,6a-tetrahydro-pyrrolo[3,4-d]oxazole-5-carboxylic acid tert-butyl ester by standard BOC deprotection methods using TFA in methylene chloride. MS APCI (+) m/z 494, 496 (M+1, Cl pattern) detected; $^1$H NMR (400 mHz, CD$_3$OD) δ 8.44 (s, 1H), 8.19 (br. s, 1H), 7.96 (d, 1H), 7.83 (d, 1H), 7.67 (m, 3H), 7.58 (dd, 1H), 7.22 (d, 1H), 5.50 (s, 2H), 5.17 (m, 1H), 4.76 (m, 1H), 3.32 (d, 1H), 3.16 (d, 1H), 2.85 (m, 2H).

Example 47

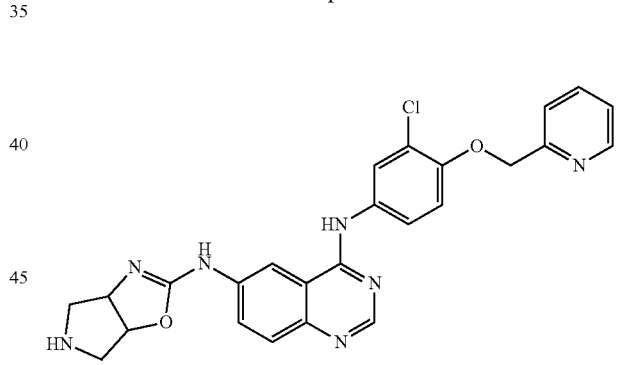

N4-[3-Chloro-4-(pyridin-2-ylmethoxy)-phenyl]-N6-(4,5,6,6a-tetrahydro-3aH-pyrrolo[3,4-d]oxazol-2-yl)-quinazoline-4,6-diamine N4-[3-Chloro-4-(pyridin-2-ylmethoxy)-phenyl]-N6-(4,5,6,6a-tetrahydro-3aH-pyrrolo[3,4-d]oxazol-2-yl)-quinazoline-4,6-diamine is prepared from 2-{4-[3-Chloro-4-(pyridin-2-ylmethoxy)-phenylamino]-quinazolin-6-ylamino}-3a,4,6,6a-tetrahydro-pyrrolo[3,4-d]oxazole-5-carboxylic acid tert-butyl ester by standard BOC deprotection methods using TFA in methylene chloride. MS APCI (+) m/z 488, 490 (M+1, Cl pattern) detected; $^1$H NMR (400 mHz, CD$_3$OD) δ 8.56 (d, 1H), 8.44 (s, 1H), 8.21 (br. s, 1H), 7.91 (m, 2H), 7.70 (m, 2H), 7.63 (d, 1H), 7.57 (d, 1H), 7.39 (m, 1H), 7.16 (d, 1H), 5.28 (s, 2H), 5.17 (m, 1H), 4.78 (m, 1H), 3.34 (d, 1H), 3.16 (d, 1H), 2.84 (m, 2H).

Example 48

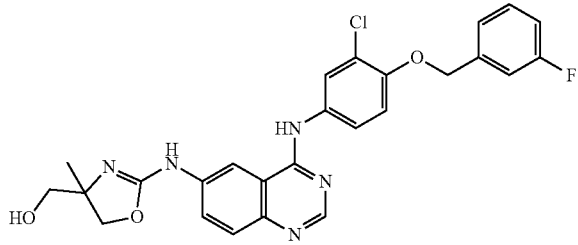 [SMILES: CC1(CO)COC(Nc2ccc3ncnc(Nc4ccc(OCc5cccc(F)c5)c(Cl)c4)c3c2)=N1]

(2-{4-[3-Chloro-4-(3-fluorobenzyloxy)-phenylamino]-quinazolin-6-ylamino}-4-methyl-4,5-dihydro-oxazol-4-yl)-methanol MS ESI (+) m/z 508, 510 (M+1, Cl pattern) detected; $^1$H NMR (400 mHz, CDCl$_3$) δ 8.57 (s, 1H), 8.14 (s, 1H), 7.93 (d, 1H), 7.74 (d, 1H), 7.63 (dd, 1H), 7.37 (m, 2H), 7.25 (m, 2H), 7.01 (m, 2H), 5.17 (s, 2H), 4.38 (d, 1H), 4.00 (d, 1H), 3.65 (d, 1H), 3.48 (d, 1H), 1.38 (s, 3H).

Example 49

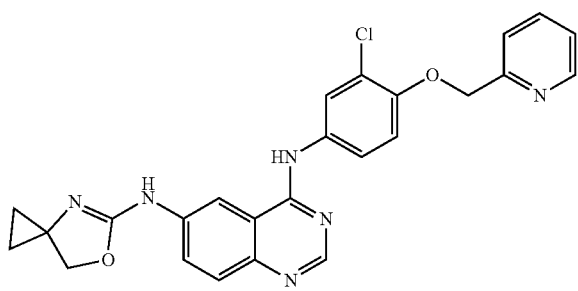 [SMILES: Clc1cc(Nc2ncnc3ccc(NC4=NC5(CC5)CO4)cc23)ccc1OCc1ccccn1]

N4-[3-Chloro-4-(pyridin-2-ylmethoxy)-phenyl]-N6-(6-oxa-4-aza-spiro[2.4]hept-4-en-5-yl)-quinazoline-4,6-diamine MS APCI (+) m/z 473, 475 (M+1, Cl pattern) detected; $^1$H NMR (400 mHz, CD$_3$OD) δ 8.56 (d, 1H), 8.45 (s, 1H), 8.21 (s, 1H), 7.98 (d, 1H), 7.92 (m, 1H), 7.72 (m, 2H), 7.63 (m, 2H), 7.40 (m, 1H), 7.18 (d, 1H), 5.28 (s, 2H), 4.36 (s, 2H), 1.12 (m, 2H), 0.81 (m, 2H).

Example 50

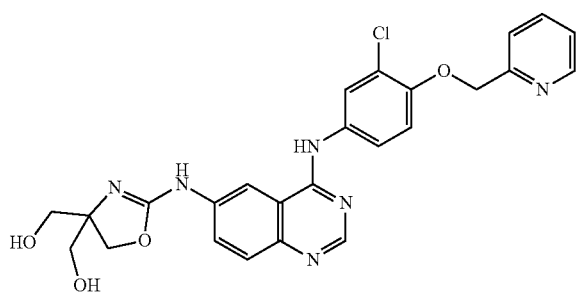 [SMILES: OCC1(CO)COC(Nc2ccc3ncnc(Nc4ccc(OCc5ccccn5)c(Cl)c4)c3c2)=N1]

(2-{4-[3-Chloro-4-(pyridin-2-ylmethoxy)-phenylamino]-quinazolin-6-ylamino}-4-hydroxymethyl-4,5-dihydro-oxazol-4-yl)-methanol MS ESI (+) m/z 507, 509 (M+1, Cl pattern) detected; $^1$H NMR (400 mHz, DMSO-D$_6$) δ 9.47 (s, 1H), 8.60 (d, 1H), 8.46 (s, 1H), 8.08 (s, 1H), 7.89 (m, 1H), 7.71 (m, 2H), 7.58 (d, 1H), 7.37 (m, 1H), 7.25 (d, 1H), 5.29 (s, 2H), 4.34 (m, 2H), 3.29 (s, 4H).

Example 51

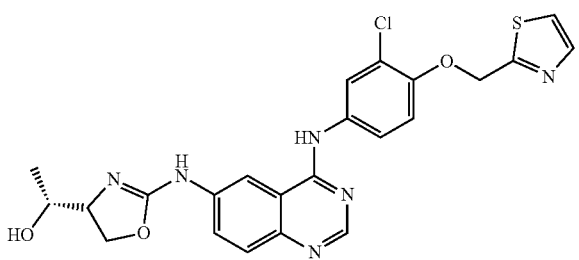 [SMILES: C[C@@H](O)C1COC(Nc2ccc3ncnc(Nc4ccc(OCc5nccs5)c(Cl)c4)c3c2)=N1]

(R)-1-((S)-2-(4-(3-chloro-4-(thiazol-2-ylmethoxy)phenylamino)quinazolin-6-ylamino)-4,5-dihydrooxazol-4-yl)ethanol (R)-1-((S)-2-(4-(3-chloro-4-(thiazol-2-ylmethoxy)phenylamino)quinazolin-6-ylamino)-4,5-dihydrooxazol-4-yl) ethanol is prepared from (1R, 4S)-N6-[4-(1-tert-butoxyethyl)-4,5-dihydrooxazol-2-yl]-N4-[3-chloro-4-(thiazol-2-ylmethoxy)-phenyl]-quinazoline-4,6-diamine by standard deprotection methods using TFA in methylene chloride. MS ESI (+) m/z 497, 499 (M+1, Cl pattern) detected; $^1$H NMR (400 mHz, DMSO-D$_6$) δ 9.53 (s, 1H), 8.47 (s, 1H), 8.08 (d, 1H), 7.87 (d, 1H), 7.80 (d, 1H), 7.76 (dd, 1H), 7.66 (m, 2H), 7.33 (d, 1H), 5.55 (s, 2H), 4.81 (m, 1H), 4.37 (m, 1H), 4.20 (m, 1H), 3.83 (m, 1H), 3.63 (m, 1H), 1.06 (d, 3H).

Example 52

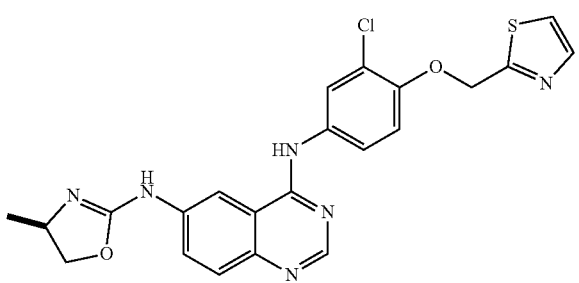

(R)-N4-[3-Chloro-4-(thiazol-2-ylmethoxy)-phenyl]-N6-(4-methyl-4,5-dihydro-oxazol-2-yl)-quinazoline-4,6-diamine Prepared using (R)-2-aminopropan-1-ol. MS APCI (+) m/z 467, 469 (M+1, Cl pattern) detected; $^1$H NMR (400 mHz, DMSO-D$_6$) δ 9.53 (s, 1H), 8.47 (s, 1H), 8.09 (s, 1H), 7.86 (d, 1H), 7.81 (d, 1H), 7.77 (d, 1H), 7.69 (m, 3H), 7.32

(d, 1H), 7.02 (s, 1H), 5.54 (s, 2H), 4.47 (m, 1H), 3.99 (m, 1H), 3.90 (m, 1H), 1.18 (d, 3H).

Example 53

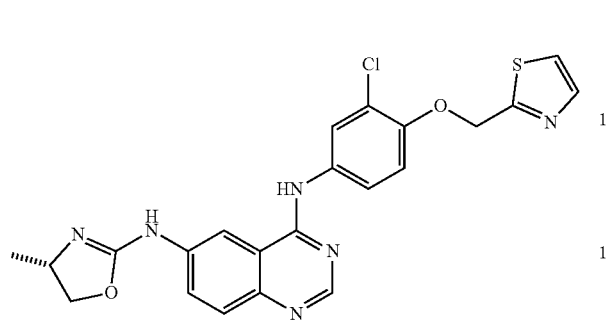

(S)-N4-[3-Chloro-4-(thiazol-2-ylmethoxy)-phenyl]-N6-(4-methyl-4,5-dihydro-oxazol-2-yl)-quinazoline-4,6-diamine Prepared using (S)-2-amino-propan-1-ol. MS APCI (+) m/z 467, 469 (M+1, Cl pattern) detected; $^1$H NMR (400 mHz, DMSO-D$_6$) δ 9.53 (s, 1H), 8.47 (s, 1H), 8.09 (s, 1H), 7.86 (d, 1H), 7.81 (d, 1H), 7.77 (d, 1H), 7.69 (m, 3H), 7.32 (d, 1H), 7.02 (s, 1H), 5.54 (s, 2H), 4.47 (m, 1H), 3.99 (m, 1H), 3.90 (m, 1H), 1.18 (d, 3H).

Example 54

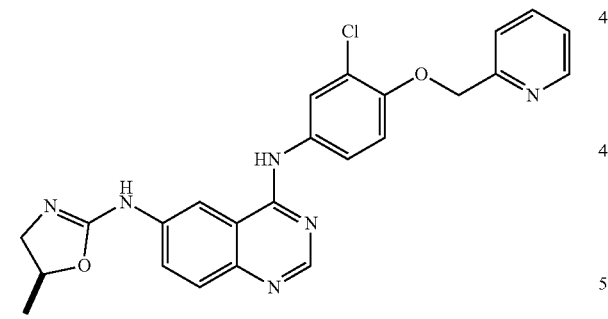

(S)-N4-[3-Chloro-4-(pyridin-2-ylmethoxy)-phenyl]-N6-(5-methyl-4,5-dihydro-oxazol-2-yl)-quinazoline-4,6-diamine Prepared using (S)-1-amino-propan-2-ol. MS ESI (+) m/z 461, 463 (M+1, Cl pattern) detected; $^1$H NMR (400 mHz, DMSO-D$_6$) δ 9.51 (s, 1H), 8.58 (s, 1H), 8.44 (s, 1H), 8.04 (m, 2H), 7.86 (m, 1H), 7.63 (m, 4H), 7.34 (m, 1H), 7.22 (d, 1H), 5.27 (s, 2H), 4.74 (m, 1H), 3.72 (m, 1H), 3.15 (m, 1H), 1.34 (d, 3H).

Example 55

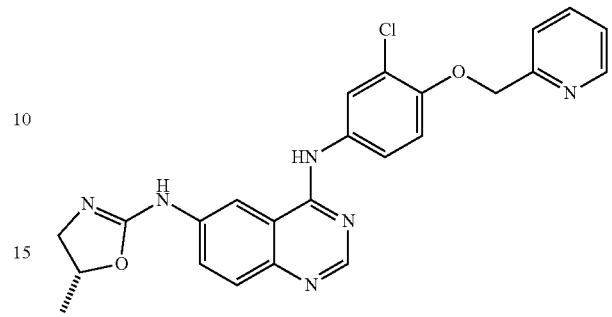

(R)-N4-[3-Chloro-4-(pyridin-2-ylmethoxy)-phenyl]-N6-(5-methyl-4,5-dihydro-oxazol-2-yl)-quinazoline-4,6-diamine Prepared using (R)-1-amino-propan-2-ol. MS ESI (+) m/z 461, 463 (M+1, Cl pattern) detected; $^1$H NMR (400 mHz, DMSO-D$_6$) δ 9.51 (s, 1H), 8.58 (s, 1H), 8.44 (s, 1H), 8.04 (m, 2H), 7.86 (m, 1H), 7.63 (m, 4H), 7.34 (m, 1H), 7.22 (d, 1H), 5.27 (s, 2H), 4.74 (m, 1H), 3.72 (m, 1H), 3.15 (m, 1H), 1.34 (d, 3H).

Example 56

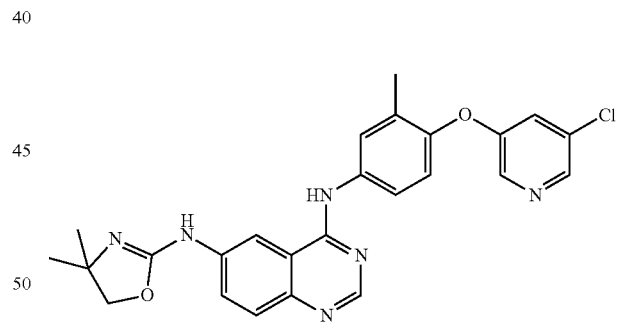

N4-[4-(5-Chloropyridin-3-yloxy)-3-methyl-phenyl]-N6-(4,4-dimethyl-4,5-dihydro-oxazol-2-yl)-quinazoline-4,6-diamine MS ESI (+) m/z 475 477 (m+1, Cl pattern) detected; $^1$H NMR (400 mHz, DMSO d$_6$) 9.62 (bs, 1H), 8.49 (s, 1H), 8.37 (d, 1H), 8.29 (d, 1H), 8.05 (bs, 1H), 7.87 (s, 1H), 7.80 (d, 1H), 7.68 (d, 1H), 7.41 (m, 1H), 7.10 (d, 1H), 4.11 (s, 2H), 2.19 (s, 3H), 1.29 (s, 6H).

Example 57

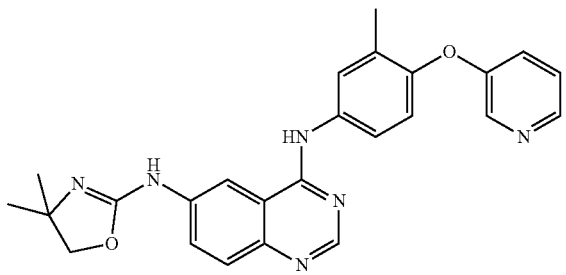 [SMILES: Cc1cc(Nc2ncnc3ccc(NC4=NC(C)(C)CO4)cc23)ccc1Oc1cccnc1]

N6-(4,4-Dimethyl-4,5-dihydro-oxazol-2-yl)-N4-[3-methyl-4-(pyridin-3-yloxy)-phenyl]-quinazoline-4,6-diamine MS ESI (+) m/z 441 (m+1) detected; $^1$H NMR (400 mHz, DMSO d$_6$) 9.54 (bs, 1H), 8.46 (s, 1H), 8.33 (d, 1H), 8.29 (d, 1H), 8.00 (bs, 1H), 7.84 (s, 1H), 7.77 (d, 1H), 7.65 (d, 1H), 7.37 (m, 1H), 7.26 (m, 1H), 7.03 (d, 1H), 4.07 (s, 2H), 2.19 (s, 3H), 1.28 (s, 6H).

Example 58

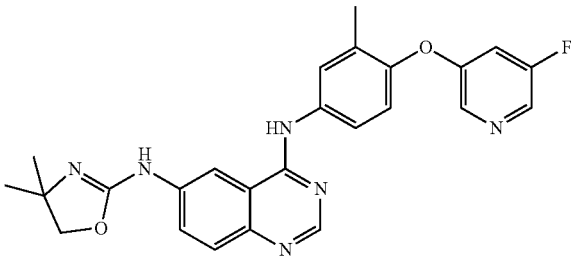 [SMILES: Cc1cc(Nc2ncnc3ccc(NC4=NC(C)(C)CO4)cc23)ccc1Oc1cncc(F)c1]

N6-(4,4-Dimethyl-4,5-dihydro-oxazol-2-yl)-N4-[4-(5-fluoro-pyridin-3-yloxy)-3-methyl-phenyl]-quinazoline-4,6-diamine MS ESI (+) m/z 459 (m+1) detected; $^1$H NMR (400 mHz, DMSO d$_6$) 9.70 (bs, 1H), 8.51 (s, 1H), 8.43 (d, 1H), 8.20 (d, 1H), 8.11 (bs, 1H), 7.86 (s, 1H), 7.80 (d, 1H), 7.69 (m 2H), 7.29 (d, 1H), 7.11 (d, 1H), 4.61 (s, 2H), 2.20 (s, 3H), 1.30 (s, 6H).

The amino alcohols used in the above examples are either known compounds or are prepared as described below.

Example 59

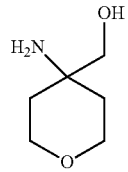

Preparation of (4-aminotetrahydropyran-4-yl)-methanol (4-Amino-tetrahydropyran-4-yl)-methanol is prepared by adding LAH (99%, 1.2 g), portionwise, to a stirred mixture of 4-aminotetrahydropyran-4-carboxylic acid hydrochloride (2.0 g, 11.0 mmol) in THF (30 mL) at 0° C. Upon completion of addition, the reaction mixture is warmed to room temperature and stirred for 1 hour. The reaction mixture is cooled to 0° C. and cautiously quenched by the portionwise addition of Na$_2$SO$_4$.10H$_2$O (4 g). The reaction mixture is diluted with ethyl acetate, warmed to room temperature, and filtered through Celite to give the desired product.

Example 60

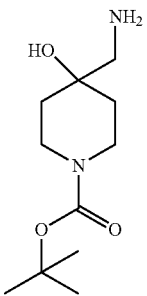 [SMILES: CC(C)(C)OC(=O)N1CCC(O)(CN)CC1]

Preparation of 4-aminomethyl-4-hydroxypiperidine-1-carboxylic acid tert-butyl ester 4-Aminomethyl-4-hydroxy-piperidine-1-carboxylic acid tert-butyl ester is prepared from 1-oxa-6-aza-spiro[2.5]octane-6-carboxylic acid tert-butyl ester (Bourrain et al Bioorg. Med. Chem. Lett. 9(23):3369-3374 (1999)). Concentrated aqueous NH$_4$OH (6 mL) is added to a solution of 1-oxa-6-aza-spiro[2.5]octane-6-carboxylic acid tert-butyl ester (0.50 g, 2.3 mmol) in MeOH (4 mL) at 0° C. The reaction mixture is removed from the cooling and allowed to warm to room temperature. After 7 hours, the reaction mixture is concentrated under reduced pressure to afford desired product as a white solid.

Example 61

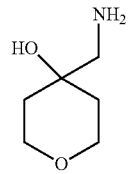

Preparation of 4-aminomethyltetrahydro-pyran-4-ol

4-Aminomethyl-tetrahydro-pyran-4-ol is prepared from 1,6-dioxa-spiro[2.5]octane. A MeOH (3.5 mL) solution of 1,6-dioxa-spiro[2.5]octane (0.19 g, 1.7 mmol) is added to concentrated aqueous NH$_4$OH (4.3 mL) at 0° C. The reaction mixture is warmed to room temperature and stirred for 16 hours. The reaction mixture is concentrated under reduced pressure and purified by column chromatography (10% MeOH, 2% Et₃N in DCM) to afford 90 mg (41%) of the desired product as a white solid.

Example 62

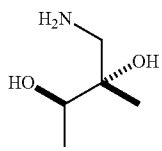

Preparation of (2RS, 3SR)-1-amino-2-methylbutane-2,3-diol (2RS, 3SR)-1-Amino-2-methylbutane-2,3-diol is prepared from acetic acid 1,2-dimethyl-allyl ester. mCPBA (17 g, 69 mmol) is slowly added to a stirred solution of acetic acid 1,2-dimethylallyl ester (6.80 g, 53.1 mmol) in methylene chloride (500 mL). After 4 hours, the reaction is washed with saturated NaHCO₃, water and brine. The organic layer is dried (Na₂SO₄) and concentrated under reduced pressure. Purification by column chromatography (20% diethyl ether in pentane; repeated) gives (1-RS, 2-SR)-acetic acid 1-(-2-methyloxiranyl)-ethyl ester (3.45 g, 45%). A small amount of (1-RS, 2-SR)-acetic acid 1-(-2-methyloxiranyl)-ethyl ester was converted to (2RS, 3SR)-3,4-epoxy-3-methyl-2-butanaol (*JACS* (1990) 112(13):5285) by treatment with K₂CO₃ in MeOH to confirm the relative stereochemistry of this racemic material. K₂CO₃ (1.54 g, 11.1 mmol) is added to a stirred solution of acetic acid (R*)-1-((S*)-2-methyloxiranyl)-ethyl ester (1.70 g, 11.8 mmol) in MeOH (12 mL). After 1 hour, the reaction mixture is filtered through Celite. The filtrate is added slowly via an addition funnel to 20 mL concentrated aqueous NH₄OH. After stirring 16 hours, the reaction mixture is concentrated under reduced pressure and purified by column chromatography (20% MeOH, 2% Et₃N in DCM) to afford 0.97 g (69%) of the desired product as a light yellow oil.

Example 63

Preparation of N⁴-[3-chloro-4-(3-fluorobenzyloxy)-phenyl]-N⁶-(4,5-dihydro-oxazol-2-yl)-N⁶-methylquinazoline-4,6-diamine Step A: A solution of N⁴-[3-chloro-4-(3-fluorobenzyloxy)-phenyl]-quinazoline-4,6-diamine (1.09 g, 2.76 mmol) and di-t-butyl dicarbonate (2.0 g, 3.3 equiv) was heated in t-BuOH:DCE (1:1) in a sealed tube at 90-95° C. for 20 minutes, then cooled to room temperature. The volatiles were removed under reduced pressure, and the product was purified by silica gel chromatography (60% EtOAc/hexanes), affording a yellow solid (670 mg, 49%).

Step B: The purified material from Step A was taken up in THF (5-10 mL) at 0° C., and LAH (1.0 M solution in THF, 1 equivalent) was added. The solution was refluxed for 1 hour, then cooled to room temperature. The reaction was diluted with THF and quenched by the portionwise addition of excess sodium sulfate decahydrate. The reaction was filtered and the product was purified by silica gel chromatography (100% EtOAc), affording a yellow solid.

Step C: The purified material from Step B (63 mg, 0.15 mmol) was taken up in THF (3 mL) and 2-chloroethyl isocyanate (32 μL, 2.4 equivalents) was added. The reaction was heated at 50° C. until a heavy precipitate formed. The product is obtained as a bright yellow solid by vacuum filtration (26 mg, 33%).

Step D: The material from Step C was taken up in MeCN (2 mL) and 40% KF on alumina (130 mg, 18 equivalents) was added. The mixture was refluxed for 12 hours, diluted with MeCN, and filtered through Celite. Silica gel chromatography afforded N⁴-[3-chloro-4-(3-fluorobenzyloxy)-phenyl]-N⁶-(4,5-dihydro-oxazol-2-yl)-N⁶-methyl-quinazoline-4,6-diamine (6 mg, 25%).

Additional compounds of the present invention include:

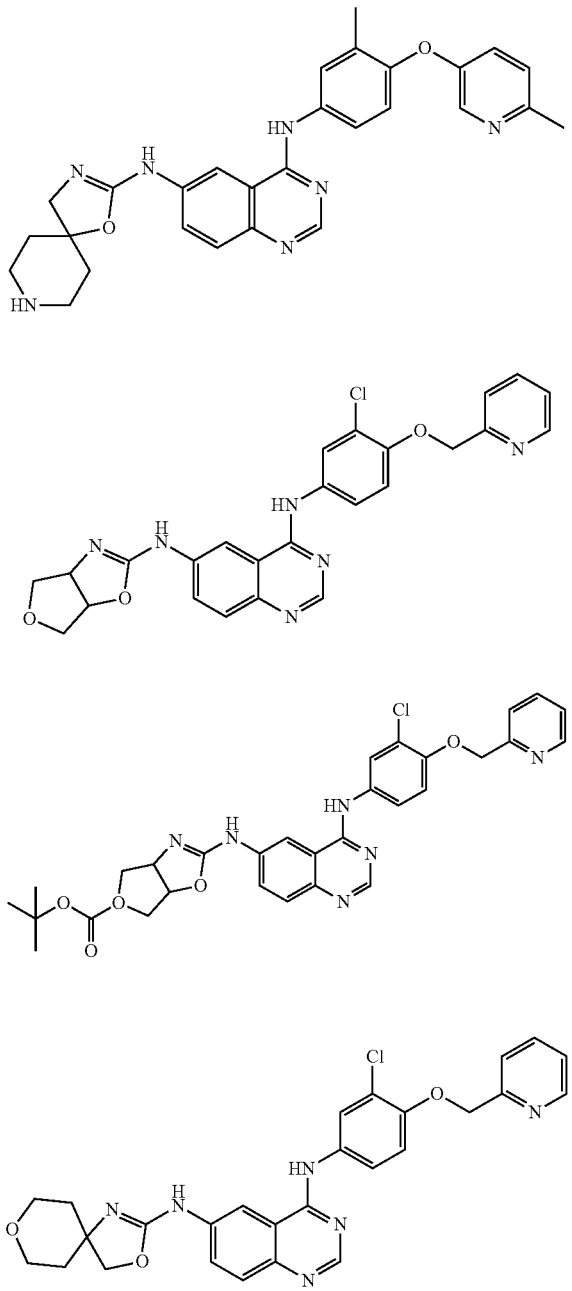

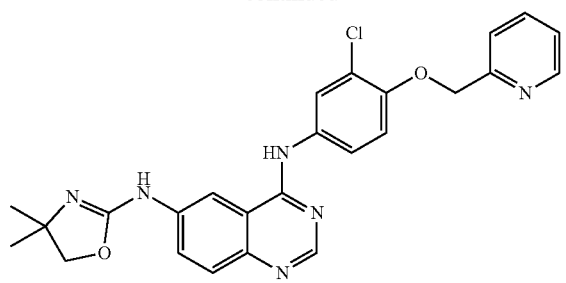
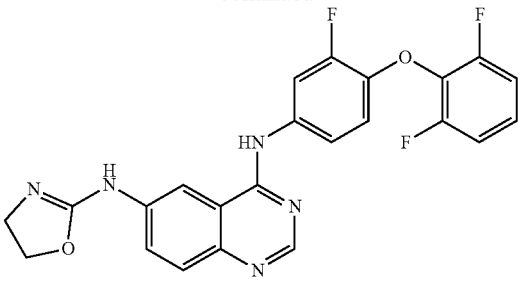

53
-continued
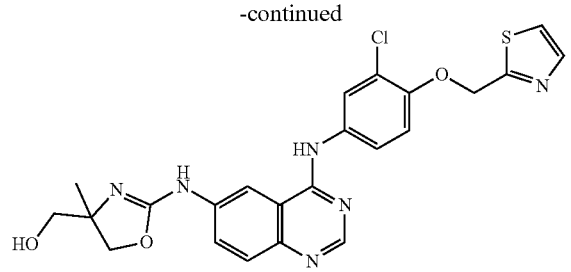
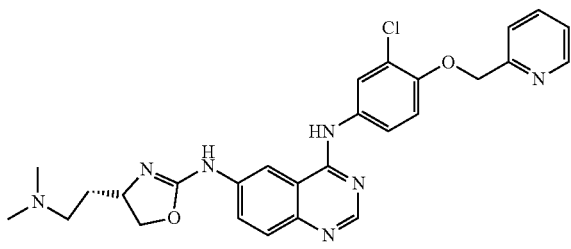
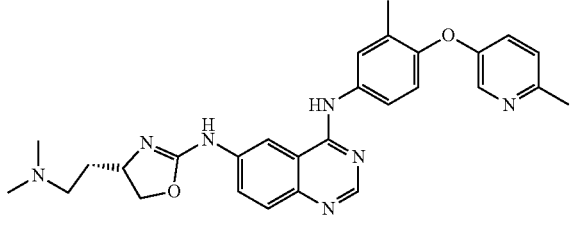
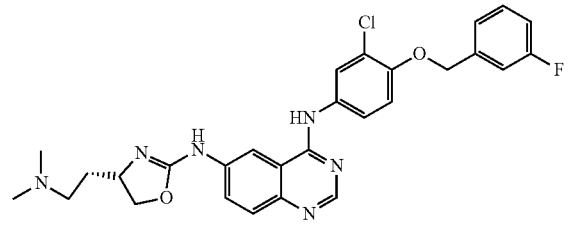
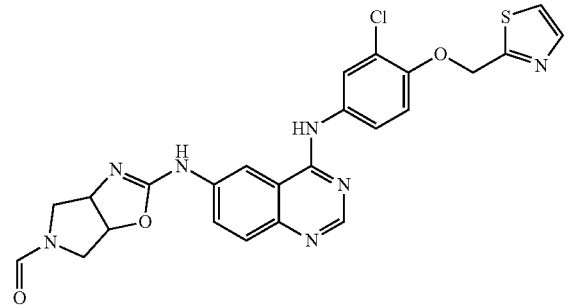
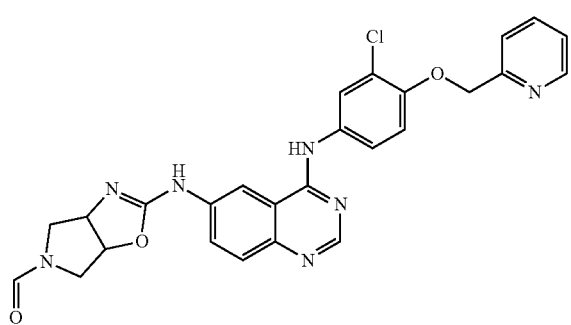
54
-continued
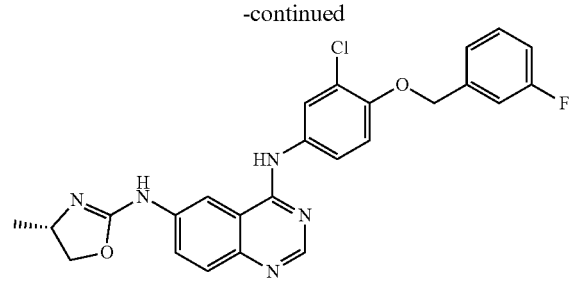
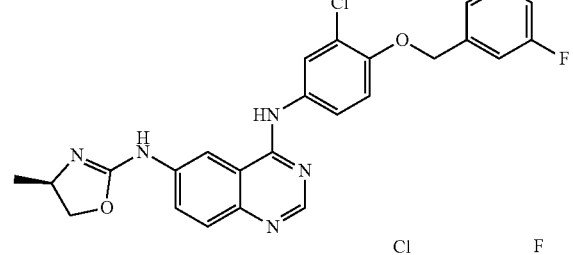
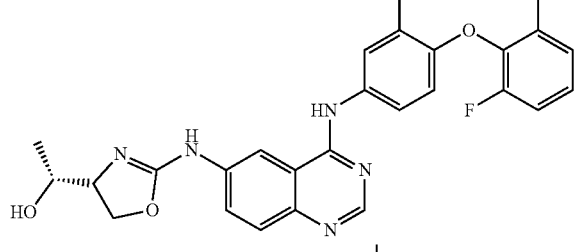
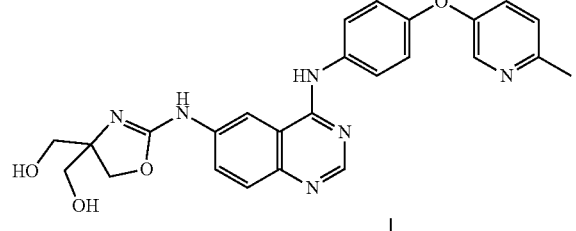
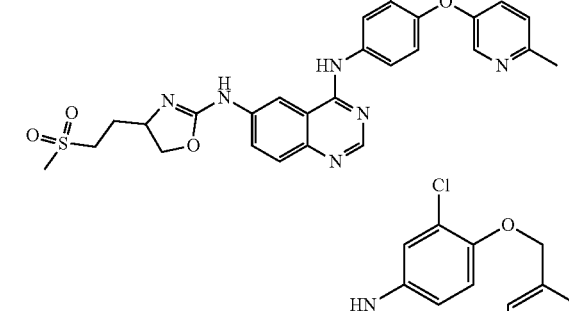
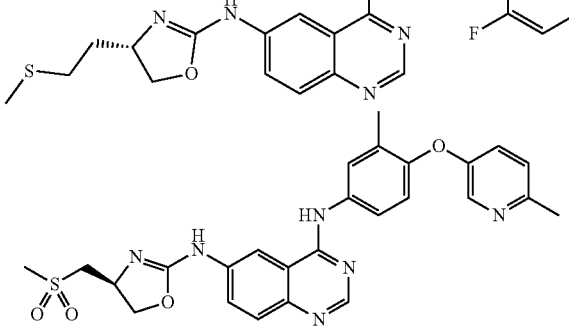

55
-continued
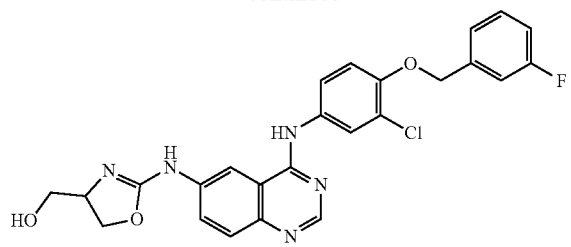
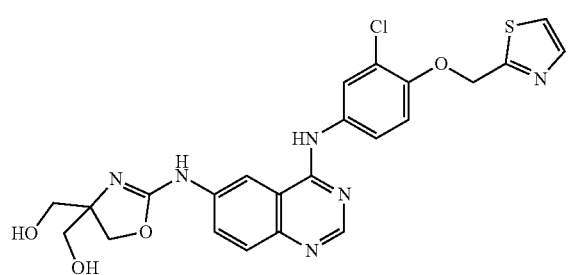
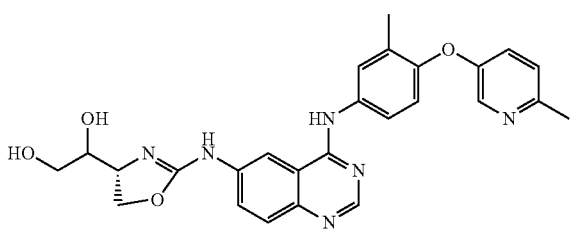
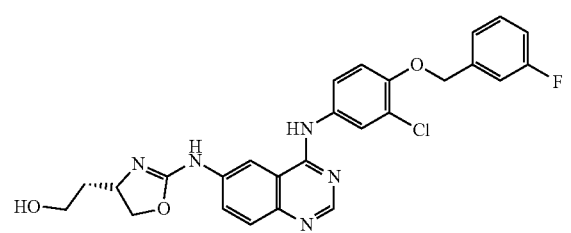
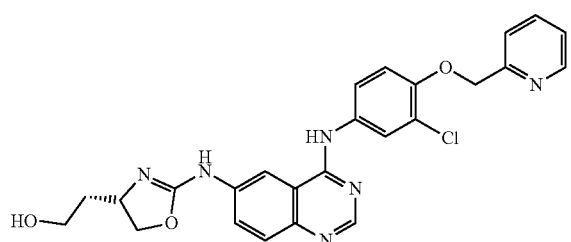
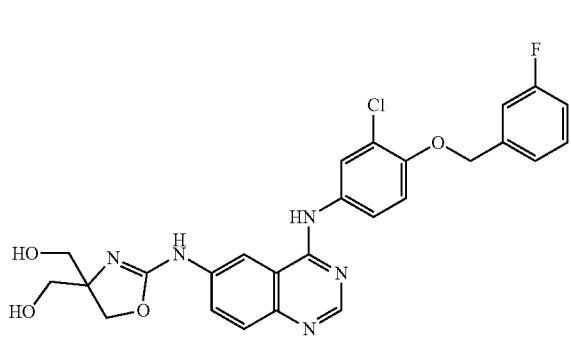
56
-continued
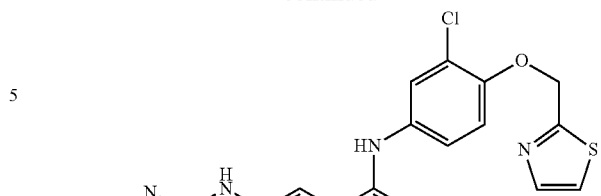
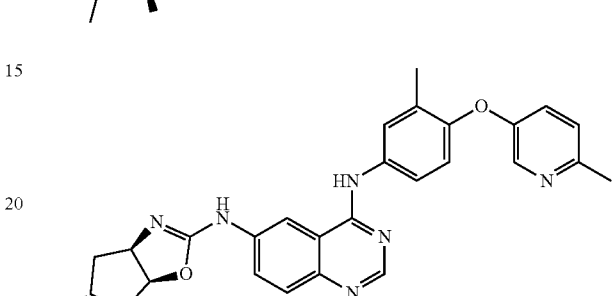
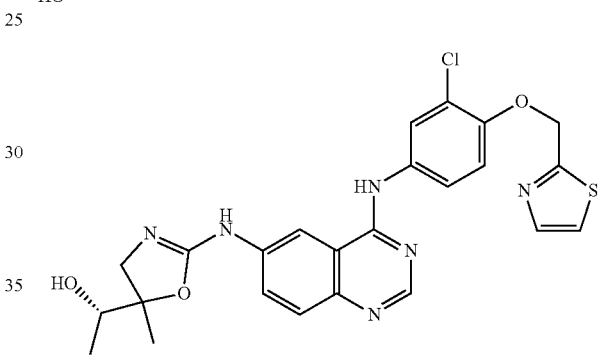
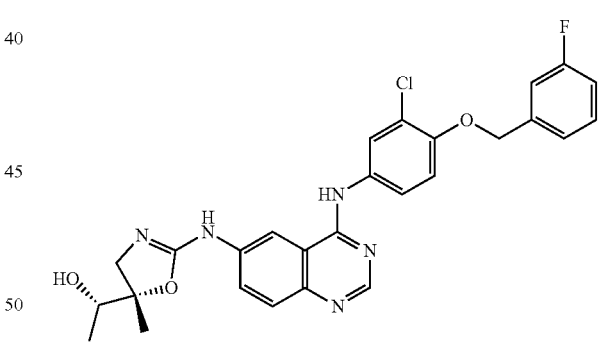
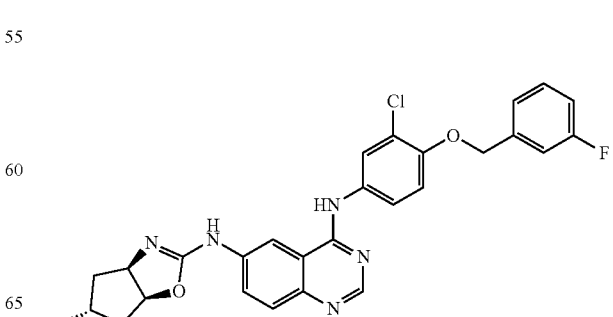

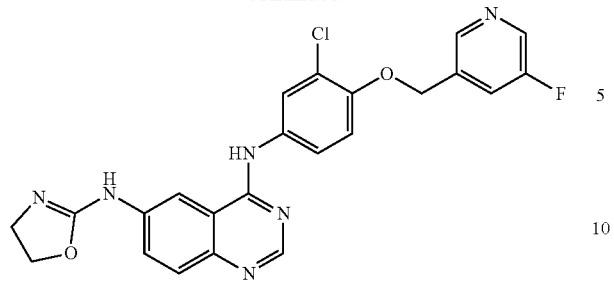
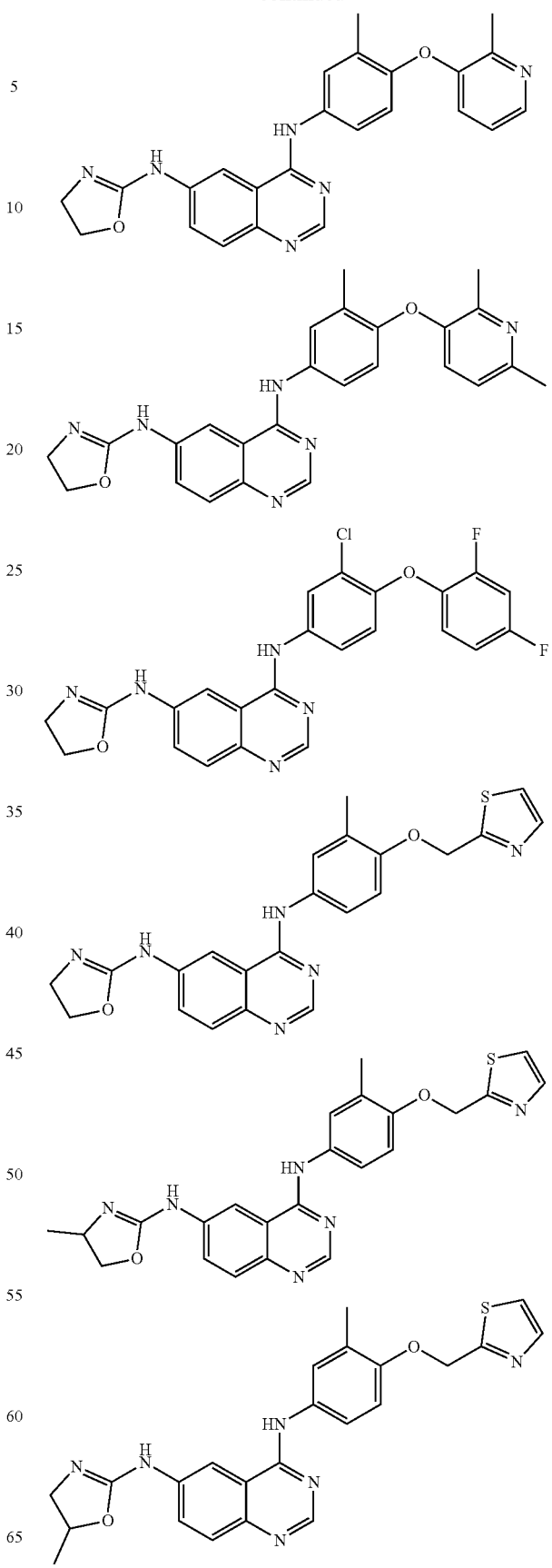

-continued
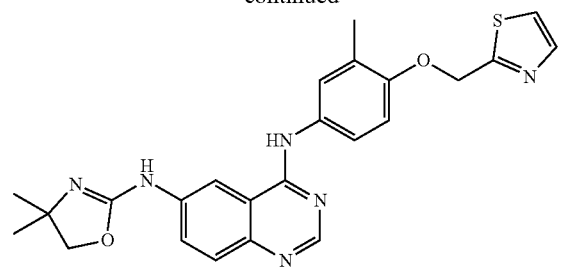
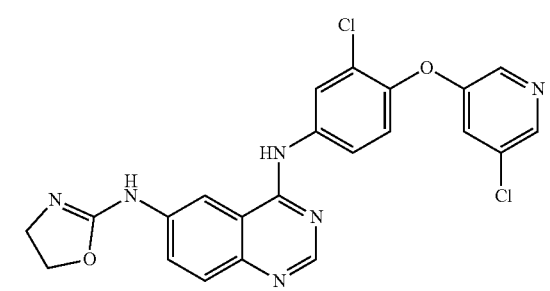
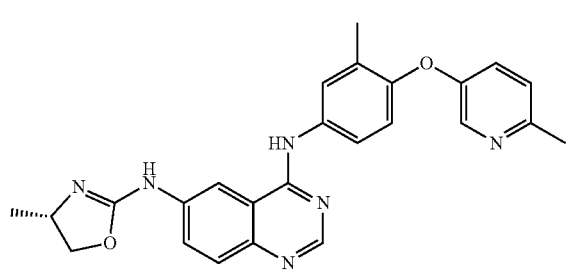
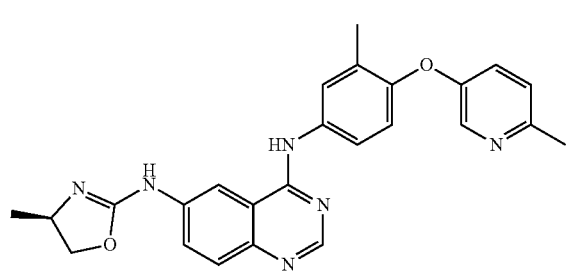
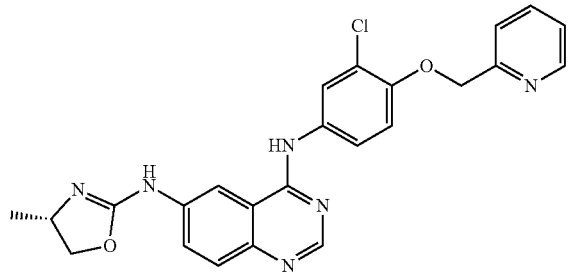
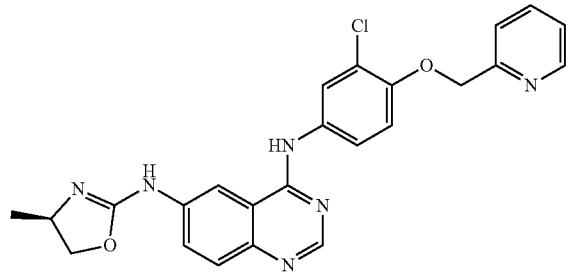
-continued
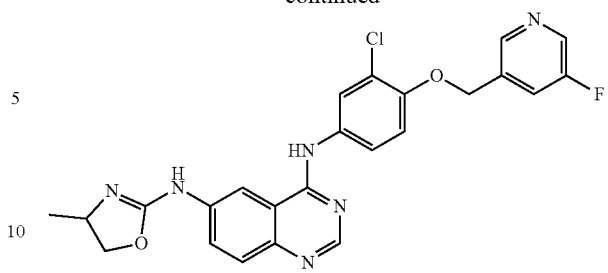
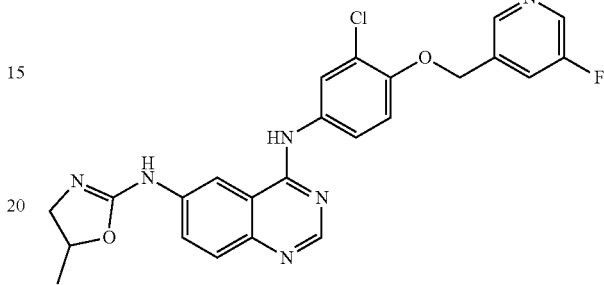
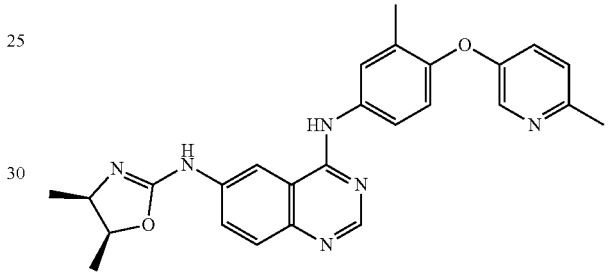
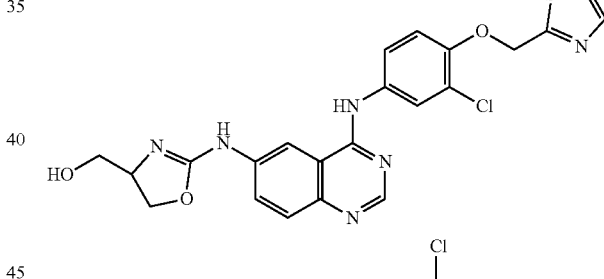
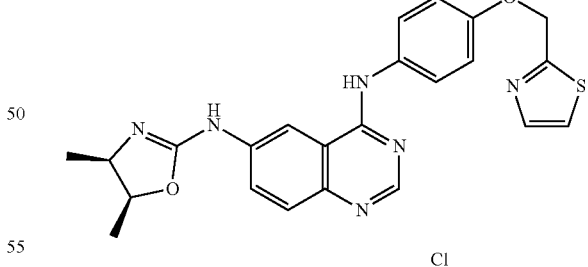
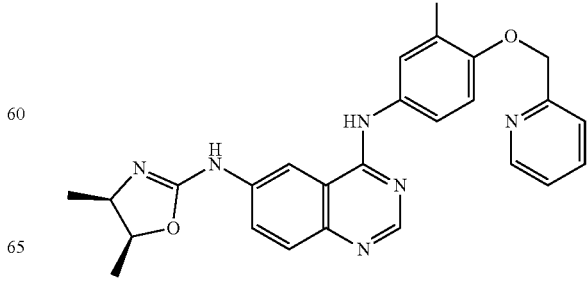

61
-continued
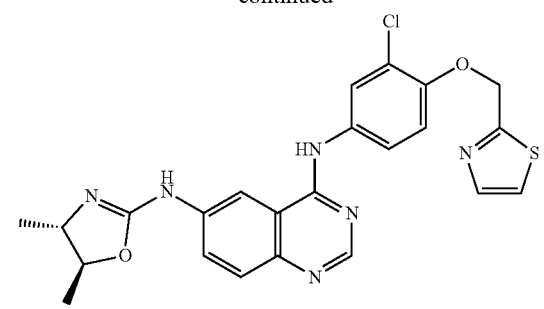
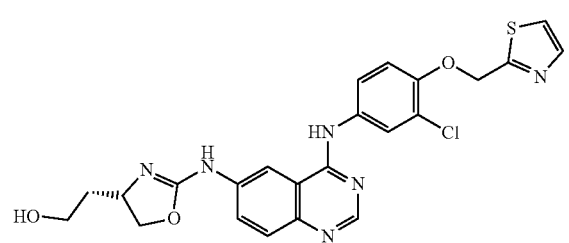
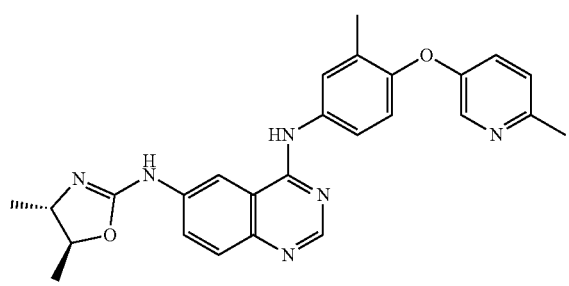
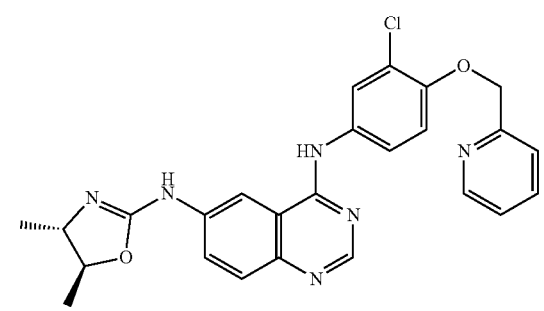
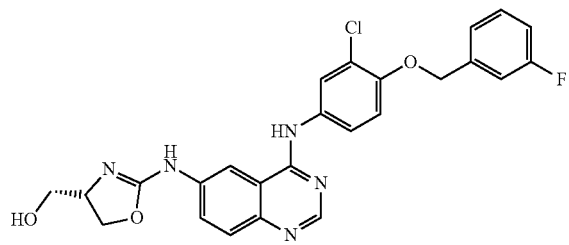
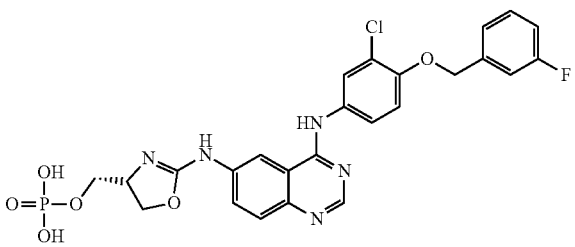
62
-continued
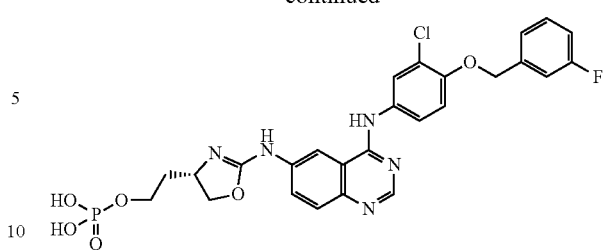
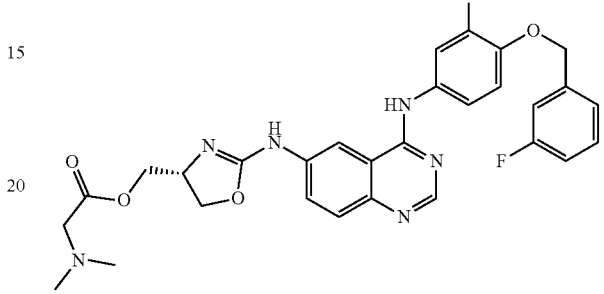
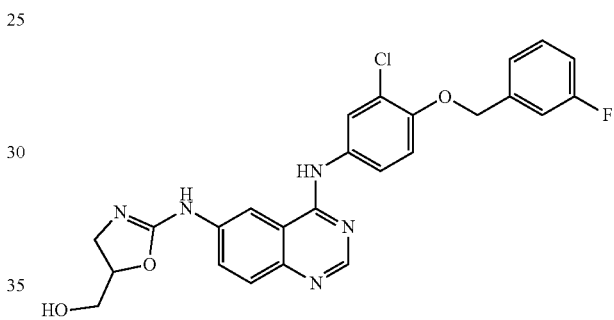
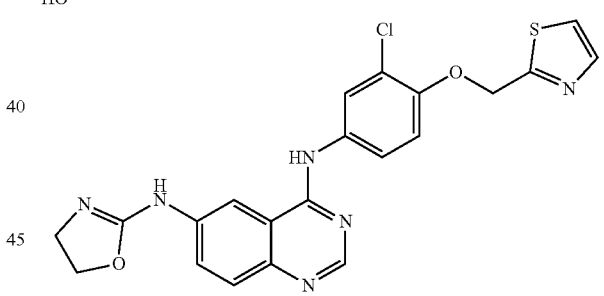
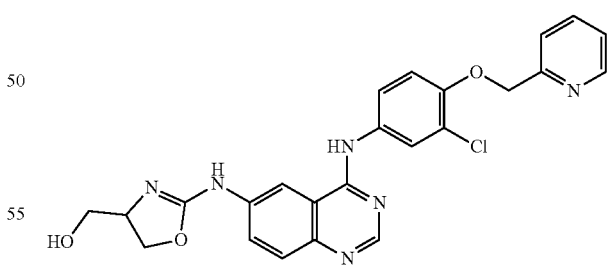
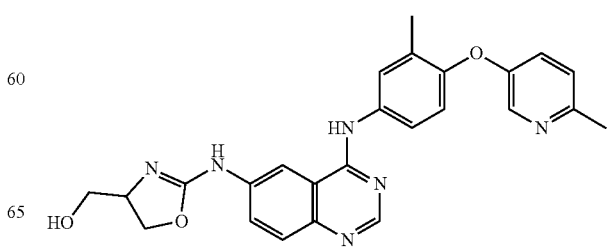

-continued

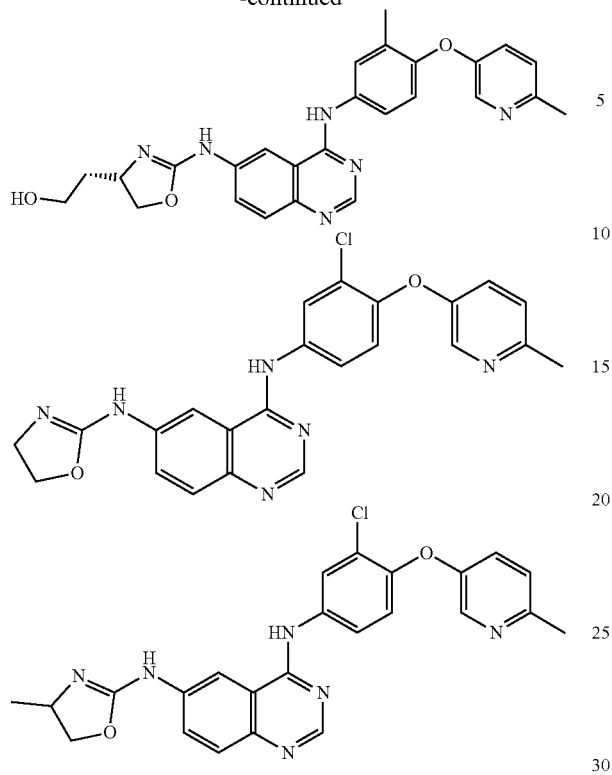

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups.

What is claimed is:

1. A method of inhibiting the activity of ErbB2 comprising administering an effective amount of a compound selected from the group consisting of:

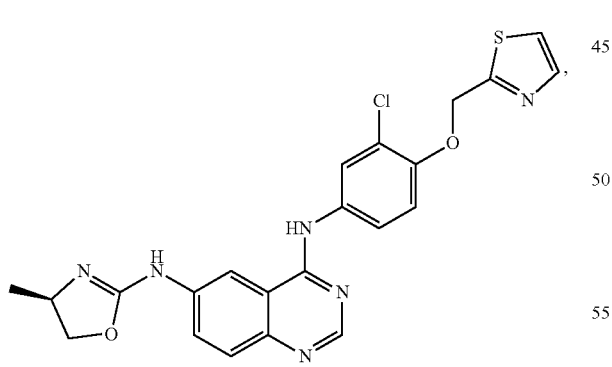

-continued

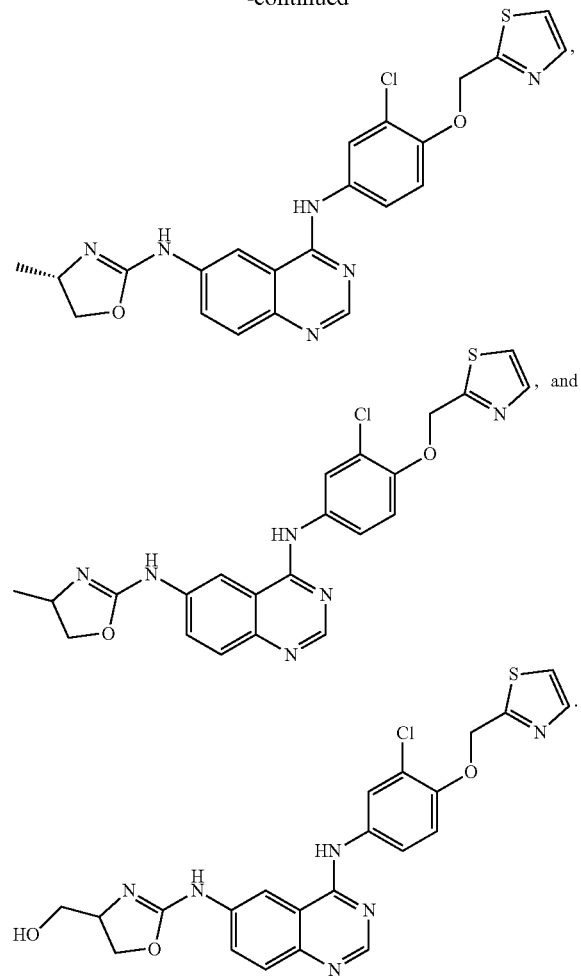

2. The method of claim 1, wherein the compound is:

* * * * *